US008258105B2

(12) United States Patent
Siwkowski et al.

(10) Patent No.: US 8,258,105 B2
(45) Date of Patent: *Sep. 4, 2012

(54) ANTISENSE OLIGONUCLEOTIDES OPTIMIZED FOR KIDNEY TARGETING

(75) Inventors: Andrew M. Siwkowski, Carlsbad, CA (US); Edward Wancewicz, Poway, CA (US); Thomas A. Leedom, Escondido, CA (US); Lynnetta Watts, Carlsbad, CA (US); Mausumee Guha, Trabuco Canyon, CA (US); Brett P. Monia, Encinitas, CA (US)

(73) Assignee: Isis Pharmaceuticals, Inc., Carlsbad, CA (US)

( * ) Notice: Subject to any disclaimer, the term of this patent is extended or adjusted under 35 U.S.C. 154(b) by 106 days.

This patent is subject to a terminal disclaimer.

(21) Appl. No.: 10/946,498

(22) Filed: Sep. 21, 2004

(65) Prior Publication Data
US 2005/0113326 A1    May 26, 2005

Related U.S. Application Data

(60) Provisional application No. 60/509,450, filed on Oct. 7, 2003, provisional application No. 60/517,334, filed on Nov. 3, 2003.

(51) Int. Cl.
C12N 15/11    (2006.01)
(52) U.S. Cl. .................................................. 514/44 A
(58) Field of Classification Search ................ 514/44, 514/44 A
See application file for complete search history.

(56) References Cited

U.S. PATENT DOCUMENTS

| | | | |
|---|---|---|---|
| 5,240,847 A | 8/1993 | Heckl et al. | |
| 5,366,878 A | 11/1994 | Pederson et al. | |
| 5,883,082 A | 3/1999 | Bennett et al. | |
| 5,998,148 A | 12/1999 | Bennett et al. | |
| 6,133,246 A | 10/2000 | McKay et al. | |
| 6,150,101 A * | 11/2000 | Grotendorst et al. | 435/6 |
| 6,162,616 A | 12/2000 | Shyjan | |
| 6,211,440 B1 | 4/2001 | Briggs et al. | |
| 6,284,538 B1 | 9/2001 | Monia et al. | |
| 6,414,126 B1 * | 7/2002 | Ellsworth et al. | 536/17.2 |
| 6,506,559 B1 | 1/2003 | Fire et al. | |
| 6,537,751 B1 | 3/2003 | Cohen et al. | |
| 6,582,908 B2 | 6/2003 | Fodor et al. | |
| 6,809,193 B2 | 10/2004 | McKay et al. | |
| 6,875,747 B1 * | 4/2005 | Iversen et al. | 536/24.5 |
| 6,965,025 B2 | 11/2005 | Gaarde et al. | |
| 7,273,932 B1 | 9/2007 | LaBarbera et al. | |
| 7,507,810 B2 | 3/2009 | Karras et al. | |
| 8,084,436 B2 * | 12/2011 | Freier et al. | 514/44 A |
| 2002/0052326 A1 | 5/2002 | Washburn | |
| 2002/0137708 A1 | 9/2002 | Bennett et al. | |
| 2003/0040497 A1 | 2/2003 | Teng et al. | |
| 2003/0055019 A1 | 3/2003 | Shimkets et al. | |
| 2003/0083280 A1 | 5/2003 | Crooke et al. | |
| 2003/0087411 A1 | 5/2003 | Bird et al. | |
| 2003/0223975 A1 * | 12/2003 | Tonks et al. | 424/93.21 |
| 2003/0232336 A1 | 12/2003 | Curtis et al. | |
| 2005/0032693 A1 * | 2/2005 | Gerritsen et al. | 514/12 |
| 2005/0053981 A1 * | 3/2005 | Swayze et al. | 435/6 |
| 2005/0059629 A1 * | 3/2005 | Gaarde et al. | 514/44 |
| 2005/0107325 A1 | 5/2005 | Manoharan et al. | |
| 2005/0191653 A1 | 9/2005 | Freier et al. | |
| 2005/0250719 A1 * | 11/2005 | Menne et al. | 514/44 |
| 2006/0063722 A1 | 3/2006 | Washburn et al. | |
| 2007/0031844 A1 | 2/2007 | Khvorova et al. | |
| 2007/0238866 A1 | 10/2007 | Deshpande et al. | |
| 2007/0299028 A1 | 12/2007 | Siwokowski et al. | |

FOREIGN PATENT DOCUMENTS

| | | |
|---|---|---|
| EP | 1 293 569 A2 | 3/2003 |
| EP | 1 308 459 A2 | 5/2003 |
| WO | WO 97/29780 | 8/1997 |
| WO | WO 99/60012 | 11/1999 |
| WO | WO 99/66959 | 12/1999 |
| WO | WO 00/13706 | 3/2000 |
| WO | WO 00/18918 | 4/2000 |
| WO | WO 00/27868 | 5/2000 |
| WO | WO 00/35936 | 6/2000 |
| WO | WO 01/29217 A2 | 4/2001 |
| WO | WO 02/096927 | 12/2002 |
| WO | WO 2004/016754 | 2/2004 |
| WO | WO 2005/038013 | 4/2005 |
| WO | WO 2005/042552 | 5/2005 |

OTHER PUBLICATIONS

Monia et al. The Journal of Biological Chemistry 268:14514-14522, 1993.*
Agrawal et al. 2000-Molecular Medicine Today, vol. 61, pp. 72-81.*
Gerwitz et al, PNAS, 93:3161-3163, 1996.*
Adler et al., "Glomerular mRNAs in human type 1 diabetes:Biochemical evidence for microalbuminuria as a manifestation of diabetic nephropathy", Kidney International 2001 60:2330-2336.
Agrawal et al., "Pharmacokinetics, biodistribution, and stability of oligodeoxynucleotide phosphorothioates in mice", Proc. Natl. Acad. Sci. USA 1991 88:7595-7599.
El-Din et al., "Connective Tissue Growth Factor:What's in a Name?", Molecular Genetics and Metabolism 2000 71:276-292.
Geary et al., "Pharmacokinetics of phosphorothioate antisense oligodeoxynucleotides", Current Opinion in Investigational Drugs 2001 2(4):562-573.
Geary et al., "Pharmacokinetic Properties of 2'-O-(2-Methoxyethyl)-Modified Oligonucleotide Analogs in Rats", J. Pharmacology and Experimental Therapeutics 2001 296(3):890-897.
Hishikawa et al., "Connective Tissue Growth Factor Induces Apoptosis in Human Breast Cancer Cell Line MCF-7", J. Biol. Chem. 1999 274(52):37461-37466.

(Continued)

Primary Examiner — Brian Whiteman
(74) Attorney, Agent, or Firm — Jones Day

(57) ABSTRACT

The present invention provides antisense compounds and methods for modulating the expression of target genes expressed in the kidney. In particular, this invention provides antisense oligonucleotide compounds optimized for targeting nucleic acid molecules expressed in the kidney. Such compounds are shown herein to efficiently modulate the expression of target genes SGLT2 and connective tissue growth factor (CTGF) in the kidney.

25 Claims, No Drawings

OTHER PUBLICATIONS

Hishikawa et al., "Transforming growth factor-$\beta_1$ induces apoptosis via connective tissue growth factor in human aortic smooth muscle cells", European Journal of Pharmacology 1999 385:287-290.

Hishikawa et al., "Static Pressure Regulates Connective Tissue Growth Factor Expression in Human Mesangial Cells", J. Biol. Chem. 2001 276(20):16797-16803.

Oku et al., "T-1095, an Inhibitor of Renal $Na^+$-Glucose Cotransporters, May Provide a Novel Approach to Treating Diabetes", Diabetes 1999 48:1794-1800.

Lau et al., "The CCN Family of Angiogenic Regulators:The Integrin Connection", Experimental Cell Research 1999 248:44-57.

Maier et al., "Enzymatic Degradation of Various Antisense Oligonucleotides:Monitoring and Fragment Identification by MECC and ES-MS", Biomedical Peptides, Proteins & Nucleic Acids 1995 1:235-242.

Nawano et al., "Hyperglycemia contributes insulin resistance in hepatic and adipose tissue but not skeletal muscle of ZDF rats", Am. J. Physiol. Endocrinol. Metab. 2000 278:E535-E543.

Oku et al., "Antidiabetic effect of T-1095, an inhibitor of $Na^+$-glucose cotransporter, in neonatally streptozotocin-treated rats", European Journal of Pharmacology 2000 391:183-192.

Riser et al., "Urinary CCN2 (CTGF) as a possible predictor of diabetic nephropathy:Preliminary report", Kidney International, 2003 64:451-458.

Shaw et al., Modified deoxyoliogonucleotides stable to exonuclease degradation in serum, Nucleic Acids Research 1991 19(4):747-750.

Shimo et al., "Inhibition of Endogenous Expression of Connective Tissue Growth Factor by Its Antisense Oligonucleotide and Antisense RNA Suppresses Proliferation and Migration of Vascular Endothelial Cells[1]", J. Biochem. 1998 124:130-140.

Tsujihara et al., "$Na^+$-Glucose Cotransporter (SGLT) Inhibitors as Antidiabetic Agents. 4. Synthesis and Pharmacological Properties of 4'-Dehydroxyphlorizin Derivatives Substituted on the B Ring", J. Med. Chem. 1999 42:5311-5324.

Twigg et al., "Advanced Glycosylation End Products Up-Regulate Connective Tissue Growth Factor (Insulin-Like Growth Factor-Binding Protein-Related Protein 2) in Human Fibroblasts:A Potential Mechanism for Expansion of Extracellular Matrix in Diabetes Mellitus", Endocrinology 2001 142(5):1760-1769.

Twigg et al., "The stability, toxicity and effectiveness of unmodified and phosphorothioate antisense oligonucleotides in *Xenopus* oocytes and embryos", Nucleic Acids Research 1990 18(7):1763-1769.

Wright E.M., "Renal $Na^+$-glucose cotransporters", Am J Physiol Renal Physiol 2001 280:F10-F18.

Balboa, M. A. et al., "Protein Kinase $C_\alpha$ Mediates Phospholipase D Activation by Nucleotides and Phorbol Ester in Madin-Darby Canine Kidney Cells," *J. Biol. Chem.* (1994), 269(14):10511-10516.

Godson, C. et al., "Inhibition of Expression of Protein Kinase Ca by Antisense cDNA Inhibits Phorbol Ester-mediated Arachidonate Release," *J. Biol. Chem.* (1993) 268(16):11946-11950.

Ma, D. D. F., et al., "Synthetic oligonucleotides as therapeutics: the coming of age," *Biotechnology Annual Review* (2000) 5:155-196.

Garay et al., "Inhibition of Hypoxia/Reoxygenation-Induced Apoptosis by an Antisense Oligonucleotide Targeted to JNK1 in Human Kidney Cells," *Biochem. Pharmacol.* 59:1033-1043 (2000).

Kanai et al., "The Human Kidney Low Affinity Na+/glucose Cotransporter SGLT2," *J. Clin. Invest.* 93:397-404 (1994).

Arakawa et al., "Improved Diabetic Syndrome in C57BL/KsJ-db/db Mice by Oral Administration of the Na-Glucose Cotransporter Inhibitor T-1095" Br. J. Pharmacol. (2001) 132:578-586.

Branch et al., "A good antisense molecule is hard to find" *TIBS* (1998) 23:45-50.

Brown et al., "Glucose Transporters: Structure, Function, and Consequences of Deficiency" J. Inherit. Metab. Dis. (2000) 23:237-246.

Chin "On the Preparation and Utilization of Isolated and Purified Oligonucleotides" Document purportedly located on a CD-ROM and contributed to the public collection of the Katherine R. Everett Law Library of the University of North Carolina on Mar. 14, 2002, p. 1.

Chirila et al., "The use of synthetic polymers for delivery of therapeutic antisense oligodeoxynucleotides" Biomaterials (2002) 23:321-342.

Crooke et al., "Basic Principles of Antisense Therapeutics" Antisense Research and Application (1998) Chapter 1:1-50.

Crooke et al. "Progress in Antisense Technology" Ann. Rev. Medicine (2004) 55:61-95.

Dang et al., "Oncogenic Alterations of Metabolism" TIBS (1999) 24:68-72.

Hediger te al., "Molecular Genetics of the Human Na/Glucose Cotransporter" Klin. Wochenschr. (1989) 67:843-846.

Ishikawa et al., "SGLT Gene Expression in Primary Lung Cancers and their Metastatic Lesions" Jpn. J. Cancer Res. (2001) 92:874-879.

Kong et al., "Cloning and Expression of a Mammalian Na/Amino Acid Cotransporter with Sequence Similarity to Na/Glucose Cotransporters" J. Biol. Chem. (1993) 268:1509-1512.

MacKenzie et al., "Biophysical Characteristics of the Pig Kidney Na/Glucose Cotransporter SGLT2 Reveal a Common Mechanism for SGLT1 and SGLT2" J. Biol. Chem. (1996) 271:32678-32683.

MacKenzie et al., "SAAT1 is a Low Affinity Na/Glucose Cotransporter and not an Amino Acid Transporter" J. Biol. Chem. (1994) 269:22488-22491.

New England Biolabs, 1998/1999 Catalog, pp. 121 and 284.

Opalinska et al., "Nucleic-acid therapetuics: basic principles and recent applications" Nature Rev. (2002) 1:503-514.

Peracchi et al., "Prospects for antiviral ribozymes and deoxyribozymes" Rev. Med. Virol. (2004) 14:47-64.

Pontoglio et al., "HNF-1a Controls Renal Glucose Reabsorption in Mouse and Man" EMBO Reports (2000) 1:359-365.

Reynolds et al., "Rational siRNA design for RNA interference" Nature Biotechnology (2004) 22(3):326-330.

Sanghvi et al., "Heterocyclic Base Modifications in Nucleic Acids and Their Applications in Antisense Oligonucleotides" Antisense Research and Applications (1993) pp. 273-288.

Tabatabai et al., "Differential Regulation of Mouse Kidney Sodium-Dependent Transporters mRNA by Cadmium" Toxicol. Appl. Pharmacol. (2001) 177:163-173.

Turner et al., "Heterogeneity of Sodium-Dependent D-Glucose Transport Sites Along the Proximal Tubule: Evidence from Vesicle Studies" Am. J. Physiol. (1982) 242:F406-F414.

Turner et al., "Stoichiometric Studies of the Rental Outer Cortical Brush Border Membrane p-Glucose Transporter" J. Membrane Biol. (1982) 67:73-80.

Tuschl et al., The siRNA user guide, 2001.

Van Den Heuvel et al., "Autosomal Recessive Renal Glucosuria Attributable to a Mutation in the Sodium Glucose Cotransporter (SGLT2)" Hum. Genet. (2002) 111:544-547.

Vestri et al., "Changes in Sodium or Glucose Filtration Rate Modulate Expression of Glucose Transporters in Renal Proximal Tubular Cells of Rat" J. Membrane Biol. (2001) 182:105-112.

Watts et al., "Reduction of Hepatic and Adipose Tissue Glucocorticoid Receptor Expression With Antisense Oligonucleotides Improves Hyperglycemia and Hyperlipidemia in Diabetic Rodents Withouth Causing Systemic Glucocorticoid Antagonism" Diabetes (2005) 54:1846-1853.

Watts et al., "Reduction of Sodium Dependent Glucose Transporter SGLT2 Expression with an Antisense Oligonucleotide (ASO) Optimized to Target the Kidney Results in Significant Glucose Lowering Effects in Diabetic Mice" Diabetes (2005) 54, Suppl. 1: A386.

Wells et al., "Cloning of a Human Kidney cDNA with Similarity to the Sodium-Glucose Cotransporter" Am. J. Physiol. (1992) 263:F459-F465.

Wells et al., "Localization of the Na+/Glucose Cotransporter Gene SGLT-2 to Human Chromosome 16 Close to the Centromere" Genomics (1993) 17:787-789.

You et al., "Molecular Characteristics of Na-Coupled Glucose Transporters in Adult and Embryonic Rat Kidney" J. Biol. Chem. (1995) 270:29365-29371.

Zhou et al., Human Cardiomyocytes Express High Level of NA+/Glucose Cotransporter I (SGLT), Journal of Cellular Biochemistry (2003) 90:339-346.

European Search Report for Application No. EP 04800679.5 dated Mar. 6, 2008.

European Search Report for Application No. EP 04788853.2 dated Mar. 6, 2008.

European Search Report for Application No. EP 07811875.9 dated May 15, 2009.

International Search Report for Application No. PCT/US04/36620 dated Nov. 23, 2005.
International Search Report for Application No. PCT/US04/30785 dated Jan. 31, 2005.

International Search Report for Application No. PCT/US07/68406 dated Mar. 13, 2008.

* cited by examiner

ANTISENSE OLIGONUCLEOTIDES OPTIMIZED FOR KIDNEY TARGETING

This application claims the benefit of priority to U.S. provisional patent application Ser. No. 60/509,450, filed Oct. 7, 2003 and U.S. provisional patent application Ser. No. 60/517,334, filed Nov. 3, 2003, which are hereby incorporated by reference in their entirety.

FIELD OF THE INVENTION

The present invention provides antisense compounds and methods for modulating the expression of target genes expressed in the kidney. In particular, this invention relates to antisense oligonucleotide compounds optimized for targeting nucleic acid molecules expressed in the kidney. Such compounds are shown herein to efficiently modulate the expression of target genes expressed in the kidney.

BACKGROUND OF THE INVENTION

Efficacy and sequence specific behavior of antisense compounds in biological systems depend upon a variety of factors, which include their resistance to enzymatic degradation, binding affinity for the target, susceptibility to RNase H cleavage when bound to a target mRNA and efficiency of cellular uptake. In order to achieve the proper balance of these features for efficient modulation of target gene expression, chemical modifications are made to the antisense compound. For example, unmodified phosphodiester antisense oligonucleotides are degraded rapidly in biological fluids containing hydrolytic enzymes (Shaw et al., *Nucleic Acids Res.* 1991, 19, 747-750; Woolf et al., *Nucleic Acids Res.* 1990, 18, 1763-1769) and first generation modified antisense compounds (i.e. 2'-deoxyphosphorothioate oligonucleotides) also are subject to activity-limiting degradation (Maier et al., *Biomed. Pept., Proteins Nucleic Acids* 1995, 1, 235-241; Agrawal et al., *Proc. Natl. Acad. Sci. U.S.A.* 1991, 88, 7595-7599). Thus, modifications that render the oligonucleotide more resistant to nuclease activity are desirable in order to enhance antisense activity of the compound. Sugar moieties of antisense compounds also have been modified to increase such properties as lipophilicity, binding affinity for the target mRNA, chemical stability and nuclease resistance.

Distribution to peripheral tissues and ultimate uptake into the cells of target organs also is critical to the effectiveness of antisense compounds for treatment of a wide range of diseases. The highest concentrations of antisense compounds are typically found in the liver, kidney, spleen and lymph nodes, but can be detected in nearly all organs except for the brain (Geary et al., *Curr. Opin. Investig. Drugs,* 2001, 2, 562-573; Geary et al., *J. Pharm. Exp. Therap.,* 2001, 296, 890-897). Despite the ability of current antisense compounds to be delivered to the kidney, there is a need for development of improved antisense compounds that effect target mRNA reduction in the kidney at lower doses and without toxicity.

The kidney is an important target for antisense therapeutics due to its role in controlling many metabolic processes. A number of genes expressed in the kidney have been associated with the development of metabolic disease. Two such examples are the sodium-dependent glucose cotransporter 2 (SGLT2) and connective tissue growth factor (CTGF), both of which have been linked to the development and/or progression of diabetes.

Sodium-Dependent Glucose Cotransporter 2 (SGLT2)

Diabetes is a disorder characterized by hyperglycemia due to deficient insulin action. Chronic hyperglycemia is a major risk factor for diabetes-associated complications, including heart disease, retinopathy, nephropathy and neuropathy. As the kidneys play a major role in the regulation of plasma glucose levels, renal glucose transporters are becoming attractive drug targets (Wright, *Am. J. Physiol. Renal Physiol.,* 2001, 280, F10-18).

Synthetic agents that are derived from phlorizin, a specific inhibitor of sodium/glucose transporters, have been designed and include T-1095, and its metabolically active form T-1095A (Tsujihara et al., *J. Med. Chem.,* 1999, 42, 5311-5324). Phlorizin, T-1095 and T-1095A all inhibited sodium-dependent glucose uptake in brush border membranes prepared from normal and diabetic rat kidney, rat small intestine, mouse kidney and dog kidney, as well as in *Xenopus oocytes* injected with human SGLT mRNA (Oku et al., *Diabetes,* 1999, 48, 1794-1800; Oku et al., *Eur. J. Pharmacol.,* 2000, 391, 183-192). These agents have been tested as antidiabetic compounds in laboratory animals with genetic and streptozotocin-induced diabetes. In these models, administration of these compounds inhibited renal SGLT activity, increased urinary glucose excretion and improved glucose tolerance, hyperglycemia and hypoinsulemia (Arakawa et al., *Br. J. Pharmacol.,* 2001, 132, 578-586; Oku et al., *Diabetes,* 1999, 48, 1794-1800; Oku et al., *Eur. J. Pharmacol.,* 2000, 391, 183-192). Prolonged treatment of db/db mice with T-1095 yielded similar results and also almost completely suppressed the increase of urinary albumin and improved renal glomeruli pathology, indicating a beneficial influence on renal dysfunction and a protective effect against nephropathy, respectively (Arakawa et al., *Br. J. Pharmacol.,* 2001, 132, 578-586). Diabetic nephropathy is the most common cause of end-stage renal disease that develops in many patients with diabetes. In Zucker diabetic fatty rats, long-term treatment with T-1095 lowered both fed and fasting glucose levels to near normal ranges. Also observed were recovered hepatic glucose production and glucose utilization rates without a significant improvement in skeletal muscle glucose utilization rate, indicating that hyperglycemia contributes to insulin resistance in hepatic and adipose tissue in this rat model of diabetes. These results further suggest that glucotoxicity, which results from long-term hyperglycemia, induces tissue-dependent insulin resistance in diabetic patients (Nawano et al., *Am. J. Physiol. Endocrinol. Metab.,* 2000, 278, E535-543).

Other SGLT2 inhibiting compounds are known in the art, such as the c-aryl glucosides disclosed and claimed in U.S. Pat. No. 6,414,126, which are inhibitors of sodium dependent glucose transporters found in the intestine and kidney and are proposed to treat diabetes, hyperglycemia and related diseases when used alone or in combination with other antidiabetic agents (Ellsworth et al., 2002).

The US pre-grant publication 20030055019 claims and discloses isolated mutant proteins selected from a group which includes SGLT2, the corresponding nucleic acid molecules encoding said mutant proteins, isolated antisense derivatives of the nucleic acid sequences encoding said mutant proteins, as well as methods of delivering said antisense nucleic acid derivatives to treat or prevent hypertension, diabetes, insulin sensitivity, obesity, dyslipidemia and stroke. This application also discloses the antisense molecules may be DNA or RNA or a chimeric mixture, single-stranded or double-stranded or may comprise a ribozyme or catalytic RNA (Shimkets, 2003).

The European Patent Applications EP 1 293 569 and EP 1 308 459 claim and disclose a polynucleotide comprising a protein-coding region of the nucleotide sequence of any one of a group of sequences which includes a nucleic acid sequence encoding human SGLT2, an oligonucleotide comprising at least 15 nucleotides complementary to the nucleotide sequence or to a complementary strand thereof and an antisense polynucleotide against the claimed polynucleotide or a part thereof. These applications disclose the use of said antisense polynucleotides for suppressing the expression of a polypeptide of the invention and for gene therapy (Isogai et al., 2003, Isogai et al., 2003).

Although phlorizin and its derivatives are potent inhibitors of sodium-glucose cotransporters, these agents do not specifically inhibit a single species of SGLT, thus all SGLTs in all tissues are affected. Thus, there remains a need for therapeutic compounds that target specific SGLT species. Antisense technology is an effective means for reducing the expression of specific gene products and may therefore prove to be uniquely useful in a number of therapeutic, diagnostic and research applications for the modulation of SGLT2 expression. Furthermore, given the role of SGLT2 in the development of diabetes, antisense compounds with the ability to be delivered to the kidney and specifically inhibit SGLT2 are highly desirable.

Connective Tissue Growth Factor (CTGF)

Connective tissue growth factor (CTGF; also known as ctgrofact, fibroblast inducible secreted protein, fisp-12, NOV2, insulin-like growth factor-binding protein-related protein 2, IGFBP-rP2, IGFBP-8, HBGF-0.8, Hcs24, and ecogenin) is a member of the CCN (CTGF/CYR61/NOV) family of modular proteins, named for the first family members identified, connective tissue growth factor, cysteine-rich (CYR61), and nephroblastoma overexpressed (NOV), but the family also includes the proteins ELM-1 (expressed in low-metastatic cells), WISP-3 (Wnt-1-induced secreted protein), and COP-1 (WISP-2). CCN proteins have been found to be secreted, extracellular matrix-associated proteins that regulate cellular processes such as adhesion, migration, mitogenesis, differentiation, survival, angiogenesis, atherosclerosis, chondrogenesis, wound healing, tumorigenesis, and vascular and fibrotic diseases like scleroderma (Laui and Lam, *Exp. Cell Res.*, 1999, 248, 44-57).

Connective tissue growth factor is expressed in fibroblasts during normal differentiation processes that involve extracellular matrix (ECM) production and remodeling, such as embryogenesis and uterine decidualization following implantation. Connective tissue growth factor is also frequently overexpressed in fibrotic skin disorders such as systemic sclerosis, localized skin sclerosis, keloids, scar tissue, eosinophilic fasciitis, nodular fasciitis, and Dupuytren's contracture. Connective tissue growth factor mRNA or protein levels are elevated in fibrotic lesions of major organs and tissues including the liver, kidney, lung, cardiovascular system, pancreas, bowel, eye, and gingiva. In mammary, pancreatic and fibrohistiocytic tumors characterized by significant connective tissue involvement, connective tissue growth factor is overexpressed in the stromal compartment. In many cases, connective tissue growth factor expression is linked spatially and temporally to the profibrogenic cytokine transforming growth factor-beta (TGF-β) (Moussad and Brigstock, *Mol. Genet. Metab.*, 2000, 71, 276-292).

Expansion of ECM with fibrosis occurs in many tissues as part of the end-organ complications of diabetes (i.e. diabetic nephropathy), and advanced glycosylation end products (AGE) are implicated as one causitive factor in diabetic tissue fibrosis. In addition to being a potent inducer of ECM synthesis and angiogenesis, connective tissue growth factor is increased in tissues from rodent models of diabetes. AGE treatment of primary cultures of CRL-2097 and CRL-1474 nonfetal human dermal fibroblasts resulted in an increase in steady state levels of connective tissue growth factor mRNA as well as protein levels in conditioned medium and cell-associated connective tissue growth factor, while other IGFBP-related proteins were not upregulated by AGE. Thus, AGE upregulates the profibrotic and proangiogenic protein connective tissue growth factor, which may play a role in diabetic complications (Twigg et al., *Endocrinology*, 2001, 142, 1760-1769).

Connective tissue growth factor has been associated with the development of diabetes-related conditions, including diabetic nephropathy. Diabetic nephropathy is a common complication in patients with either type 1 or type 2 diabetes mellitus and is recognized to cause severe morbidity and mortality. Structural hallmarks of advanced diabetic nephropathy are glomerulosclerosis and tubulointerstitial fibrosis leading to kidney failure. Current therapies include ACE inhibitors and angiotensin II receptor blockers, both of which are not justified for blanket use among all newly diagnosed patients since only 30-40% will develop progressive renal disease and the long term side effects of these drugs are unknown.

In addition to the need for safe and effective treatments for diabetes is a need for a reliable method to accurately predict, at early stages of disease, which diabetic patients will develop nephropathy and progress to kidney failure. Persistent microalbuminuria is regarded as a predictor of established vascular damage and an indicator of incipient nephropathy. Studies of renal biopsies from patients with type 1 diabetic nephropathy demonstrate an increase in expression of CTGF in renal tissue exhibiting microalbuminuria and nephropathy, relative to normal control tissues (Adler et al., Kidney Int., 2001, 60, 2330-2336), suggesting CTGF is not only a mediator of diabetic nephropathy, but could be used as a marker for the development of disease (Riser et al., *Kidney Int.*, 2003, 64, 451-458).

Disclosed and claimed in U.S. Pat. No. 5,876,730 is a substantially pure or isolated polypeptide characterized as having an amino acid sequence corresponding to the carboxy terminal amino acids of a connective tissue growth factor (CTGF) protein, wherein the polypeptide has an amino acid sequence beginning at amino acid residue 247 or 248 from the N-terminus of connective tissue growth factor, an isolated polynucleotide sequence encoding the connective tissue growth factor polypeptide, a recombinant expression vector which contains said polynucleotide, a host cell containing said expression vector, and a pharmaceutical composition comprising a therapeutically effective amount of connective tissue growth factor polypeptide in a pharmaceutically acceptable carrier. Antisense oligonucleotides are generally disclosed (Brigstock and Harding, 1999).

Disclosed and claimed in U.S. Pat. Nos. 5,783,187; 5,585,270; 6,232,064; 6,150,101; 6,069,006 and PCT Publication WO 00/35936 are an isolated polynucleotide encoding the connective tissue growth factor polypeptide, expression vectors, host cells stably transformed or transfected with said vectors; an isolated polynucleotide comprising 5' untranslated regulatory nucleotide sequences isolated from upstream of connective tissue growth factor, wherein said untranslated regulatory nucleotide sequences comprises a transcriptional and translational initiation region and wherein said sequence is a TGF-beta responsive element; an isolated nucleic acid construct comprising a non-coding regulatory sequence isolated upstream from a connective tissue growth factor (CTGF) gene, wherein said non-coding regulatory sequence is operably associated with a nucleic acid sequence which expresses a protein of interest or antisense RNA, wherein said nucleic acid sequence is heterologous to said non-coding sequence; and a fragment of connective tissue growth factor (CTGF) polypeptide having the ability to induce ECM synthesis, collagen synthesis and/or myofibroblast differentiation, comprising an amino acid sequence encoded by at least exon 2 or exon 3 of said polypeptide. Further claimed is a method for identifying a composition which affects TGF-beta-induced connective tissue growth factor expression, and a method of diagnosing a pathological state in a subject suspected of having a pathology selected from the group consisting of fibrotic disease and atherosclerosis, the method comprising obtaining a sample suspected of containing connective tissue growth factor, whereby detecting a difference in the level of connective tissue growth factor in the sample from the subject as compared to the level of connective tissue growth factor in the normal standard sample is diagnostic of a pathology characterized by a cell proliferative disorder associated with connective tissue growth factor in the subject. Further claimed is a method for ameliorating a cell proliferative disorder associated with connective tissue growth factor, comprising administering to a subject having said disorder, at the site of the disorder, a composition comprising a therapeutically effective amount of an antibody or fragment thereof that binds to connective tissue growth factor, wherein said antibody or fragment thereof does not bind to PDGF. Antisense oligonucleotides are generally disclosed (Grotendorst, 2000; Grotendorst and Bradham, 2001; Grotendorst and Bradham, 2000; Grotendorst and Bradham, 1996; Grotendorst and Bradham, 1998; Grotendorst and Bradham, 2000).

Disclosed and claimed in PCT Publication WO 99/66959 is a device for promoting neuronal regeneration, comprising a gene activated matrix comprising a biocompatible matrix and at least one neuronal therapeutic encoding agent having an operably linked promoter device, wherein the neuronal therapeutic encoding agent encodes an inhibitor of neuronal cell growth, and wherein the inhibitor of neuronal cell growth is selected from the group consisting of NFB42, TGF-beta, connective tissue growth factor (CTGF), and macrophage migration inhibitory factor (MIF), and wherein the neuronal therapeutic encoding agent is selected from the group consisting of a nucleic acid molecule, a vector, an antisense nucleic acid molecule and a ribozyme (Baird et al., 1999).

Disclosed and claimed in PCT Publication WO 00/27868 is a substantially pure connective tissue growth factor polypeptide or functional fragments thereof, an isolated polynucleotide sequence encoding said polypeptide, said polynucleotide sequence wherein T can also be U, a nucleic acid sequence complementary to said polynucleotide sequence, and fragments of said sequences that are at least 15 bases in length and that will hybridize to DNA which encodes the amino acid sequence of the connective tissue growth factor protein under moderate to highly stringent conditions. Further claimed is an expression vector including said polynucleotide, a host cell stably transformed with said vector, an antibody that binds to said polypeptide, and a method for producing said polypeptide. Further claimed is a method for inhibiting the expression of connective tissue growth factor in a cell comprising contacting the cell with a polynucleotide which binds to a target nucleic acid in the cell, wherein the polynucleotide inhibits the expression of connective tissue growth factor in the cell, wherein the polynucleotide is an antisense polynucleotide, as well as a kit for the detection of connective tissue growth factor expression comprising a carrier means being compartmentalized to receive one or more containers, comprising at least one container containing at least one antisense oligonucleotide that binds to connective tissue growth factor (Schmidt et al., 2000).

Disclosed and claimed in PCT Publication WO 00/13706 is a method for treating or preventing fibrosis, the method comprising administering to a subject in need an effective amount of an agent that modulates, regulates or inhibits the expression or activity of connective tissue growth factor or fragments thereof, and wherein the agent is an antibody, an antisense oligonucleotide, or a small molecule. The method is directed to treating kidney fibrosis and associated renal disorders, in particular, complications associated with diabetes and hypertension (Riser and Denichili, 2000).

Disclosed and claimed in PCT Publication WO 01/29217 is an isolated nucleic acid molecule comprising a nucleic acid sequence encoding a polypeptide comprising an amino acid sequence selected from a group comprising NOV1, NOV2 (connective tissue growth factor), and NOV3, a mature form or variant of an amino acid sequence selected from said group, as well as a nucleic acid molecule comprising a nucleic acid sequence encoding a polypeptide comprising an amino acid sequence selected from said group as well as mature and variant forms or fragments of said polypeptides, and the complement of said nucleic acid molecule. Antisense oligonucleotides are generally disclosed (Prayaga et al., 2001).

A phosphorothioate antisense oligonucleotide, 16 nucleotides in length and targeted to the translation initiation start site, was used to inhibit expression of connective tissue growth factor and suppress proliferation and migration of bovine aorta vascular endothelial cells in culture (Shimo et al., *J. Biochem.* (*Tokyo*), 1998, 124, 130-140). This antisense oligonucleotide was also used to show that connective tissue growth factor induces apoptosis in MCF-7 human breast cancer cells and that TGF-beta-induced apoptosis is mediated, in part, by connective tissue growth factor (Hishikawa et al., *J. Biol. Chem.*, 1999, 274, 37461-37466). The same antisense oligonucleotide was also found to inhibit the TGF-beta-mediated activation of caspase 3 and thus to inhibit induction of TGF-beta-mediated apoptosis in human aortic smooth muscle cells (HASC) (Hishikawa et al., *Eur. J. Pharmacol.*, 1999, 385, 287-290). This antisense oligonucleotide was also used to block connective tissue growth factor expression and demonstrate that high blood pressure upregulates expression of connective tissue growth factor in mesangial cells, which in turn enhances ECM protein production and induces apoptosis, contributing to the remodeling of mesangium and ultimately glomerulosclerosis (Hishikawa et al., *J. Biol. Chem.*, 2001, 276, 16797-16803).

Currently, there are no known therapeutic agents that effectively inhibit the synthesis of connective tissue growth factor and thus far. Consequently, there remains a long felt need for additional agents capable of effectively inhibiting connective tissue growth factor function, which for the treatment of diseases like diabetes, requires compounds that can be effectively delivered to the kidney.

Antisense technology is emerging as an effective means for reducing the expression of specific gene products and may therefore prove to be uniquely useful in a number of therapeutic, diagnostic, and research applications for the modulation of connective tissue growth factor expression.

The present invention provides antisense compounds and methods for optimized kidney targeting as well as methods for preventing diseases and conditions associated with expression of selected target genes in the kidney. Further provided are compounds and methods for modulating blood glucose levels and for inhibiting the development of diabetic nephropathy. Also provided are compounds and methods for modulating SGLT2 and CTGF expression in kidney cells and tissues.

SUMMARY OF THE INVENTION

The present invention is directed to antisense compounds that are optimized for modulating expression of target genes in the kidney. Provided are methods of enhancing antisense inhibition of expression of preselected cellular RNA targets in kidney cells and kidney tissue using antisense compounds of the invention. Also provided are methods of preventing or delaying the onset of a disease or condition in an animal, wherein said disease or condition is associated with expression of a preselected cellular RNA target, particularly SGLT2 or CTGF. Methods of lowering blood glucose levels in an animal and methods of delaying or preventing the onset of diabetic nephropathy also are set forth herein. Such methods comprise administering a therapeutically or prophylactically effective amount of one or more of the compounds of the invention to the animal in need of treatment. Provided herein are methods of enhancing antisense inhibition of expression of SGLT2 in kidney cells or kidney tissues, comprising contacting said cells or tissues with one or more of the compounds of the invention. Also provided are methods of enhancing antisense inhibition of expression of CTGF in kidney cells or kidney tissues, comprising contacting said cells or tissues with one or more of the compounds of the invention.

DETAILED DESCRIPTION OF THE INVENTION

A. Overview of the Invention

In accordance with the present invention, oligomeric compounds that efficiently modulate expression of target genes in the kidney are provided. The oligomeric compounds of the invention are chimeric oligonucleotides having mixed phosphorothioate and phosphodiester backbones, referred to herein as "mixed backbone compounds." Preferably, the compounds of the invention have a central "gap" region consisting of at least 5 contiguous 2'-deoxy nucleosides flanked by two "wing" regions consisting of at least one 2'-O-methoxyethyl nucleoside in each region. The internucleoside linkages of the preferred compounds are phosphorothioate linkages in the central "gap" region and phosphodiester linkages in the two "wing" regions. In another embodiment, mixed backbone compounds have phosphodiester linkages in the "wing" regions except for one phosphodiester linkage at one or both of the extreme 5' and 3' ends of the oligonucleotide.

It is shown herein that mixed backbone compounds are efficiently delivered to the kidney and treatment with the mixed backbone compounds results in efficient modulation of target gene expression in the kidney without liver or kidney toxicity. It is further shown herein that treatment with mixed backbone compounds in mouse models of type 2 diabetes reduces blood glucose levels and the development of diabetic nephropathy. Data from two molecular targets are provided as illustrations of the invention.

As used herein, the terms "target nucleic acid" and "nucleic acid molecule encoding the target gene" have been used for convenience to encompass DNA encoding the target gene, RNA (including pre-mRNA and mRNA or portions thereof) transcribed from such DNA, and also cDNA derived from such RNA. The hybridization of a compound of this invention with its target nucleic acid is generally referred to as "antisense". Consequently, the preferred mechanism believed to be included in the practice of some preferred embodiments of the invention is referred to herein as "antisense inhibition." Such antisense inhibition is typically based upon hydrogen bonding-based hybridization of oligonucleotide strands or segments such that at least one strand or segment is cleaved, degraded, or otherwise rendered inoperable. In this regard, it is presently preferred to target specific nucleic acid molecules and their functions for such antisense inhibition.

The present invention describes chemically modified antisense oligonucleotides that are optimized for targeting the kidney. As used herein, "optimize" means to modify in order to achieve maximum efficiency. In the context of the present invention, optimized antisense compounds are those that are efficiently delivered to the kidney and result in inhibition of target gene mRNA expression in the kidney while causing minimal toxicity.

The functions of DNA to be interfered with can include replication and transcription. Replication and transcription, for example, can be from an endogenous cellular template, a vector, a plasmid construct or otherwise. The functions of RNA to be interfered with can include functions such as translocation of the RNA to a site of protein translation, translocation of the RNA to sites within the cell which are distant from the site of RNA synthesis, translation of protein from the RNA, splicing of the RNA to yield one or more RNA species, and catalytic activity or complex formation involving the RNA which may be engaged in or facilitated by the RNA. One preferred result of such interference with target nucleic acid function is modulation of the expression of target genes in the kidney. In the context of the present invention, "modulation" and "modulation of expression" mean either an increase (stimulation) or a decrease (inhibition) in the amount or levels of a nucleic acid molecule encoding the gene, e.g., DNA or RNA. Inhibition is often the preferred form of modulation of expression and mRNA is often a preferred target nucleic acid.

In the context of this invention, "hybridization" means the pairing of complementary strands of oligomeric compounds. In the present invention, the preferred mechanism of pairing involves hydrogen bonding, which may be Watson-Crick, Hoogsteen or reversed Hoogsteen hydrogen bonding, between complementary nucleoside or nucleotide bases (nucleobases) of the strands of oligomeric compounds. For example, adenine and thymine are complementary nucleobases which pair through the formation of hydrogen bonds. Hybridization can occur under varying circumstances.

An antisense compound is specifically hybridizable when binding of the compound to the target nucleic acid interferes with the normal function of the target nucleic acid to cause a loss of activity, and there is a sufficient degree of complementarity to avoid non-specific binding of the antisense compound to non-target nucleic acid sequences under conditions in which specific binding is desired, i.e., under physiological conditions in the case of in vivo assays or therapeutic treatment, and under conditions in which assays are performed in the case of in vitro assays.

In the present invention the phrase "stringent hybridization conditions" or "stringent conditions" refers to conditions under which a compound of the invention will hybridize to its target sequence, but to a minimal number of other sequences. Stringent conditions are sequence-dependent and will be different in different circumstances and in the context of this invention, "stringent conditions" under which oligomeric compounds hybridize to a target sequence are determined by the nature and composition of the oligomeric compounds and the assays in which they are being investigated.

"Complementary," as used herein, refers to the capacity for precise pairing between two nucleobases of an oligomeric compound. For example, if a nucleobase at a certain position of an oligonucleotide (an oligomeric compound), is capable of hydrogen bonding with a nucleobase at a certain position of a target nucleic acid, said target nucleic acid being a DNA, RNA, or oligonucleotide molecule, then the position of hydrogen bonding between the oligonucleotide and the target nucleic acid is considered to be a complementary position.

The oligonucleotide and the DNA, RNA, or oligonucleotide molecule are complementary to each other when a sufficient number of complementary positions in each molecule are occupied by nucleobases which can hydrogen bond with each other. Thus, "specifically hybridizable" and "complementary" are terms which are used to indicate a sufficient degree of precise pairing or complementarity over a sufficient number of nucleobases such that stable and specific binding occurs between the oligonucleotide and a target nucleic acid.

It is understood in the art that the sequence of an antisense compound need not be 100% complementary to that of its target nucleic acid to be specifically hybridizable. Moreover, an oligonucleotide may hybridize over one or more segments such that intervening or adjacent segments are not involved in the hybridization event (e.g., a loop structure, mismatch or hairpin structure). It is preferred that the antisense compounds of the present invention comprise at least 70%, or at least 75%, or at least 80%, or at least 85% sequence complementarity to a target region within the target nucleic acid, more preferably that they comprise at least 90% sequence complementarity and even more preferably comprise at least 95% or at least 99% sequence complementarity to the target region within the target nucleic acid sequence to which they are targeted. For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., *J. Mol. Biol.*, 1990, 215, 403-410; Zhang and Madden, *Genome Res.*, 1997, 7, 649-656).

Percent homology, sequence identity or complementarity, can be determined by, for example, using the default settings of the Gap program (Wisconsin Sequence Analysis Package, Version 8 for Unix, Genetics Computer Group, University Research Park, Madison Wis.), which uses the algorithm of Smith and Waterman (Adv. Appl. Math., 1981, 2, 482-489). In some preferred embodiments, homology, sequence identity or complementarity, between the oligomeric compound and target is between about 50% to about 60%. In some embodiments, homology, sequence identity or complementarity, is between about 60% to about 70%. In preferred embodiments, homology, sequence identity or complementarity, is between about 70% and about 80%. In more preferred embodiments, homology, sequence identity or complementarity, is between about 80% and about 90%. In some preferred embodiments, homology, sequence identity or complementarity, is about 90%, about 92%, about 94%, about 95%, about 96%, about 97%, about 98%, about 99% or about 100%.

B. Compounds of the Invention

The antisense compounds of the present invention include modified compounds in which a different base is present at one or more of the nucleotide positions in the compound. For example, if the first nucleotide is an adenosine, modified compounds may be produced which contain thymidine, guanosine or cytidine at this position. This may be done at any of the positions of the antisense compound. These compounds are then tested using the methods described herein to determine their ability to inhibit expression of target gene mRNA.

In the context of this invention, the term "oligomeric compound" refers to a polymer or oligomer comprising a plurality of monomeric units. In the context of this invention, the term "oligonucleotide" refers to an oligomer or polymer of ribonucleic acid (RNA) or deoxyribonucleic acid (DNA) or mimetics, chimeras, analogs and homologs thereof. This term includes oligonucleotides composed of naturally occurring nucleobases, sugars and covalent internucleoside (backbone) linkages as well as oligonucleotides having non-naturally occurring portions which function similarly. Such modified or substituted oligonucleotides are often preferred over native forms because of desirable properties such as, for example, enhanced cellular uptake, enhanced affinity for a target nucleic acid and increased stability in the presence of nucleases.

The antisense compounds in accordance with this invention preferably comprise from about 8 to about 80 nucleobases (i.e. from about 8 to about 80 linked nucleosides). One of ordinary skill in the art will appreciate that the invention embodies compounds of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 nucleobases in length.

In one preferred embodiment, the antisense compounds of the invention are 10 to 50 nucleobases in length. One having ordinary skill in the art will appreciate that this embodies compounds of 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49 or 50 nucleobases in length.

In another preferred embodiment, the antisense compounds of the invention are 13 to 30 nucleobases in length. One having ordinary skill in the art will appreciate that this embodies compounds of 13, 14, 15, 16, 17, 18, 19, 20, 21, 22, 23, 24, 25, 26, 27, 28, 29 or 30 nucleobases in length.

In another preferred embodiment, the antisense compounds of the invention are 15 to 25 nucleobases in length. One having ordinary skill in the art will appreciate that this embodies compounds of 15, 16, 17, 18, 19, 20, 21, 22, 23, 24 or 25 nucleobases in length.

In another preferred embodiment, the antisense compounds of the invention are 18 to 22 nucleobases in length. One having ordinary skill in the art will appreciate that this embodies compounds of 18, 19, 20, 21 or 22 nucleobases in length.

Particularly preferred compounds are oligonucleotides from about 10 to about 50 nucleobases, preferably those comprising from about 13 to about 30 nucleobases, more preferably those comprising from about 15 to about 25, and most preferred from about 18 to about 22 nucleobases.

Antisense compounds are commonly used as research reagents and diagnostics. For example, antisense oligonucleotides, which are able to inhibit gene expression with exquisite specificity, are often used by those of ordinary skill to elucidate the function of particular genes. Antisense compounds are also used, for example, to distinguish between functions of various members of a biological pathway. Antisense modulation has, therefore, been harnessed for research use.

The specificity and sensitivity of antisense is also harnessed by those of skill in the art for therapeutic uses. Antisense compounds are employed as therapeutic moieties in the treatment of disease states in animals, including humans. Antisense oligonucleotide drugs have been safely and effectively administered to humans and numerous clinical trials are presently underway. It is thus established that antisense compounds are useful therapeutic modalities that can be configured to be useful in treatment regimes for the treatment of cells, tissues and animals, especially humans.

In one embodiment, the antisense compounds of the invention are targeted to genes expressed in the kidney that have been associated with a disease or disorder. Such diseases and/or disorders include, but are not limited to, metabolic diseases, such as type 1 or type 2 diabetes. Target genes include, but are not limited to, SGLT2 and connective tissue growth factor.

The antisense compounds of the invention can be utilized in pharmaceutical compositions by adding an effective amount of a compound to a suitable pharmaceutically acceptable diluent or carrier. Use of the compounds and methods of the invention may also be useful prophylactically.

C. Modifications

As is known in the art, a nucleoside is a base-sugar combination. The base portion of the nucleoside is normally a heterocyclic base sometimes referred to as a "nucleobase" or simply a "base". The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2',3' or 5' hydroxyl moiety of the sugar. In forming oligonucleotides, the phosphate groups covalently link adjacent nucleosides to one another to form a linear polymeric compound. In turn, the respective ends of this linear polymeric compound can be further joined to form a circular compound, however, linear compounds are generally preferred. In addition, linear compounds may have internal nucleobase complementarity and may therefore fold in a manner as to produce a fully or partially double-stranded compound. Within oligonucleotides, the phosphate groups are commonly referred to as forming the internucleoside backbone of the oligonucleotide. The normal linkage or backbone of RNA and DNA is a 3' to 5' phosphodiester linkage.

Chimeric Compounds

The present invention includes antisense compounds which are chimeric compounds. "Chimeric" antisense compounds or "chimeras," in the context of this invention, are antisense compounds, particularly oligonucleotides, which contain two or more chemically distinct regions, each made up of at least one monomer unit (i.e., a nucleotide). Antisense compounds of the present invention are chimeric oligonucleotides with a central "gap" region containing 2'-deoxy nucleosides flanked by two "wing" regions containing 2'-O-methoxyethyl nucleosides. The oligomeric compounds have a mixed backbone of phosphorothioate linkages in the central "gap" region and phosphodiester linkages in the flanking "wing" regions. Mixed backbone compounds of the invention may also contain one phosphorothioate linkage at one or both of the extreme 5' or 3' ends of the oligonucleotide.

Oligonucleotides such as these are also known in the art as "gapmers" or gapped oligonucleotides. In a gapmer that is 20 nucleotides in length, a gap or wing can be 1, 2, 3, 4, 5, 6, 7, 8, 9, 10, 11, 12, 13, 14, 15, 16, 17 or 18 nucleotides in length.

In one embodiment, a 20-nucleotide gapmer is comprised of a gap 8 nucleotides in length, flanked on both the 5' and 3' sides by wings 6 nucleotides in length. In another embodiment, a 20-nucleotide gapmer is comprised of a gap 10 nucleotides in length, flanked on both the 5' and 3' sides by wings 5 nucleotides in length. In another embodiment, a 20-nucleotide gapmer is comprised of a gap 12 nucleotides in length flanked on both the 5' and 3' sides by wings 4 nucleotides in length. In a further embodiment, a 20-nucleotide gapmer is comprised of a gap 14 nucleotides in length flanked on both the 5' and 3' sides by wings 3 nucleotides in length. In another embodiment, a 20-nucleotide gapmer is comprised of a gap 16 nucleotides in length flanked on both the 5' and 3' sides by wings 2 nucleotides in length. In a further embodiment, a 20-nucleotide gapmer is comprised of a gap 18 nucleotides in length flanked on both the 5' and 3' ends by wings 1 nucleotide in length. Alternatively, the wings are of different lengths, for example, a 20-nucleotide gapmer may be comprised of a gap 10 nucleotides in length, flanked by a 6-nucleotide wing on one side (5' or 3') and a 4-nucleotide wing on the other side (5' or 3'). Antisense oligonucleotides with greater than or less than 20 nucleotides are also contemplated. One of skill in the art can select an appropriate number of nucleotides for the gap and wing regions in accordance with the present invention.

Representative U.S. patents that teach the preparation of such hybrid structures include, but are not limited to, U.S. Pat. Nos. 5,013,830; 5,149,797; 5,220,007; 5,256,775; 5,366,878; 5,403,711; 5,491,133; 5,565,350; 5,623,065; 5,652,355; 5,652,356; and 5,700,922, certain of which are commonly owned with the instant application, and each of which is herein incorporated by reference in its entirety.

Natural and Modified Nucleobases

Antisense compounds of the invention may include nucleobase (often referred to in the art as heterocyclic base or simply as "base") modifications or substitutions. As used herein, "unmodified" or "natural" nucleobases include the purine bases adenine (A) and guanine (G), and the pyrimidine bases thymine (T), cytosine (C) and uracil (U). Modified nucleobases include other synthetic and natural nucleobases such as 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($-C{\equiv}C-CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified nucleobases include tricyclic pyrimidines such as phenoxazine cytidine(1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido [5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deazaadenine, 7-deazaguanosine, 2-aminopyridine and 2-pyridone. Further nucleobases include those disclosed in U.S. Pat. No. 3,687,808, those disclosed in *The*

*Concise Encyclopedia Of Polymer Science And Engineering*, pages 858-859, Kroschwitz, J. I., ed. John Wiley & Sons, 1990, those disclosed by Englisch et al., *Angewandte Chemie, International Edition*, 1991, 30, 613, and those disclosed by Sanghvi, Y. S., Chapter 15, *Antisense Research and Applications*, pages 289-302, Crooke, S. T. and Lebleu, B., ed., CRC Press, 1993. Certain of these nucleobases are particularly useful for increasing the binding affinity of the compounds of the invention. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. and are presently preferred base substitutions, even more particularly when combined with 2'-O-methoxyethyl sugar modifications.

Representative U.S. patents that teach the preparation of certain of the above noted modified nucleobases as well as other modified nucleobases include, but are not limited to, the above noted U.S. Pat. No. 3,687,808, as well as U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; and 5,681,941, certain of which are commonly owned with the instant application, and each of which is herein incorporated by reference, and U.S. Pat. No. 5,750,692, which is commonly owned with the instant application and also herein incorporated by reference.

Conjugates

Another modification of the antisense compounds of the invention involves chemically linking to the antisense compound one or more moieties or conjugates which enhance the activity, cellular distribution or cellular uptake of the oligonucleotide. These moieties or conjugates can include conjugate groups covalently bound to functional groups such as primary or secondary hydroxyl groups. Conjugate groups of the invention include intercalators, reporter molecules, polyamines, polyamides, polyethylene glycols, polyethers, groups that enhance the pharmaco-dynamic properties of oligomers, and groups that enhance the pharmacokinetic properties of oligomers. Typical conjugate groups include cholesterols, lipids, phospho-lipids, biotin, phenazine, folate, phenanthridine, anthraquinone, acridine, fluoresceins, rhodamines, coumarins, and dyes. Groups that enhance the pharmacodynamic properties, in the context of this invention, include groups that improve uptake, enhance resistance to degradation, and/or strengthen sequence-specific hybridization with the target nucleic acid. Groups that enhance the pharmacokinetic properties, in the context of this invention, include groups that improve uptake, distribution, metabolism or excretion of the compounds of the present invention. Representative conjugate groups are disclosed in International Patent Application PCT/US92/09196, filed Oct. 23, 1992, and U.S. Pat. No. 6,287,860, the entire disclosures of which are incorporated herein by reference. Conjugate moieties include but are not limited to lipid moieties such as a cholesterol moiety, cholic acid, a thioether, e.g., hexyl-S-tritylthiol, a thiocholesterol, an aliphatic chain, e.g., dodecandiol or undecyl residues, a phospholipid, e.g., di-hexadecyl-rac-glycerol or triethyl-ammonium 1,2-di-O-hexadecyl-rac-glycero-3-H-phosphonate, a polyamine or a polyethylene glycol chain, or adamantane acetic acid, a palmityl moiety, or an octadecylamine or hexylamino-carbonyl-oxycholesterol moiety. Antisense compounds of the invention may also be conjugated to active drug substances, for example, aspirin, warfarin, phenyl-butazone, ibuprofen, suprofen, fenbufen, ketoprofen, (S)-(+)-pranoprofen, carprofen, dansylsarcosine, 2,3,5-triiodo-benzoic acid, flufenamic acid, folinic acid, a benzothiadiazide, chlorthiazide, a diazepine, indo-methicin, a barbiturate, a cephalosporin, a sulfa drug, an antidiabetic, an antibacterial or an antibiotic. Oligonucleotide-drug conjugates and their preparation are described in U.S. patent application Ser. No. 09/334,130 (filed Jun. 15, 1999) which is incorporated herein by reference in its entirety.

Representative U.S. patents that teach the preparation of such oligonucleotide conjugates include, but are not limited to, U.S. Pat. Nos. 4,828,979; 4,948,882; 5,218,105; 5,525,465; 5,541,313; 5,545,730; 5,552,538; 5,578,717, 5,580,731; 5,580,731; 5,591,584; 5,109,124; 5,118,802; 5,138,045; 5,414,077; 5,486,603; 5,512,439; 5,578,718; 5,608,046; 4,587,044; 4,605,735; 4,667,025; 4,762,779; 4,789,737; 4,824,941; 4,835,263; 4,876,335; 4,904,582; 4,958,013; 5,082,830; 5,112,963; 5,214,136; 5,082,830; 5,112,963; 5,214,136; 5,245,022; 5,254,469; 5,258,506; 5,262,536; 5,272,250; 5,292,873; 5,317,098; 5,371,241; 5,391,723; 5,416,203, 5,451,463; 5,510,475; 5,512,667; 5,514,785; 5,565,552; 5,567,810; 5,574,142; 5,585,481; 5,587,371; 5,595,726; 5,597,696; 5,599,923; 5,599,928 and 5,688,941, certain of which are commonly owned with the instant application, and each of which is herein incorporated by reference.

Oligomeric compounds used in the compositions of the present invention can also be modified to have one or more stabilizing groups that are generally attached to one or both termini of oligomeric compounds to enhance properties such as for example nuclease stability. Included in stabilizing groups are cap structures. By "cap structure or terminal cap moiety" is meant chemical modifications, which have been incorporated at either terminus of oligonucleotides (see for example Wincott et al., WO 97/26270, incorporated by reference herein). These terminal modifications protect the oligomeric compounds having terminal nucleic acid molecules from exonuclease degradation, and can help in delivery and/or localization within a cell. The cap can be present at the 5'-terminus (5'-cap) or at the 3'-terminus (3'-cap) or can be present on both termini. In non-limiting examples, the 5'-cap includes inverted a basic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3'-phosphate; 3'-phosphorothioate; phosphorodithioate; or bridging or non-bridging methylphosphonate moiety (for more details see Wincott et al., International PCT publication No. WO 97/26270, incorporated by reference herein).

Particularly preferred 3'-cap structures of the present invention include, for example 4',5'-methylene nucleotide; 1-(beta-D-erythrofuranosyl) nucleotide; 4'-thio nucleotide, carbocyclic nucleotide; 5'-amino-alkyl phosphate; 1,3-di-amino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino;

bridging and/or non-bridging 5'-phosphoramidate, phosphorothioate and/or phosphorodithioate, bridging or non bridging methylphosphonate and 5'-mercapto moieties (for more details see Beaucage and Tyer, 1993, Tetrahedron 49, 1925; incorporated by reference herein).

Further 3' and 5'-stabilizing groups that can be used to cap one or both ends of an oligomeric compound to impart nuclease stability include those disclosed in WO 03/004602 published on Jan. 16, 2003.

D. Formulations

The compounds of the invention may also be admixed, encapsulated, conjugated or otherwise associated with other molecules, molecule structures or mixtures of compounds, as for example, liposomes, receptor-targeted molecules, oral, rectal, topical or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds of the invention encompass any pharmaceutically acceptable salts, esters, or salts of such esters, or any other compound which, upon administration to an animal, including a human, is capable of providing (directly or indirectly) the biologically active metabolite or residue thereof.

The term "pharmaceutically acceptable salts" refers to physiologically and pharmaceutically acceptable salts of the compounds of the invention: i.e., salts that retain the desired biological activity of the parent compound and do not impart undesired toxicological effects thereto. For oligonucleotides, preferred examples of pharmaceutically acceptable salts and their uses are further described in U.S. Pat. No. 6,287,860, which is incorporated herein in its entirety.

The present invention also includes pharmaceutical compositions and formulations which include the antisense compounds of the invention. The pharmaceutical compositions of the present invention may be administered in a number of ways depending upon whether local or systemic treatment is desired and upon the area to be treated. Administration may be topical (including ophthalmic and to mucous membranes including vaginal and rectal delivery), pulmonary, e.g., by inhalation or insufflation of powders or aerosols, including by nebulizer; intratracheal, intranasal, epidermal and transdermal), oral or parenteral. Parenteral administration includes intravenous, intraarterial, subcutaneous, intraperitoneal or intramuscular injection or infusion; or intracranial, e.g., intrathecal or intraventricular, administration. Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogenous systems of one liquid dispersed in another in the form of droplets usually exceeding 0.1 μm in diameter. Emulsions may contain additional components in addition to the dispersed phases, and the active drug which may be present as a solution in either the aqueous phase, oily phase or itself as a separate phase. Microemulsions are included as an embodiment of the present invention. Emulsions and their uses are well known in the art and are further described in U.S. Pat. No. 6,287,860, which is incorporated herein in its entirety.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Examples of sterically stabilized liposomes are those in which part of the vesicle-forming lipid portion of the liposome comprises one or more glycolipids or is derivatized with one or more hydrophilic polymers, such as a polyethylene glycol (PEG) moiety. Liposomes and their uses are further described in U.S. Pat. No. 6,287,860, which is incorporated herein in its entirety.

The pharmaceutical formulations and compositions of the present invention may also include surfactants. The use of surfactants in drug products, formulations and in emulsions is well known in the art. Surfactants and their uses are further described in U.S. Pat. No. 6,287,860, which is incorporated herein in its entirety.

In one embodiment, the present invention employs various penetration enhancers to effect the efficient delivery of nucleic acids, particularly oligonucleotides. In addition to aiding the diffusion of non-lipophilic drugs across cell membranes, penetration enhancers also enhance the permeability of lipophilic drugs. Penetration enhancers may be classified as belonging to one of five broad categories, i.e., surfactants, fatty acids, bile salts, chelating agents, and non-chelating non-surfactants. Penetration enhancers and their uses are further described in U.S. Pat. No. 6,287,860, which is incorporated herein in its entirety.

One of skill in the art will recognize that formulations are routinely designed according to their intended use, i.e. route of administration.

Preferred formulations for topical administration include those in which the oligonucleotides of the invention are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

For topical or other administration, oligonucleotides of the invention may be encapsulated within liposomes or may form complexes thereto, in particular to cationic liposomes. Alternatively, oligonucleotides may be complexed to lipids, in particular to cationic lipids. Preferred fatty acids and esters, pharmaceutically acceptable salts thereof, and their uses are further described in U.S. Pat. No. 6,287,860, which is incorporated herein in its entirety. Topical formulations are described in detail in U.S. patent application Ser. No. 09/315,298 filed on May 20, 1999, which is incorporated herein by reference in its entirety.

Compositions and formulations for oral administration include powders or granules, microparticulates, nanoparticulates, suspensions or solutions in water or non-aqueous media, capsules, gel capsules, sachets, tablets or minitablets. Thickeners, flavoring agents, diluents, emulsifiers, dispersing aids or binders may be desirable. Preferred oral formulations are those in which oligonucleotides of the invention are administered in conjunction with one or more penetration enhancers surfactants and chelators. Preferred surfactants include fatty acids and/or esters or salts thereof, bile acids and/or salts thereof. Preferred bile acids/salts and fatty acids and their uses are further described in U.S. Pat. No. 6,287,860, which is incorporated herein in its entirety. Also preferred are combinations of penetration enhancers, for example, fatty acids/salts in combination with bile acids/salts. A particularly preferred combination is the sodium salt of lauric acid, capric acid and UDCA. Further penetration enhancers include polyoxyethylene-9-lauryl ether, polyoxyethylene-20-cetyl ether. Oligonucleotides of the invention may be delivered orally, in granular form including sprayed dried particles, or complexed to form micro or nanoparticles. Oligonucleotide complexing agents and their uses are further described in U.S. Pat. No. 6,287,860, which is incorporated herein in its entirety. Oral formulations for oligonucleotides and their preparation are described in detail in U.S. application Ser. No. 09/108,673 (filed Jul. 1, 1998), U.S. Ser. No. 09/315,298 (filed May 20, 1999) and U.S. Ser. No. 10/071,822, (filed Feb. 8, 2002; published as US2003-0027780), each of which is incorporated herein by reference in their entirety.

Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Oligonucleotides may be formulated for delivery in vivo in an acceptable dosage form, e.g. as parenteral or non-parenteral formulations. Parenteral formulations include intravenous (IV), subcutaneous (SC), intraperitoneal (IP), intravitreal and intramuscular (IM) formulations, as well as formulations for delivery via pulmonary inhalation, intranasal administration, topical administration, etc. Non-parenteral formulations include formulations for delivery via the alimentary canal, e.g. oral administration, rectal administration, intrajejunal instillation, etc. Rectal administration includes administration as an enema or a suppository. Oral administration includes administration as a capsule, a gel capsule, a pill, an elixir, etc.

In some embodiments, an oligonucleotide may be administered to a subject via an oral route of administration. The subject may be an animal or a human (man). An animal subject may be a mammal, such as a mouse, a rat, a dog, a guinea pig, a monkey, a non-human primate, a cat or a pig. Non-human primates include monkeys and chimpanzees. A suitable animal subject may be an experimental animal, such as a mouse, rat, mouse, a rat, a dog, a monkey, a non-human primate, a cat or a pig.

In some embodiments, the subject may be a human. In certain embodiments, the subject may be a human patient in need of therapeutic treatment as discussed in more detail herein. In certain embodiments, the subject may be in need of modulation of expression of one or more genes as discussed in more detail herein. In some particular embodiments, the subject may be in need of inhibition of expression of one or more genes as discussed in more detail herein. In particular embodiments, the subject may be in need of modulation, i.e. inhibition or enhancement, of HIF1-beta in order to obtain therapeutic indications discussed in more detail herein.

In some embodiments, non-parenteral (e.g. oral) oligonucleotide formulations according to the present invention result in enhanced bioavailability of the oligonucleotide. In this context, the term "bioavailability" refers to a measurement of that portion of an administered drug which reaches the circulatory system (e.g. blood, especially blood plasma) when a particular mode of administration is used to deliver the drug. Enhanced bioavailability refers to a particular mode of administration's ability to deliver oligonucleotide to the peripheral blood plasma of a subject relative to another mode of administration. For example, when a non-parenteral mode of administration (e.g. an oral mode) is used to introduce the drug into a subject, the bioavailability for that mode of administration may be compared to a different mode of administration, e.g. an IV mode of administration. In some embodiments, the area under a compound's blood plasma concentration curve ($AUC_o$) after non-parenteral (e.g. oral, rectal, intrajejunal) administration may be divided by the area under the drug's plasma concentration curve after intravenous (i.v.) administration ($AUC_{iv}$) to provide a dimensionless quotient (relative bioavailability, RB) that represents fraction of compound absorbed via the non-parenteral route as compared to the IV route. A composition's bioavailability is said to be enhanced in comparison to another composition's bioavailability when the first composition's relative bioavailability ($RB_1$) is greater than the second composition's relative bioavailability ($RB_2$).

In general, bioavailability correlates with therapeutic efficacy when a compound's therapeutic efficacy is related to the blood concentration achieved, even if the drug's ultimate site of action is intracellular (van Berge-Henegouwen et al., *Gastroenterol.*, 1977, 73, 300). Bioavailability studies have been used to determine the degree of intestinal absorption of a drug by measuring the change in peripheral blood levels of the drug after an oral dose (DiSanto, Chapter 76 In: *Remington's Pharmaceutical Sciences,* 18th Ed., Gennaro, ed., Mack Publishing Co., Easton, Pa., 1990, pages 1451-1458).

In general, an oral composition's bioavailability is said to be "enhanced" when its relative bioavailability is greater than the bioavailability of a composition substantially consisting of pure oligonucleotide, i.e. oligonucleotide in the absence of a penetration enhancer.

Organ bioavailability refers to the concentration of compound in an organ. Organ bioavailability may be measured in test subjects by a number of means, such as by whole-body radiography. Organ bioavailability may be modified, e.g. enhanced, by one or more modifications to the oligonucleotide, by use of one or more carrier compounds or excipients, etc. as discussed in more detail herein. In general, an increase in bioavailability will result in an increase in organ bioavailability.

Oral oligonucleotide compositions according to the present invention may comprise one or more "mucosal penetration enhancers," also known as "absorption enhancers" or simply as "penetration enhancers." Accordingly, some embodiments of the invention comprise at least one oligonucleotide in combination with at least one penetration enhancer. In general, a penetration enhancer is a substance that facilitates the transport of a drug across mucous membrane(s) associated with the desired mode of administration, e.g. intestinal epithelial membranes. Accordingly it is desirable to select one or more penetration enhancers that facilitate the uptake of an oligonucleotide, without interfering with the activity of the oligonucleotide, and in a such a manner the oligonucleotide can be introduced into the body of an animal without unacceptable side-effects such as toxicity, irritation or allergic response.

Embodiments of the present invention provide compositions comprising one or more pharmaceutically acceptable penetration enhancers, and methods of using such compositions, which result in the improved bioavailability of oligonucleotides administered via non-parenteral modes of administration. Heretofore, certain penetration enhancers have been used to improve the bioavailability of certain drugs. See Muranishi, *Crit. Rev. Ther. Drug Carrier Systems,* 1990, 7, 1 and Lee et al., *Crit. Rev. Ther. Drug Carrier Systems,* 1991, 8, 91. It has been found that the uptake and delivery of oligonucleotides, relatively complex molecules which are known to be difficult to administer to animals and man, can be greatly improved even when administered by non-parenteral means through the use of a number of different classes of penetration enhancers.

In some embodiments, compositions for non-parenteral administration include one or more modifications from naturally-occurring oligonucleotides (i.e. full-phosphodiester deoxyribosyl or full-phosphodiester ribosyl oligonucleotides). Such modifications may increase binding affinity, nuclease stability, cell or tissue permeability, tissue distribution, or other biological or pharmacokinetic property. Modifications may be made to the base, the linker, or the sugar, in general, as discussed in more detail herein with regards to oligonucleotide chemistry. In some embodiments of the invention, compositions for administration to a subject, and in particular oral compositions for administration to an animal or human subject, will comprise modified oligonucleotides having one or more modifications for enhancing affinity, stability, tissue distribution, or other biological property.

Suitable modified linkers include phosphorothioate linkers. In some embodiments according to the invention, the oligonucleotide has at least one phosphorothioate linker. Phosphorothioate linkers provide nuclease stability as well as plasma protein binding characteristics to the oligonucleotide. Nuclease stability is useful for increasing the in vivo lifetime of oligonucleotides, while plasma protein binding decreases the rate of first pass clearance of oligonucleotide via renal excretion. In some embodiments according to the present invention, the oligonucleotide has at least two phosphorothioate linkers. In some embodiments, wherein the oligonucleotide has exactly n nucleosides, the oligonucleotide has from one to n−1 phosphorothioate linkages. In some embodiments, wherein the oligonucleotide has exactly n nucleosides, the oligonucleotide has n−1 phosphorothioate linkages. In other embodiments wherein the oligonucleotide has exactly n nucleosides, and n is even, the oligonucleotide has from 1 to n/2 phosphorothioate linkages, or, when n is odd, from 1 to (n−1)/2 phosphorothioate linkages. In some embodiments, the oligonucleotide has alternating phosphodiester (PO) and phosphorothioate (PS) linkages. In other embodiments, the oligonucleotide has at least one stretch of two or more consecutive PO linkages and at least one stretch of two or more PS linkages. In other embodiments, the oligonucleotide has at least two stretches of PO linkages interrupted by at least on PS linkage.

In some embodiments, at least one of the nucleosides is modified on the ribosyl sugar unit by a modification that imparts nuclease stability, binding affinity or some other beneficial biological property to the sugar. In some cases, the sugar modification includes a 2'-modification, e.g. the 2'-OH of the ribosyl sugar is replaced or substituted. Suitable replacements for 2'-OH include 2'-F and 2'-arabino-F. Suitable substitutions for OH include 2'-O-alkyl, e.g. 2-O-methyl, and 2'-O-substituted alkyl, e.g. 2'-O-methoxyethyl, 2'-O-aminopropyl, etc. In some embodiments, the oligonucleotide contains at least one 2'-modification. In some embodiments, the oligonucleotide contains at least 2 2'-modifications. In some embodiments, the oligonucleotide has at least one 2'-modification at each of the termini (i.e. the 3'- and 5'-terminal nucleosides each have the same or different 2'-modifications). In some embodiments, the oligonucleotide has at least two sequential 2'-modifications at each end of the oligonucleotide. In some embodiments, oligonucleotides further comprise at least one deoxynucleoside. In particular embodiments, oligonucleotides comprise a stretch of deoxynucleosides such that the stretch is capable of activating RNase (e.g. RNase H) cleavage of an RNA to which the oligonucleotide is capable of hybridizing. In some embodiments, a stretch of deoxynucleosides capable of activating RNase-mediated cleavage of RNA comprises about 6 to about 16, e.g. about 8 to about 16 consecutive deoxynucleosides. In further embodiments, oligonucleotides are capable of eliciting cleaveage by dsRNAse enzymes.

Oral compositions for administration of non-parenteral oligonucleotide compositions of the present invention may be formulated in various dosage forms such as, but not limited to, tablets, capsules, liquid syrups, soft gels, suppositories, and enemas. The term "alimentary delivery" encompasses e.g. oral, rectal, endoscopic and sublingual/buccal administration. A common requirement for these modes of administration is absorption over some portion or all of the alimentary tract and a need for efficient mucosal penetration of the nucleic acid(s) so administered.

Delivery of a drug via the oral mucosa, as in the case of buccal and sublingual administration, has several desirable features, including, in many instances, a more rapid rise in plasma concentration of the drug than via oral delivery (Harvey, Chapter 35 In: *Remington's Pharmaceutical Sciences,* 18th Ed., Gennaro, ed., Mack Publishing Co., Easton, Pa., 1990, page 711).

Endoscopy may be used for drug delivery directly to an interior portion of the alimentary tract. For example, endoscopic retrograde cystopancreatography (ERCP) takes advantage of extended gastroscopy and permits selective access to the biliary tract and the pancreatic duct (Hirahata et al., *Gan To Kagaku Ryoho*, 1992, 19(10 Suppl.), 1591). Pharmaceutical compositions, including liposomal formulations, can be delivered directly into portions of the alimentary canal, such as, e.g., the duodenum (Somogyi et al., *Pharm. Res.*, 1995, 12, 149) or the gastric submucosa (Akamo et al., *Japanese J. Cancer Res.*, 1994, 85, 652) via endoscopic means. Gastric lavage devices (Inoue et al., *Artif. Organs*, 1997, 21, 28) and percutaneous endoscopic feeding devices (Pennington et al., *Ailment Pharmacol. Ther.*, 1995, 9, 471) can also be used for direct alimentary delivery of pharmaceutical compositions.

In some embodiments, oligonucleotide formulations may be administered through the anus into the rectum or lower intestine. Rectal suppositories, retention enemas or rectal catheters can be used for this purpose and may be preferred when patient compliance might otherwise be difficult to achieve (e.g., in pediatric and geriatric applications, or when the patient is vomiting or unconscious). Rectal administration can result in more prompt and higher blood levels than the oral route. (Harvey, Chapter 35 In: *Remington's Pharmaceutical Sciences*, 18th Ed., Gennaro, ed., Mack Publishing Co., Easton, Pa., 1990, page 711). Because about 50% of the drug that is absorbed from the rectum will bypass the liver, administration by this route significantly reduces the potential for first-pass metabolism (Benet et al., Chapter 1 In: *Goodman & Gilman's The Pharmacological Basis of Therapeutics*, 9th Ed., Hardman et al., eds., McGraw-Hill, New York, N.Y., 1996).

One advantageous method of non-parenteral administration of oligonucleotide compositions is oral delivery. Some embodiments employ various penetration enhancers in order to effect transport of oligonucleotides and other nucleic acids across mucosal and epithelial membranes. Penetration enhancers may be classified as belonging to one of five broad categories—surfactants, fatty acids, bile salts, chelating agents, and non-chelating non-surfactants (Lee et al., *Critical Reviews in Therapeutic Drug Carrier Systems*, 1991, p. 92). Accordingly, some embodiments comprise oral oligonucleotide compositions comprising at least one member of the group consisting of surfactants, fatty acids, bile salts, chelating agents, and non-chelating surfactants. Further embodiments comprise oral oligonucleotide comprising at least one fatty acid, e.g. capric or lauric acid, or combinations or salts thereof. Other embodiments comprise methods of enhancing the oral bioavailability of an oligonucleotide, the method comprising co-administering the oligonucleotide and at least one penetration enhancer.

Other excipients that may be added to oral oligonucleotide compositions include surfactants (or "surface-active agents"), which are chemical entities which, when dissolved in an aqueous solution, reduce the surface tension of the solution or the interfacial tension between the aqueous solution and another liquid, with the result that absorption of oligonucleotides through the alimentary mucosa and other epithelial membranes is enhanced. In addition to bile salts and fatty acids, surfactants include, for example, sodium lauryl sulfate, polyoxyethylene-9-lauryl ether and polyoxyethylene-20-cetyl ether (Lee et al., *Critical Reviews in Therapeutic Drug Carrier Systems*, 1991, page 92); and perfluorohemical emulsions, such as FC-43 (Takahashi et al., *J. Pharm. Phamacol.*, 1988, 40, 252).

Fatty acids and their derivatives which act as penetration enhancers and may be used in compositions of the present invention include, for example, oleic acid, lauric acid, capric acid (n-decanoic acid), myristic acid, palmitic acid, stearic acid, linoleic acid, linolenic acid, dicaprate, tricaprate, monoolein (1-monooleoyl-rac-glycerol), dilaurin, caprylic acid, arachidonic acid, glyceryl 1-monocaprate, 1-dodecylazacycloheptan-2-one, acylcarnitines, acylcholines and mono- and di-glycerides thereof and/or physiologically acceptable salts thereof (i.e., oleate, laurate, caprate, myristate, palmitate, stearate, linoleate, etc.) (Lee et al., *Critical Reviews in Therapeutic Drug Carrier Systems*, 1991, page 92; Muranishi, *Critical Reviews in Therapeutic Drug Carrier Systems*, 1990, 7, 1; El-Hariri et al., *J. Pharm. Pharmacol.*, 1992, 44, 651).

In some embodiments, oligonucleotide compositions for oral delivery comprise at least two discrete phases, which phases may comprise particles, capsules, gel-capsules, microspheres, etc. Each phase may contain one or more oligonucleotides, penetration enhancers, surfactants, bioadhesives, effervescent agents, or other adjuvant, excipient or diluent. In some embodiments, one phase comprises at least one oligonucleotide and at lease one penetration enhancer. In some embodiments, a first phase comprises at least one oligonucleotide and at least one penetration enhancer, while a second phase comprises at least one penetration enhancer. In some embodiments, a first phase comprises at least one oligonucleotide and at least one penetration enhancer, while a second phase comprises at least one penetration enhancer and substantially no oligonucleotide. In some embodiments, at least one phase is compounded with at least one degradation retardant, such as a coating or a matrix, which delays release of the contents of that phase. In some embodiments, a first phase comprises at least one oligonucleotide, at least one penetration enhancer, while a second phase comprises at least one penetration enhancer and a release-retardant. In particular embodiments, an oral oligonucleotide comprises a first phase comprising particles containing an oligonucleotide and a penetration enhancer, and a second phase comprising particles coated with a release-retarding agent and containing penetration enhancer.

A variety of bile salts also function as penetration enhancers to facilitate the uptake and bioavailability of drugs. The physiological roles of bile include the facilitation of dispersion and absorption of lipids and fat-soluble vitamins (Brunton, Chapter 38 In: *Goodman & Gilman's The Pharmacological Basis of Therapeutics*, 9th Ed., Hardman et al., eds., McGraw-Hill, New York, N.Y., 1996, pages 934-935). Various natural bile salts, and their synthetic derivatives, act as penetration enhancers. Thus, the term "bile salt" includes any of the naturally occurring components of bile as well as any of their synthetic derivatives. The bile salts of the invention include, for example, cholic acid (or its pharmaceutically acceptable sodium salt, sodium cholate), dehydrocholic acid (sodium dehydrocholate), deoxycholic acid (sodium deoxycholate), glucholic acid (sodium glucholate), glycholic acid (sodium glycocholate), glycodeoxycholic acid (sodium glycodeoxycholate), taurocholic acid (sodium taurocholate), taurodeoxycholic acid (sodium taurodeoxycholate), chenodeoxycholic acid (CDCA, sodium chenodeoxycholate), ursodeoxycholic acid (UDCA), sodium tauro-24,25-dihydrofusidate (STDHF), sodium glycodihydrofusidate and polyoxyethylene-9-lauryl ether (POE) (Lee et al., *Critical Reviews in Therapeutic Drug Carrier Systems*, 1991, page 92; Swinyard, Chapter 39 In: *Remington's Pharmaceutical Sciences*, 18th Ed., Gennaro, ed., Mack Publishing Co., Easton, Pa., 1990, pages 782-783; Muranishi, *Critical Reviews in*

Therapeutic Drug Carrier Systems, 1990, 7, 1; Yamamoto et al., J. Pharm. Exp. Ther., 1992, 263, 25; Yamashita et al., J. Pharm. Sci., 1990, 79, 579).

In some embodiments, penetration enhancers useful in some embodiments of present invention are mixtures of penetration enhancing compounds. One such penetration enhancer is a mixture of UDCA (and/or CDCA) with capric and/or lauric acids or salts thereof e.g. sodium. Such mixtures are useful for enhancing the delivery of biologically active substances across mucosal membranes, in particular intestinal mucosa. Other penetration enhancer mixtures comprise about 5-95% of bile acid or salt(s) UDCA and/or CDCA with 5-95% capric and/or lauric acid. Particular penetration enhancers are mixtures of the sodium salts of UDCA, capric acid and lauric acid in a ratio of about 1:2:2 respectively. Anther such penetration enhancer is a mixture of capric and lauric acid (or salts thereof) in a 0.01:1 to 1:0.01 ratio (mole basis). In particular embodiments capric acid and lauric acid are present in molar ratios of e.g. about 0.1:1 to about 1:0.1, in particular about 0.5:1 to about 1:0.5.

Other excipients include chelating agents, i.e. compounds that remove metallic ions from solution by forming complexes therewith, with the result that absorption of oligonucleotides through the alimentary and other mucosa is enhanced. With regards to their use as penetration enhancers in the present invention, chelating agents have the added advantage of also serving as DNase inhibitors, as most characterized DNA nucleases require a divalent metal ion for catalysis and are thus inhibited by chelating agents (Jarrett, J. Chromatogr., 1993, 618, 315). Chelating agents of the invention include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines)(Lee et al., Critical Reviews in Therapeutic Drug Carrier Systems, 1991, page 92; Muranishi, Critical Reviews in Therapeutic Drug Carrier Systems, 1990, 7, 1; Buur et al., J. Control Rel., 1990, 14, 43).

As used herein, non-chelating non-surfactant penetration enhancers may be defined as compounds that demonstrate insignificant activity as chelating agents or as surfactants but that nonetheless enhance absorption of oligonucleotides through the alimentary and other mucosal membranes (Muranishi, Critical Reviews in Therapeutic Drug Carrier Systems, 1990, 7, 1). This class of penetration enhancers includes, but is not limited to, unsaturated cyclic ureas, 1-alkyl- and 1-alkenylazacyclo-alkanone derivatives (Lee et al., Critical Reviews in Therapeutic Drug Carrier Systems, 1991, page 92); and non-steroidal anti-inflammatory agents such as diclofenac sodium, indomethacin and phenylbutazone (Yamashita et al., J. Pharm. Pharmacol., 1987, 39, 621).

Agents that enhance uptake of oligonucleotides at the cellular level may also be added to the pharmaceutical and other compositions of the present invention. For example, cationic lipids, such as lipofectin (Junichi et al, U.S. Pat. No. 5,705, 188), cationic glycerol derivatives, and polycationic molecules, such as polylysine (Lollo et al., PCT Application WO 97/30731), can be used.

Some oral oligonucleotide compositions also incorporate carrier compounds in the formulation. As used herein, "carrier compound" or "carrier" can refer to a nucleic acid, or analog thereof, which may be inert (i.e., does not possess biological activity per se) or may be necessary for transport, recognition or pathway activation or mediation, or is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. For example, the recovery of a partially phosphorothioate oligonucleotide in hepatic tissue can be reduced when it is coadministered with polyinosinic acid, dextran sulfate, polycytidic acid or 4-acetamido-4'isothiocyano-stilbene-2,2'-disulfonic acid (Miyao et al., Antisense Res. Dev., 1995, 5, 115; Takakura et al., Antisense & Nucl. Acid Drug Dev., 1996, 6, 177).

A "pharmaceutical carrier" or "excipient" may be a pharmaceutically acceptable solvent, suspending agent or any other pharmacologically inert vehicle for delivering one or more nucleic acids to an animal. The excipient may be liquid or solid and is selected, with the planned manner of administration in mind, so as to provide for the desired bulk, consistency, etc., when combined with a nucleic acid and the other components of a given pharmaceutical composition. Typical pharmaceutical carriers include, but are not limited to, binding agents (e.g., pregelatinised maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc.); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrants (e.g., starch, sodium starch glycolate, EXPLOTAB); and wetting agents (e.g., sodium lauryl sulphate, etc.).

Oral oligonucleotide compositions may additionally contain other adjunct components conventionally found in pharmaceutical compositions, at their art-established usage levels. Thus, for example, the compositions may contain additional, compatible, pharmaceutically-active materials such as, for example, antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions of the present invention.

Certain embodiments of the invention provide pharmaceutical compositions containing one or more oligomeric compounds and one or more other chemotherapeutic agents which function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds of the invention, such chemo-therapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions of the invention. Combinations of antisense compounds and other non-antisense drugs are also within the scope of this invention. Two or more combined compounds may be used together or sequentially.

In another related embodiment, compositions of the invention may contain one or more antisense compounds, particularly oligonucleotides, targeted to a first nucleic acid and one or more additional antisense compounds targeted to a second nucleic acid target. Alternatively, compositions of the invention may contain two or more antisense compounds targeted to different regions of the same nucleic acid target. Numerous examples of antisense compounds are known in the art. Two or more combined compounds may be used together or sequentially.

E. Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Persons of ordinary skill can easily determine optimum dosages, dosing methodologies and repetition rates. Optimum dosages may vary depending on the relative potency of individual oligonucleotides, and can generally be estimated based on $EC_{50}s$ found to be effective in in vitro and in vivo animal models. In general, dosage is from 0.0001 µg to 100 g per kg of body weight, and may be given once or more daily, weekly, monthly or yearly, or even once every 2 to 20 years. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the oligonucleotide is administered in maintenance doses, ranging from 0.0001 µg to 100 g per kg of body weight, once or more daily, to once every 20 years.

While the present invention has been described with specificity in accordance with certain of its preferred embodiments, the following examples serve only to illustrate the invention and are not intended to limit the same. Each of the references, GenBank accession numbers, and the like recited in the present application is incorporated herein by reference in its entirety.

EXAMPLES

Example 1

Synthesis of Nucleoside Phosphoramidites

The following compounds, including amidites and their intermediates were prepared as described in U.S. Pat. No. 6,426,220 and published PCT WO 02/36743; 5'-O-Dimethoxytrityl-thymidine intermediate for 5-methyl dC amidite, 5'-O-Dimethoxytrityl-2'-deoxy-5-methylcytidine intermediate for 5-methyl-dC amidite, 5'-O-Dimethoxytrityl-2'-deoxy-N4-benzoyl-5-methylcytidine penultimate intermediate for 5-methyl dC amidite, [5'-O-(4,4'-Dimethoxytriphenylmethyl)-2'-deoxy-N4-benzoyl-5-methylcytidin-3'-O-yl]-2-cyanoethyl-N,N-diisopropylphosphoramidite(5-methyl dC amidite), 2'-Fluorodeoxyadenosine, 2'-Fluorodeoxyguanosine, 2'-Fluorouridine, 2'-Fluorodeoxycytidine, 2'-O-(2-Methoxyethyl) modified amidites, 2'-O-(2-methoxyethyl)-5-methyluridine intermediate, 5'-O-DMT-2'-O-(2-methoxyethyl)-5-methyluridine penultimate intermediate, [5'-O-(4,4'-Dimethoxytriphenylmethyl)-2'-O-(2-methoxyethyl)-5-methyluridin-3'-O-yl]-2-cyanoethyl-N,N-diisopropylphosphoramidite (MOE T amidite), 5'-O-Dimethoxytrityl-2'-O-(2-methoxyethyl)-5-methylcytidine intermediate, 5'-O-dimethoxytrityl-2'-O-(2-methoxyethyl)-$N^4$-benzoyl-5-methyl-cytidine penultimate intermediate, [5'-O-(4,4'-Dimethoxytriphenylmethyl)-2'-O-(2-methoxyethyl)-$N^4$-benzoyl-5-methylcytidin-3'-O-yl]-2-cyanoethyl-N,N-diisopropylphosphoramidite (MOE 5-Me-C amidite), [5'-O-(4,4'-Dimethoxytriphenylmethyl)-2'-O-(2-methoxyethyl)-$N^6$-benzoyladenosin-3'-O-yl]-2-cyanoethyl-N,N-diisopropylphosphoramidite (MOE A amdite), [5'-O-(4,4'-Dimethoxytriphenylmethyl)-2'-O-(2-methoxyethyl)-$N^4$-isobutyrylguanosin-3'-O-yl]-2-cyanoethyl-N,N-diisopropylphosphoramidite (MOE G amidite), 2'-O-(Aminooxyethyl)nucleoside amidites and 2'-O-(dimethylaminooxyethyl)nucleoside amidites, 2'-(Dimethylaminooxyethoxy)nucleoside amidites, 5'-O-tert-Butyldiphenylsilyl-$O^2$-2'-anhydro-5-methyluridine, 5'-O-tert-Butyldiphenylsilyl-2'-O-(2-hydroxyethyl)-5-methyluridine, 2'-O-([2-phthalimidoxy)ethyl]-5'-t-butyldiphenylsilyl-5-methyluridine, 5'-O-tert-butyldiphenylsilyl-2'-O-[(2-formadoximinooxy)ethyl]-5-methyluridine, 5'-O-tert-Butyldiphenylsilyl-2'-O—[N,N dimethylaminooxyethyl]-5-methyluridine, 2'-O-(dimethylaminooxyethyl)-5-methyluridine, 5'-O-DMT-2'-O-(dimethylaminooxyethyl)-5-methyluridine, 5'-O-DMT-2'-O-(2-N,N-dimethylaminooxyethyl)-5-methyluridine-3'-[(2-cyanoethyl)-N,N-diisopropylphosphoramidite], 2'-(Aminooxyethoxy)nucleoside amidites, N2-isobutyryl-6-O-diphenylcarbamoyl-2'-O-(2-ethylacetyl)-5'-O-(4,4'-dimethoxytrityl)guanosine-3'-[(2-cyanoethyl)-N,N-diisopropylphosphoramidite], 2'-dimethylaminoethoxyethoxy (2'-DMAEOE) nucleoside amidites, 2'-O-[2(2-N,N-dimethylaminoethoxy)ethyl]-5-methyl uridine, 5'-O-dimethoxytrityl-2'-O-[2(2-N,N-dimethylaminoethoxy)-ethyl)]-5-methyl uridine and 5'-O-Dimethoxytrityl-2'-O-[2(2-N,N-dimethylaminoethoxy)-ethyl)]-5-methyl uridine-3'-O-(cyanoethyl-N,N-diisopropyl) phosphoramidite.

Example 2

Oligonucleotide and Oligonucleoside Synthesis

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare oligonucleotides such as the phosphorothioates and alkylated derivatives.

Oligonucleotides

Unsubstituted and substituted phosphodiester (P=O) oligonucleotides are synthesized on an automated DNA synthesizer (Applied Biosystems model 394) using standard phosphoramidite chemistry with oxidation by iodine.

Phosphorothioates (P=S) are synthesized similar to phosphodiester oligonucleotides with the following exceptions: thiation was effected by utilizing a 10% w/v solution of 3,H-1,2-benzodithiole-3-one 1,1-dioxide in acetonitrile for the oxidation of the phosphite linkages. The thiation reaction step time was increased to 180 sec and preceded by the normal capping step. After cleavage from the CPG column and deblocking in concentrated ammonium hydroxide at 55° C. (12-16 hr), the oligonucleotides were recovered by precipitating with >3 volumes of ethanol from a 1 M $NH_4OAc$ solution. Phosphinate oligonucleotides are prepared as described in U.S. Pat. No. 5,508,270, herein incorporated by reference.

Alkyl phosphonate oligonucleotides are prepared as described in U.S. Pat. No. 4,469,863, herein incorporated by reference.

3'-Deoxy-3'-methylene phosphonate oligonucleotides are prepared as described in U.S. Pat. No. 5,610,289 or 5,625,050, herein incorporated by reference.

Phosphoramidite oligonucleotides are prepared as described in U.S. Pat. No. 5,256,775 or U.S. Pat. No. 5,366,878, herein incorporated by reference.

Alkylphosphonothioate oligonucleotides are prepared as described in published PCT applications PCT/US94/00902 and PCT/US93/06976 (published as WO 94/17093 and WO 94/02499, respectively), herein incorporated by reference.

3'-Deoxy-3'-amino phosphoramidate oligonucleotides are prepared as described in U.S. Pat. No. 5,476,925, herein incorporated by reference.

Phosphotriester oligonucleotides are prepared as described in U.S. Pat. No. 5,023,243, herein incorporated by reference.

Borano phosphate oligonucleotides are prepared as described in U.S. Pat. Nos. 5,130,302 and 5,177,198, both herein incorporated by reference.

Oligonucleosides

Methylenemethylimino linked oligonucleosides, also identified as MMI linked oligonucleosides, methylenedimethylhydrazo linked oligonucleosides, also identified as MDH linked oligonucleosides, and methylenecarbonylamino linked oligonucleosides, also identified as amide-3 linked oligonucleosides, and methyleneaminocarbonyl linked oligonucleosides, also identified as amide-4 linked oligonucleosides, as well as mixed backbone compounds having, for instance, alternating MMI and P=O or P=S linkages are prepared as described in U.S. Pat. Nos. 5,378,825, 5,386,023, 5,489,677, 5,602,240 and 5,610,289, all of which are herein incorporated by reference.

Formacetal and thioformacetal linked oligonucleosides are prepared as described in U.S. Pat. Nos. 5,264,562 and 5,264,564, herein incorporated by reference.

Ethylene oxide linked oligonucleosides are prepared as described in U.S. Pat. No. 5,223,618, herein incorporated by reference.

Example 3

RNA Synthesis

In general, RNA synthesis chemistry is based on the selective incorporation of various protecting groups at strategic intermediary reactions. Although one of ordinary skill in the art will understand the use of protecting groups in organic synthesis, a useful class of protecting groups includes silyl ethers. In particular bulky silyl ethers are used to protect the 5'-hydroxyl in combination with an acid-labile orthoester protecting group on the 2'-hydroxyl. This set of protecting groups is then used with standard solid-phase synthesis technology. It is important to lastly remove the acid labile orthoester protecting group after all other synthetic steps. Moreover, the early use of the silyl protecting groups during synthesis ensures facile removal when desired, without undesired deprotection of 2' hydroxyl.

Following this procedure for the sequential protection of the 5'-hydroxyl in combination with protection of the 2'-hydroxyl by protecting groups that are differentially removed and are differentially chemically labile, RNA oligonucleotides were synthesized.

RNA oligonucleotides are synthesized in a stepwise fashion. Each nucleotide is added sequentially (3'- to 5'-direction) to a solid support-bound oligonucleotide. The first nucleoside at the 3'-end of the chain is covalently attached to a solid support. The nucleotide precursor, a ribonucleoside phosphoramidite, and activator are added, coupling the second base onto the 5'-end of the first nucleoside. The support is washed and any unreacted 5'-hydroxyl groups are capped with acetic anhydride to yield 5'-acetyl moieties. The linkage is then oxidized to the more stable and ultimately desired P(V) linkage. At the end of the nucleotide addition cycle, the 5'-silyl group is cleaved with fluoride. The cycle is repeated for each subsequent nucleotide.

Following synthesis, the methyl protecting groups on the phosphates are cleaved in 30 minutes utilizing 1 M disodium-2-carbamoyl-2-cyanoethylene-1,1-dithiolate trihydrate ($S_2Na_2$) in DMF. The deprotection solution is washed from the solid support-bound oligonucleotide using water. The support is then treated with 40% methylamine in water for 10 minutes at 55° C. This releases the RNA oligonucleotides into solution, deprotects the exocyclic amines, and modifies the 2'-groups. The oligonucleotides can be analyzed by anion exchange HPLC at this stage.

The 2'-orthoester groups are the last protecting groups to be removed. The ethylene glycol monoacetate orthoester protecting group developed by Dharmacon Research, Inc. (Lafayette, Colo.), is one example of a useful orthoester protecting group which, has the following important properties. It is stable to the conditions of nucleoside phosphoramidite synthesis and oligonucleotide synthesis. However, after oligonucleotide synthesis the oligonucleotide is treated with methylamine which not only cleaves the oligonucleotide from the solid support but also removes the acetyl groups from the orthoesters. The resulting 2-ethyl-hydroxyl substituents on the orthoester are less electron withdrawing than the acetylated precursor. As a result, the modified orthoester becomes more labile to acid-catalyzed hydrolysis. Specifically, the rate of cleavage is approximately 10 times faster after the acetyl groups are removed. Therefore, this orthoester possesses sufficient stability in order to be compatible with oligonucleotide synthesis and yet, when subsequently modified, permits deprotection to be carried out under relatively mild aqueous conditions compatible with the final RNA oligonucleotide product.

Additionally, methods of RNA synthesis are well known in the art (Scaringe, S. A. Ph.D. Thesis, University of Colorado, 1996; Scaringe, S. A., et al., *J. Am. Chem. Soc.*, 1998, 120, 11820-11821; Matteucci, M. D. and Caruthers, M. H. *J. Am. Chem. Soc.*, 1981, 103, 3185-3191; Beaucage, S. L. and Caruthers, M. H. *Tetrahedron Lett.*, 1981, 22, 1859-1862; Dahl, B. J., et al., *Acta Chem. Scand,*. 1990, 44, 639-641; Reddy, M. P., et al., *Tetrahedrom Lett.*, 1994, 25, 4311-4314;

Wincott, F. et al., *Nucleic Acids Res.*, 1995, 23, 2677-2684; Griffin, B. E., et al., *Tetrahedron*, 1967, 23, 2301-2313; Griffin, B. E., et al., *Tetrahedron*, 1967, 23, 2315-2331).

RNA antisense compounds (RNA oligonucleotides) of the present invention can be synthesized by the methods herein or purchased from Dharmacon Research, Inc (Lafayette, Colo.). Once synthesized, complementary RNA antisense compounds can then be annealed by methods known in the art to form double stranded (duplexed) antisense compounds. For example, duplexes can be formed by combining 30 µl of each of the complementary strands of RNA oligonucleotides (50 µM RNA oligonucleotide solution) and 15 µl of 5× annealing buffer (100 mM potassium acetate, 30 mM HEPES-KOH pH 7.4, 2 mM magnesium acetate) followed by heating for 1 minute at 90° C., then 1 hour at 37° C. The resulting duplexed antisense compounds can be used in kits, assays, screens, or other methods to investigate the role of a target nucleic acid, or for diagnostic or therapeutic purposes.

Example 4

Synthesis of Chimeric Compounds

Chimeric oligonucleotides, oligonucleosides or mixed oligonucleotides/oligonucleosides of the invention can be of several different types. These include a first type wherein the "gap" segment of linked nucleosides is positioned between 5' and 3' "wing" segments of linked nucleosides and a second "open end" type wherein the "gap" segment is located at either the 3' or the 5' terminus of the oligomeric compound. Oligonucleotides of the first type are also known in the art as "gapmers" or gapped oligonucleotides. Oligonucleotides of the second type are also known in the art as "hemimers" or "wingmers".

[2'-O-Me]-[2'-deoxy]-[2'-O-Me]Chimeric Phosphorothioate Oligonucleotides

Chimeric oligonucleotides having 2'-O-alkyl phosphorothioate and 2'-deoxy phosphorothioate oligonucleotide segments are synthesized using an Applied Biosystems automated DNA synthesizer Model 394, as above. Oligonucleotides are synthesized using the automated synthesizer and 2'-deoxy-5'-dimethoxytrityl-3'-O-phosphor-amidite for the DNA portion and 5'-dimethoxytrityl-2'-O-methyl-3'-O-phosphoramidite for 5' and 3' wings. The standard synthesis cycle is modified by incorporating coupling steps with increased reaction times for the 5'-dimethoxytrityl-2'-O-methyl-3'-O-phosphoramidite. The fully protected oligonucleotide is cleaved from the support and deprotected in concentrated ammonia (NH$_4$OH) for 12-16 hr at 55° C. The deprotected oligo is then recovered by an appropriate method (precipitation, column chromatography, volume reduced in vacuo and analyzed spetrophotometrically for yield and for purity by capillary electrophoresis and by mass spectrometry.

[2'-O-(2-Methoxyethyl)]-[2'-deoxy]-[2'-O-(Methoxyethyl)]Chimeric Phosphorothioate Oligonucleotides

[2'-O-(2-methoxyethyl)]-[2'-deoxy]-[-2'-O-(methoxyethyl)]chimeric phosphorothioate oligonucleotides were prepared as per the procedure above for the 2'-O-methyl chimeric oligonucleotide, with the substitution of 2'-O-(methoxyethyl) amidites for the 2'-O-methyl amidites.

[2'-O-(2-Methoxyethyl)Phosphodiester]-[2'-deoxy Phosphorothioate]-[2'-O-(2-Methoxyethyl)Phosphodiester]Chimeric Oligonucleotides

[2'-O-(2-methoxyethyl phosphodiester]-[2'-deoxy phosphorothioate]-[2'-O-(methoxyethyl)phosphodiester]chimeric oligonucleotides are prepared as per the above procedure for the 2'-O-methyl chimeric oligonucleotide with the substitution of 2'-O-(methoxyethyl) amidites for the 2'-O-methyl amidites, oxidation with iodine to generate the phosphodiester internucleotide linkages within the wing portions of the chimeric structures and sulfurization utilizing 3,H-1,2 benzodithiole-3-one 1,1 dioxide (Beaucage Reagent) to generate the phosphorothioate internucleotide linkages for the center gap.

Other chimeric oligonucleotides, chimeric oligonucleosides and mixed chimeric oligonucleotides/oligonucleosides are synthesized according to U.S. Pat. No. 5,623,065, herein incorporated by reference.

Example 5

Oligonucleotide Isolation

After cleavage from the controlled pore glass solid support and deblocking in concentrated ammonium hydroxide at 55° C. for 12-16 hours, the oligonucleotides or oligonucleosides are recovered by precipitation out of 1 M NH$_4$OAc with >3 volumes of ethanol. Synthesized oligonucleotides were analyzed by electrospray mass spectroscopy (molecular weight determination) and by capillary gel electrophoresis and judged to be at least 70% full length material. The relative amounts of phosphorothioate and phosphodiester linkages obtained in the synthesis was determined by the ratio of correct molecular weight relative to the −16 amu product (±32±48). For some studies oligonucleotides were purified by HPLC, as described by Chiang et al., *J. Biol. Chem.* 1991, 266, 18162-18171. Results obtained with HPLC-purified material were similar to those obtained with non-HPLC purified material.

Example 6

Oligonucleotide Synthesis

96 Well Plate Format

Oligonucleotides were synthesized via solid phase P(III) phosphoramidite chemistry on an automated synthesizer capable of assembling 96 sequences simultaneously in a 96-well format. Phosphodiester internucleotide linkages were afforded by oxidation with aqueous iodine. Phosphorothioate internucleotide linkages were generated by sulfurization utilizing 3,H-1,2 benzodithiole-3-one 1,1 dioxide (Beaucage Reagent) in anhydrous acetonitrile. Standard base-protected beta-cyanoethyl-diiso-propyl phosphoramidites were purchased from commercial vendors (e.g. PE-Applied Biosystems, Foster City, Calif., or Pharmacia, Piscataway, N.J.). Non-standard nucleosides are synthesized as per standard or patented methods. They are utilized as base protected beta-cyanoethyldiisopropyl phosphoramidites.

Oligonucleotides were cleaved from support and deprotected with concentrated NH$_4$OH at elevated temperature (55-60° C.) for 12-16 hours and the released product then dried in vacuo. The dried product was then re-suspended in sterile water to afford a master plate from which all analytical and test plate samples are then diluted utilizing robotic pipettors.

Example 7

Oligonucleotide Analysis

96-Well Plate Format

The concentration of oligonucleotide in each well was assessed by dilution of samples and UV absorption spectroscopy. The full-length integrity of the individual products was evaluated by capillary electrophoresis (CE) in either the 96-well format (Beckman P/ACE™ MDQ) or, for individually prepared samples, on a commercial CE apparatus (e.g., Beckman P/ACE™ 5000, ABI 270). Base and backbone composition was confirmed by mass analysis of the compounds utilizing electrospray-mass spectroscopy. All assay test plates were diluted from the master plate using single and multi-channel robotic pipettors. Plates were judged to be acceptable if at least 85% of the compounds on the plate were at least 85% full length.

Example 8

Cell Culture and Oligonucleotide Treatment

The effect of antisense compounds on target nucleic acid expression can be tested in any of a variety of cell types provided that the target nucleic acid is present at measurable levels. This can be routinely determined using, for example, PCR or Northern blot analysis. The following cell types are provided for illustrative purposes, but other cell types can be routinely used, provided that the target is expressed in the cell type chosen. This can be readily determined by methods routine in the art, for example Northern blot analysis, ribonuclease protection assays, or RT-PCR.

T-24 Cells:

The human transitional cell bladder carcinoma cell line T-24 was obtained from the American Type Culture Collection (ATCC) (Manassas, Va.). T-24 cells were routinely cultured in complete McCoy's 5A basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence. Cells were seeded into 96-well plates (Falcon-Primaria #353872) at a density of 7000 cells/well for use in RT-PCR analysis.

A549 Cells:

The human lung carcinoma cell line A549 was obtained from the American Type Culture Collection (ATCC) (Manassas, Va.). A549 cells were routinely cultured in DMEM basal media (Invitrogen Corporation, Carlsbad, Calif.) supplemented with 10% fetal calf serum (Invitrogen Corporation, Carlsbad, Calif.), penicillin 100 units per mL, and streptomycin 100 micrograms per mL (Invitrogen Corporation, Carlsbad, Calif.). Cells were routinely passaged by trypsinization and dilution when they reached 90% confluence.

NHDF Cells:

Human neonatal dermal fibroblast (NHDF) were obtained from the Clonetics Corporation (Walkersville, Md.). NHDFs were routinely maintained in Fibroblast Growth Medium (Clonetics Corporation, Walkersville, Md.) supplemented as recommended by the supplier. Cells were maintained for up to 10 passages as recommended by the supplier.

HEK Cells:

Human embryonic keratinocytes (HEK) were obtained from the Clonetics Corporation (Walkersville, Md.). HEKs were routinely maintained in Keratinocyte Growth Medium (Clonetics Corporation, Walkersville, Md.) formulated as recommended by the supplier. Cells were routinely maintained for up to 10 passages as recommended by the supplier.

HK-2 Cells:

HK-2 (human kidney 2) is a proximal tubular cell (PTC) line derived from normal kidney cells immortalized by transduction with human papilloma virus 16 (HPV-16) E6/E7 genes (CRL-2190, American Type Culture Collection, Manassas, Va.). HK-2 cells were routinely cultured in Keratinocyte-Serum Free Medium (17005-042, Invitrogen Corporation, Carlsbad, Calif.) which includes 5 ng/ml recombinant epidermal growth factor and 0.05 mg/ml bovine pituitary extract. Cells were routinely passaged by trypsinization and split at a ratio of 1:4 when they reached 70-80% confluence. One day prior to transfection, cells were seeded into 96-well plates (Falcon-Primaria #353872, BD Biosciences, Bedford, Mass.) at a density of 10,000 cells/well.

b.END Cells:

The mouse brain endothelial cell line b.END was obtained from Dr. Werner Risau at the Max Plank Institute (Bad Nauheim, Germany). b.END cells were routinely cultured in DMEM, high glucose (Gibco/Life Technologies, Gaithersburg, Md.) supplemented with 10% fetal calf serum (Gibco/Life Technologies, Gaithersburg, Md.). Cells were routinely passaged by trypsinization and dilution when they reached 90% confluence. Cells were seeded into 96-well plates (Falcon-Primaria #3872) at a density of 3000 cells/well for use in RT-PCR analysis.

Treatment with Antisense Compounds:

When cells reached 65-75% confluency, they were treated with oligonucleotide. For cells grown in 96-well plates, wells were washed once with 100 µL OPTI-MEM™-1 reduced-serum medium (Invitrogen Corporation, Carlsbad, Calif.) and then treated with 130 µL of OPTI-MEM™-1 containing 3.75 µg/mL LIPOFECTIN™ (Invitrogen Corporation, Carlsbad, Calif.) and the desired concentration of oligonucleotide. Cells are treated and data are obtained in triplicate. After 4-7 hours of treatment at 37° C., the medium was replaced with fresh medium. Cells were harvested 16-24 hours after oligonucleotide treatment.

For Northern blotting or other analysis, cells may be seeded onto 100 mm or other standard tissue culture plates and treated similarly, using appropriate volumes of medium and oligonucleotide.

The concentration of oligonucleotide used varies from cell line to cell line. To determine the optimal oligonucleotide concentration for a particular cell line, the cells are treated with a positive control oligonucleotide at a range of concentrations. For human cells the positive control oligonucleotide is selected from either ISIS 13920 (TCCGTCATCGCTCCT-CAGGG; SEQ ID NO: 1) which is targeted to human H-ras, or ISIS 18078, (GTGCGCGCGAGCCCGAAATC; SEQ ID NO: 2) which is targeted to human Jun-N-terminal kinase-2 (JNK2). Both controls are 2'-O-methoxyethyl gapmers (2'-O-methoxyethyls shown in bold) with a phosphorothioate backbone. For mouse or rat cells the positive control oligonucleotide is ISIS 15770 (ATGCATTCTGCCCCCAAGGA; SEQ ID NO: 3), a 2'-O-methoxyethyl gapmer (2'-O-methoxyethyls shown in bold) with a phosphorothioate backbone which is targeted to both mouse and rat c-raf. The concentration of positive control oligonucleotide that results in 80% inhibition of c-H-ras (for ISIS 13920), JNK2 (for ISIS 18078) or c-raf (for ISIS 15770) mRNA is then utilized as the screening concentration for new oligonucleotides in subsequent experiments for that cell line. If 80% inhibition is not achieved, the lowest concentration of positive control oligonucleotide that results in 60% inhibition of c-H-ras, JNK2 or c-raf mRNA is then utilized as the oligonucleotide screening concentration in subsequent experiments for that cell line. If 60% inhibition is not achieved, that particular cell line is deemed as unsuitable for oligonucleotide transfection experiments. The concentrations of antisense oligonucleotides used herein are from 50 nM to 300 nM.

Example 9

Analysis of Oligonucleotide Inhibition of Target Gene Expression

Antisense modulation of target gene expression can be assayed in a variety of ways known in the art. For example, target gene mRNA levels can be quantitated by, e.g., Northern blot analysis, competitive polymerase chain reaction (PCR), or real-time PCR (RT-PCR). Real-time quantitative PCR is presently preferred. RNA analysis can be performed on total cellular RNA or poly(A)+ mRNA. The preferred method of RNA analysis of the present invention is the use of total cellular RNA as described in other examples herein. Methods of RNA isolation are well known in the art. Northern blot analysis is also routine in the art. Real-time quantitative (PCR) can be conveniently accomplished using the commercially available ABI PRISM™ 7600, 7700, or 7900 Sequence Detection System, available from PE-Applied Biosystems, Foster City, Calif. and used according to manufacturer's instructions.

Protein levels of target genes can be quantitated in a variety of ways well known in the art, such as immunoprecipitation, Western blot analysis (immunoblotting), enzyme-linked immunosorbent assay (ELISA) or fluorescence-activated cell sorting (FACS). Antibodies directed to a target gene can be identified and obtained from a variety of sources, such as the MSRS catalog of antibodies (Aerie Corporation, Birmingham, Mich.), or can be prepared via conventional monoclonal or polyclonal antibody generation methods well known in the art.

Example 10

RNA Isolation

Poly(A)+ mRNA Isolation

Poly(A)+ mRNA was isolated according to Miura et al., (*Clin. Chem.*, 1996, 42, 1758-1764). Other methods for poly (A)+ mRNA isolation are routine in the art. Briefly, for cells grown on 96-well plates, growth medium was removed from the cells and each well was washed with 200 µL cold PBS. 60 µL lysis buffer (10 mM Tris-HCl, pH 7.6, 1 mM EDTA, 0.5 M NaCl, 0.5% NP-40, 20 mM vanadyl-ribonucleoside complex) was added to each well, the plate was gently agitated and then incubated at room temperature for five minutes. 55 µL of lysate was transferred to Oligo d(T) coated 96-well plates (AGCT Inc., Irvine Calif.). Plates were incubated for 60 minutes at room temperature, washed 3 times with 200 µL of wash buffer (10 mM Tris-HCl pH 7.6, 1 mM EDTA, 0.3 M NaCl). After the final wash, the plate was blotted on paper towels to remove excess wash buffer and then air-dried for 5 minutes. 60 µL of elution buffer (5 mM Tris-HCl pH 7.6), preheated to 70° C., was added to each well, the plate was incubated on a 90° C. hot plate for 5 minutes, and the eluate was then transferred to a fresh 96-well plate.

Cells grown on 100 mm or other standard plates may be treated similarly, using appropriate volumes of all solutions.
Total RNA Isolation Total RNA was isolated using an RNEASY 96™ kit and buffers purchased from Qiagen Inc. (Valencia, Calif.) following the manufacturer's recommended procedures. Briefly, for cells grown on 96-well plates, growth medium was removed from the cells and each well was washed with 200 µL cold PBS. 150 µL Buffer RLT was added to each well and the plate vigorously agitated for 20 seconds. 150 µL of 70% ethanol was then added to each well and the contents mixed by pipetting three times up and down. The samples were then transferred to the RNEASY 96™ well plate attached to a QIAVAC™ manifold fitted with a waste collection tray and attached to a vacuum source. Vacuum was applied for 1 minute. 500 µL of Buffer RW1 was added to each well of the RNEASY 96™ plate and incubated for 15 minutes and the vacuum was again applied for 1 minute. An additional 500 µL of Buffer RW1 was added to each well of the RNEASY 96™ plate and the vacuum was applied for 2 minutes. 1 mL of Buffer RPE was then added to each well of the RNEASY 96™ plate and the vacuum applied for a period of 90 seconds. The Buffer RPE wash was then repeated and the vacuum was applied for an additional 3 minutes. The plate was then removed from the QIAVAC™ manifold and blotted dry on paper towels. The plate was then re-attached to the QIAVAC™ manifold fitted with a collection tube rack containing 1.2 mL collection tubes. RNA was then eluted by pipetting 140 µL of RNAse free water into each well, incubating 1 minute, and then applying the vacuum for 3 minutes.

The repetitive pipetting and elution steps may be automated using a QIAGEN Bio-Robot 9604 (Qiagen, Inc., Valencia Calif.). Essentially, after lysing of the cells on the culture plate, the plate is transferred to the robot deck where the pipetting, DNase treatment and elution steps are carried out.

Example 11

Real-Time Quantitative PCR Analysis of Target Gene mRNA Levels

Quantitation of target gene mRNA levels was accomplished by real-time quantitative PCR using the ABI PRISM™ 7600, 7700, or 7900 Sequence Detection System (PE-Applied Biosystems, Foster City, Calif.) according to manufacturer's instructions. This is a closed-tube, non-gel-based, fluorescence detection system which allows high-throughput quantitation of polymerase chain reaction (PCR) products in real-time. As opposed to standard PCR in which amplification products are quantitated after the PCR is completed, products in real-time quantitative PCR are quantitated as they accumulate. This is accomplished by including in the PCR reaction an oligonucleotide probe that anneals specifically between the forward and reverse PCR primers, and contains two fluorescent dyes. A reporter dye (e.g., FAM or JOE, obtained from either PE-Applied Biosystems, Foster City, Calif., Operon Technologies Inc., Alameda, Calif. or Integrated DNA Technologies Inc., Coralville, Iowa) is attached to the 5' end of the probe and a quencher dye (e.g., TAMRA, obtained from either PE-Applied Biosystems, Foster City, Calif., Operon Technologies Inc., Alameda, Calif. or Integrated DNA Technologies Inc., Coralville, Iowa) is attached to the 3' end of the probe. When the probe and dyes are intact, reporter dye emission is quenched by the proximity of the 3' quencher dye. During amplification, annealing of the probe to the target sequence creates a substrate that can be cleaved by the 5'-exonuclease activity of Taq polymerase. During the extension phase of the PCR amplification cycle, cleavage of the probe by Taq polymerase releases the reporter dye from the remainder of the probe (and hence from the quencher moiety) and a sequence-specific fluorescent signal is generated. With each cycle, additional reporter dye molecules are cleaved from their respective probes, and the fluorescence intensity is monitored at regular intervals by laser optics built into the ABI PRISM™ Sequence Detection System. In each assay, a series of parallel reactions containing serial dilutions of mRNA from untreated control samples generates a standard curve that is used to quantitate the percent inhibition after antisense oligonucleotide treatment of test samples.

Prior to quantitative PCR analysis, primer-probe sets specific to the target gene being measured are evaluated for their ability to be "multiplexed" with a GAPDH amplification reaction. In multiplexing, both the target gene and the internal standard gene GAPDH are amplified concurrently in a single sample. In this analysis, mRNA isolated from untreated cells is serially diluted. Each dilution is amplified in the presence of primer-probe sets specific for GAPDH only, target gene only ("single-plexing"), or both (multiplexing). Following PCR amplification, standard curves of GAPDH and target mRNA signal as a function of dilution are generated from both the single-plexed and multiplexed samples. If both the slope and correlation coefficient of the GAPDH and target signals generated from the multiplexed samples fall within 10% of their corresponding values generated from the single-plexed samples, the primer-probe set specific for that target is deemed multiplexable. Other methods of PCR are also known in the art.

PCR reagents were obtained from Invitrogen Corporation, (Carlsbad, Calif.). RT-PCR reactions were carried out by adding 20 µL PCR cocktail (2.5×PCR buffer minus MgCl$_2$, 6.6 mM MgCl$_2$, 375 µM each of DATP, dCTP, dCTP and dGTP, 375 nM each of forward primer and reverse primer, 125 nM of probe, 4 Units RNAse inhibitor, 1.25 Units PLATINUM® Taq, 5 Units MuLV reverse transcriptase, and 2.5× ROX dye) to 96-well plates containing 30 µL total RNA solution (20-200 ng). The RT reaction was carried out by incubation for 30 minutes at 48° C. Following a 10 minute incubation at 95° C. to activate the PLATINUM® Taq, 40 cycles of a two-step PCR protocol were carried out: 95° C. for 15 seconds (denaturation) followed by 60° C. for 1.5 minutes (annealing/extension).

Gene target quantities obtained by real time RT-PCR are normalized using either the expression level of GAPDH, a gene whose expression is constant, or by quantifying total RNA using RiboGreen™ (Molecular Probes, Inc. Eugene, Oreg.). GAPDH expression is quantified by real time RT-PCR, by being run simultaneously with the target, multiplexing, or separately. Total RNA is quantified using RiboGreen™ RNA quantification reagent (Molecular Probes, Inc. Eugene, Oreg.). Methods of RNA quantification by RiboGreen™ are taught in Jones, L. J., et al, (Analytical Biochemistry, 1998, 265, 368-374).

In this assay, 170 µL of RiboGreen™ working reagent (RiboGreen™ reagent diluted 1:350 in 10 mM Tris-HCl, 1 mM EDTA, pH 7.5) is pipetted into a 96-well plate containing 30 µL purified, cellular RNA. The plate is read in a CytoFluor 4000 (PE Applied Biosystems) with excitation at 485 nm and emission at 530 nm.

Example 12

Northern Blot Analysis of Target Gene mRNA Levels

For in vivo studies, total RNA was prepared from procured tissues of sacrificed mice by homogenization in GITC buffer (Invitrogen, Carlsbad, Calif.) containing 2-mercaptoethanol (Sigma-Aldrich, St. Louis, Mo.) following manufacturer's recommended protocols followed by ultracentrifugation through a CsCl cushion. For cell culture studies, eighteen hours after antisense treatment, cell monolayers were washed twice with cold PBS and lysed in 1 mL RNAZOL™ (TEL-TEST "B" Inc., Friendswood, Tex.). Total RNA was prepared following manufacturer's recommended protocols.

Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer. RNA transfer was confirmed by UV visualization. Membranes were fixed by UV cross-linking using a STRATALINKER™ UV Crosslinker 2400 (Stratagene, Inc, La Jolla, Calif.) and then probed using RapidHYB™ hybridization solution (Amersham Pharmacia Biotech, Piscataway, N.J.) using manufacturer's recommendations for stringent conditions.

Hybridized membranes were visualized and quantitated using a PHOSPHORIMAGER™ and IMAGEQUANT™ Software V3.3 (Molecular Dynamics, Sunnyvale, Calif.). Data was normalized to GAPDH levels in untreated controls.

Example 13

Design of Chemically Modified Antisense Compounds for Optimized Kidney Targeting A series of chemically modified antisense compounds were designed using the sequence of ISIS 145733 (SEQ ID NO: 4), ISIS 145742 (SEQ ID NO: 5) or ISIS 145746 (SEQ ID NO: 6). Modifications were made to the internucleoside linkages such that the oligonucleotides consisted of either full phosphorothioate backbones or mixed phosphorothioate and phosphodiester backbones (mixed backbone compounds). Modified antisense compounds also contained sugar moiety substitutions at the 2' position, comprising a 2'-methoxyethyl (2'-MOE) or a 2'-O-dimethylaminoethoxyethyl (2'-DMAEOE). Further modifications included nucleobase substitutions, wherein the unmodified cytosine nucleobase was used in place of the modified 5-methylcytosine at one position in the antisense compound. The compounds are shown in Table 1.

ISIS 145733 (SEQ ID NO: 4), ISIS 145742 (SEQ ID NO: 5) and ISIS 145746 (SEQ ID NO: 6) are chimeric oligonucleotides having 2'-MOE wings and a deoxy gap with phosphorothioate linkages throughout the oligonucleotide. ISIS 257016 (SEQ ID NO: 4), ISIS 341699 (SEQ ID NO: 5) and ISIS 351642 (SEQ ID NO: 6) are chimeric oligonucleotides having 2'-MOE wings and a deoxy gap, with phosphodiester linkages in the wings and phosphorothioate linkages in the gap. ISIS 351641 (SEQ ID NO: 4), ISIS 360886 (SEQ ID NO: 4) and ISIS 360887 (SEQ ID NO: 4) are chimeric oligonucleotides having 2'-MOE wings and a deoxy gap, with phosphorothioate linkages in the gap and phosphodiester linkages in the wings, except for one phosphorothioate linkage in the wing(s) at either the extreme 5' end (ISIS 360886), the extreme 3' end (ISIS 360887) or both of the extreme 5' and 3' ends (ISIS 351641).

ISIS 323294 (SEQ ID NO: 4) consists of 2'-MOE nucleotides at positions 1,2,3,4,17 and 19, 2'-DMAEOE nucleotides at positions 5, 16,18 and 20 and 2'-deoxynucleotides at positions 6 through 15, with phosphorothioate linkages throughout the oligonucleotide. ISIS 323295 (SEQ ID NO: 4) consists of 2'-MOE nucleotides at positions 1,2,3,4,17 and 19, 2'-DMAEOE nucleotides at positions 5, 16,18 and 20 and 2'-deoxynucleotides at positions 6 through 15, wherein the first and last 4 internucleoside linkages are phosphodiester and the central internucleoside linkages are phosphorothioate.

The nucleotides in the 3' most positions in ISIS 251017 and 257018 are cytosine residues (indicated by an asterisk in Table 4). All other cytosine residues of the oligonucleotides listed above are 5-methylcytosines. The compounds are shown in Table 1. Phosphodiester (P=O) internucleoside linkages are indicated by an "o" between nucleotide positions. Phosphorothioate (P=S) internucleoside linkages are indicated by an "s" between nucleotide positions. 2'-MOE nucleotides are underscored and 2'-DMAEOE nucleotides are emboldened. All compounds in Table 1 target the coding region of murine SGLT2 (provided herein as SEQ ID NO: 7).

TABLE 1

Chemical modifications of antisense compounds targeting SGLT2

| ISIS # | Sequence | SEQ ID NO |
|---|---|---|
| 145733 | GsAsAsGsTsAsGsCsCsAsCsCsAsAsCsTsGsTsGsC | 4 |
| 257016 | GoAoAoGoTsAsGsCsCsAsCsCsAsAsCsToGoToGoC | 4 |
| 257017 | GsAsAsGsTsAsGsCsCsAsCsCsAsAsCsTsGsTsGsC* | 4 |
| 257018 | GoAoAoGoTsAsGsCsCsAsCsCsAsAsCsToGoToGoC* | 4 |
| 145742 | GsAsGsAsAsCsAsTsAsTsCsCsAsCsCsGsAsGsAsT | 5 |
| 341699 | GoAoGoAoAsCsAsTsAsTsCsCsAsCsCsGoAoGoAoT | 5 |
| 145746 | CsTsGsCsAsCsAsGsTsGsTsCsTsGsTsGsTsAsCsA | 6 |
| 351642 | CoToGoCoAsCsAsGsTsGsTsCsTsGsTsGoToAoCoA | 6 |
| 351641 | GsAoAoGoTsAsGsCsCsAsCsCsAsAsCsToGoToGsC | 4 |
| 360886 | GsAoAoGoTsAsGsCsCsAsCsCsAsAsCsToGoToGoC | 4 |
| 360887 | GoAoAoGoTsAsGsCsCsAsCsCsAsAsCsToGoToGsC | 4 |
| 323294 | GsAsAsGsTsAsGsCsCsAsCsCsAsAsCsTsGsTsGsC | 4 |
| 323295 | GoAoAoGoTsAsGsCsCsAsCsCsAsAsCsToGoToGoC | 4 |

Example 14

Antisense Inhibition of SGLT2 in Murine Kidney: Comparison of Various Oligonucleotide Chemistries In accordance with the present invention, modified SGLT2 antisense compounds were investigated for their activity in vivo. ISIS 29837 (TCGATCTCCTTTTATGCCCG, SEQ ID NO: 8) served as a control compound and is a chimeric oligonucleotide ("gapmer") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. The internucleoside (backbone) linkages are phosphorothioate (P=S) throughout the oligonucleotide. All cytidine residues are 5-methylcytidines.

Male 6-week old Balb/c mice (Charles River Laboratories, Wilmington, Mass.) were given intraperitoneal injections of ISIS 145733, ISIS 257016, ISIS 323294, ISIS 323295 or ISIS 29837 at a dose of 25 mg/kg twice per week for two weeks. Saline-injected animals served as controls. Each treatment group contained four animals. The mice were sacrificed 2 days following administration of the fourth and final dose of oligonucleotide or saline.

Mice were evaluated for SGLT2 levels in kidney. Target levels were determined by quantitative real-time PCR as described by other examples herein. PCR results were normalized to the ubiquitously expressed mouse cyclophilin A gene.

Probes and primers to mouse SGLT2 were designed to hybridize to a mouse SGLT2 sequence, using published sequence information (incorporated herein as SEQ ID NO: 7). For mouse SGLT2 the PCR primers were:
forward primer: CTCGTCTCATACCCGAGTTCTTCT (SEQ ID NO: 9)
reverse primer: AATGATGGCGAAATAGAGGTAGTGTAC (SEQ ID NO: 10) and the PCR probe was: FAM-TGCGAC-CCTCAGCGTGCCC-TAMRA (SEQ ID NO: 11) where FAM is the fluorescent dye and TAMRA is the quencher dye.
For mouse cyclophilin A the PCR primers were:
forward primer: TCGCCGCTTGCTGCA (SEQ ID NO: 12)
reverse primer: ATCGGCCGTGATGTCGA (SEQ ID NO: 13) and the PCR probe was: 5' JOE-CCATGGTCAAC-CCCACCGTGTTC-3' (SEQ ID NO: 14) where JOE is the fluorescent reporter dye and TAMRA is the quencher dye.

The data are expressed as percent change ("−" indicates a decrease) relative to saline treated animals and are shown in Table 2.

TABLE 2

Antisense inhibition of SGLT2 mRNA expression in vivo by modified SGLT2 antisense compounds
Percent change in SGLT2 expression relative to saline

| ISIS 145733 | ISIS 257016 | ISIS 323294 | ISIS 323295 | ISIS 29837 |
|---|---|---|---|---|
| −44 | −82 | −40 | −31 | −23 |

These data illustrate that antisense compounds of different chemistries inhibit the expression of SGLT2 mRNA in mouse kidney. Greatest inhibition of SGLT2 is observed in kidneys from mice treated with ISIS 257016, which is a mixed backbone antisense compound.

Mice were further evaluated for total body weight, liver weight and spleen weight. Significant changes in spleen, liver or body weight can indicate that a particular compound causes toxic effects. The data are expressed as percent change in body or organ weight ("+" indicates an increase, "−" indicates a decrease). The results are presented in Table 3.

TABLE 3

Effects of antisense compounds on total body weight, liver weight and spleen weight in mice

| | Percent change in weight | | | | |
|---|---|---|---|---|---|
| | 145733 | 257016 | 323294 | 323295 | 29837 |
| Total Body | 0 | 0 | −1 | −3 | 0 |
| Liver | +1 | +1 | +9 | +4 | +12 |
| Spleen | +4 | +1 | +19 | +8 | +1 |

All changes in body weight and organ weight were within the margin of error of the experiment. No significant changes in body weight were observed during the treatment or at study termination. No significant changes in liver or spleen weights were observed.

Toxic effects of compounds administered in vivo can also be assessed by measuring the levels of enzymes and proteins associated with disease or injury of the liver or kidney. Elevations in the levels of the serum transaminases aspartate aminotransferase (AST) and alanine aminotransferase (ALT) are often indicators of liver disease or injury. Serum total bilirubin is an indicator of liver and biliary function, and albumin and blood urea nitrogen (BUN) are indicators of renal function. Glucose and triglyceride levels are sometimes altered due to toxicity of a treatment. Serum glucose also depends in part upon the activity of SGLT2.

In accordance with the present invention, the levels of ALT, AST, total bilirubin, albumin, BUN, glucose and triglyceride were measured in mice treated with the compounds of the invention. Serum was analyzed by LabCorp Testing Facility (San Diego, Calif.). The results are expressed as units measured and are shown in Table 4.

treated animals. Heart sections from animals treated with ISIS 323294 and ISIS 323295 showed a high amount of inflammation relative to hearts from saline-treated mice. 2E1-B5 antibody was recognized using an isospecific anti-IgG2 horse-radish peroxidase-conjugated secondary antibody (Zymed, San Francisco, Calif.) and immunostaining was developed with 3,3'-diaminobenzidene (DAKO, Carpenteria, Calif.). 2E1-B5 staining was performed in duplicate and showed that none of the chemistries significantly stained the liver, while staining was observed in the kidney proximal tubules.

The results illustrated in this example demonstrate that antisense compounds of different chemistries are delivered to the kidney, reduce SGLT2 expression in vivo, and that treatment with these compounds does not result in liver or kidney toxicity. The mixed backbone compound, ISIS 257016, is particularly efficient at reducing target mRNA levels in the kidney.

TABLE 4

Effects of antisense compounds targeting SGLT2 on liver and kidney function in mice

| Serum indicator | Normal Range | Treatment and units measured | | | | | |
|---|---|---|---|---|---|---|---|
| | | Saline | 145733 | 257016 | 323294 | 323295 | 29837 |
| BUN mg/dL | 15-40 | 27 | 29 | 33 | 29 | 30 | 30 |
| Albumin g/dL | 2.5-4.0 | 3 | 3 | 3 | 3 | 3 | 3 |
| Bilirubin mg/dL | 0.1-1.0 | 0.1 | 0.1 | 0.1 | 0.1 | 0.1 | 0.1 |
| AST IU/L | 30-300 | 124 | 83 | 129 | 174 | 89 | 114 |
| ALTI U/L | 30-200 | 33 | 26 | 47 | 61 | 32 | 31 |
| Triglycerides mg/dL | 25-100* | 179 | 154 | 157 | 160 | 209 | 198 |
| Glucose mg/dL | 80-150* | 242 | 270 | 222 | 284 | 271 | 235 |

*Triglyceride and glucose levels are routinely higher in the Balb/c strain of mice than in other strains of mice.

The levels of routine clinical indicators of liver and kidney injury and disease are within normal ranges and are not significantly changed relative to saline-treated animals, demonstrating that the compounds of the invention do not significantly affect renal or hepatic function. Triglyceride and glucose levels, while outside the normal range for most mice as is common in the Balb/c strain, are not significantly elevated relative to saline-treated animals.

Mice injected with ISIS 145733, ISIS 257016, ISIS 323294 and ISIS 323295 were also evaluated histologically following routine procedures. Liver, spleen, kidney, intestine, pancreas, lung, skin, heart and muscle samples were procured, fixed in 10% neutral-buffered formalin and processed for staining with hematoxylin and eosin, to visualize nuclei and cytoplasm, or with the anti-oligonucleotide IgG1 antibody 2E1-B5 (Berkeley Antibody Company, Berkeley, Calif.) to assess oligonucleotide staining patterns. Hematoxylin and eosin staining in most tissues exhibited no significant difference between saline- and oligonucleotide- Example 15

Antisense Inhibition of SGLT2 mRNA Expression In Vivo: Dose Response Study Comparing Mixed Backbone and Full Phosphorothioate Backbone Compounds ISIS 145733 and ISIS 257016 were selected for a dose response study in mice to further evaluate the effectiveness of mixed backbone antisense compounds for kidney targeting. Male 8-week old Balb/c mice (Charles River Laboratories, Wilmington, Mass.) were given intraperitoneal injections of ISIS 145733 or ISIS 257016 at doses of 6.25, 12.5, 25 or 50 mg/kg twice per week for two weeks. Saline-injected animals served as controls. A total of 4 animals were injected per group. The mice were sacrificed 2 days following administration of the fourth and final dose of oligonucleotide or saline.

Mice were evaluated for SGLT2 levels in kidney. Target levels were determined by quantitative real-time PCR as described in other examples herein. PCR results were normalized to cyclophilin as described in Example 14. The data are expressed as percent change ("+" indicates an increase, "−" indicates a decrease) relative to saline treated animals and are illustrated in Table 5.

TABLE 5

Antisense inhibition of SGLT2 mRNA expression in vivo
by antisense compounds with varying chemistries

| Dose of oligonucleotide mg/kg | Percent change in SGLT2 expression relative to saline | |
|---|---|---|
| | ISIS 145733 | ISIS 257016 |
| 6.25 | −3 | −58 |
| 12.5 | −7 | −68 |
| 25 | −37 | −68 |
| 50 | −34 | −77 |

These results illustrate that the compounds of the invention, both full phosphorothioate and mixed backbone oligonucleotides, inhibit the expression of SGLT2 in vivo in a dose-dependent manner. However, treatment with the mixed backbone oligonucleotide, ISIS 257016, resulted in the greatest reduction of target mRNA levels.

The levels of SGLT2 expression were also evaluated by Northern blot analysis of both pooled and individual RNA samples, to validate the target reduction observed by real-time PCR. Total RNA was prepared from procured tissues of sacrificed mice by homogenization in GITC buffer (Invitrogen, Carlsbad, Calif.) containing 2-mercaptoethanol (Sigma-Aldrich, St. Louis, Mo.) following manufacturer's recommended protocols followed by ultracentrifugation through a CsCl cushion. Twenty micrograms of total RNA was fractionated by electrophoresis through 1.2% agarose gels containing 1.1% formaldehyde using a MOPS buffer system (AMRESCO, Inc. Solon, Ohio). RNA was transferred from the gel to HYBOND™-N+ nylon membranes (Amersham Pharmacia Biotech, Piscataway, N.J.) by overnight capillary transfer. RNA transfer was confirmed by UV visualization. Membranes were fixed by UV cross-linking using a STRATALINKER™ UV Crosslinker 2400 (Stratagene, Inc, La Jolla, Calif.) and then probed using RapidHYB™ hybridization solution (Amersham Pharmacia Biotech, Piscataway, N.J.) using manufacturer's recommendations for stringent conditions.

To detect mouse SGLT2, a mouse SGLT2 specific template was prepared by PCR using the forward primer 5'-ATGGAG-CAACACGTAGAGGCAGGCT-3' (SEQ ID NO: 15) and the reverse primer 5'-GAGTGCCGCCAGCCCTCCTGT-CACA-3' (SEQ ID NO: 16) and gel purified. The probe was prepared by asymmetric PCR with the purified template and the reverse primer incorporating $^{32}$P CTP to label the probe. Following hybridization blots were exposed overnight to phosphorimager screens (Molecular Dynamics, Amersham) and quantitated. To normalize for variations in loading and transfer efficiency membranes were stripped and probed for mouse glyceraldehyde-3-phosphate dehydrogenase (GAPDH) RNA (Clontech, Palo Alto, Calif.).

For pooled sample analysis, equal amounts of RNA isolated from the kidneys of mice in the same treatment was combined for a total of 20 μg, and the pooled sample was subjected to Northern blot analysis. The results of the pooled sample analysis are shown in Table 6 and are normalized to saline controls ("+" indicates an increase, "−" indicates a decrease).

TABLE 6

Northern Analysis of SGLT2 message
in pooled kidney RNA samples

| Dose of oligonucleotide mg/kg | Percent change in SGLT2 expression relative to saline | |
|---|---|---|
| | ISIS 145733 | ISIS 257016 |
| 6.25 | +21 | −57 |
| 12.5 | +7 | −50 |
| 25 | −35 | −75 |
| 50 | −35 | −82 |

These results demonstrate that, as determined by Northern blot analysis of pooled samples, ISIS 257016 inhibits SGLT2 expression inhibits SGLT2 expression at all doses of antisense compound in a dose-dependent manner, whereas ISIS 145733 inhibits SLGT2 expression at the two highest doses of antisense compound.

Target levels in kidney RNA samples from individual mice were also measured by Northern blot analysis. Equal amounts of RNA were individually subjected to Northern blot analysis to determine the level of SGLT2. Target level measurements for each treatment group were then averaged. The results are shown in Table 7 and are normalized to saline controls ("−" indicates a decrease).

TABLE 7

Northern Analysis of SGLT2 message in
individually measured RNA samples

| Dose of oligonucleotide mg/kg | Percent change in SGLT2 expression relative to saline | |
|---|---|---|
| | ISIS 145733 | ISIS 257016 |
| 6.25 | −34 | −66 |
| 12.5 | −38 | −68 |
| 25 | −39 | −74 |
| 50 | −59 | −82 |

These results again show that treatment with mixed backbone compound ISIS 257016 results in greater inhibition of SGLT2 mRNA expression in the kidney relative to treatment with a full phosphorothioate backbone compound.

Treated mice were further evaluated at the end of the treatment period for total body, liver and spleen weight. The data are expressed as percent change in body or organ weight ("+" indicates an increase, "−" indicates a decrease). The results are presented in Table 8.

TABLE 8

Effects of modified antisense compounds on total body
weight, liver weight and spleen weight in mice

| | Percent change in weight | | | | | |
|---|---|---|---|---|---|---|
| Dose of | ISIS 145733 | | | ISIS 257016 | | |
| oligonucleotide mg/kg | Total Body | Liver | Spleen | Total Body | Liver | Spleen |
| 6.25 | −4 | −10 | −12 | −1 | −3 | +1 |
| 12.5 | −6 | −2 | −7 | −3 | −13 | −9 |

TABLE 8-continued

Effects of modified antisense compounds on total body weight, liver weight and spleen weight in mice

| Dose of oligonucleotide mg/kg | Percent change in weight | | | | | |
|---|---|---|---|---|---|---|
| | ISIS 145733 | | | ISIS 257016 | | |
| | Total Body | Liver | Spleen | Total Body | Liver | Spleen |
| 25 | 1 | −1 | +10 | 1 | −8 | +8 |
| 50 | −1 | +6 | +10 | −3 | −9 | +12 |

These data demonstrate that no significant changes in total body, liver or spleen weights are observed following treatment with ISIS 145733 or ISIS 257016 at 4 different doses. No changes in total body weight were observed during the treatment period, or at study termination.

In addition to the indicators of toxicity listed in Example 14, creatinine levels are also used to evaluate renal function. In accordance with the present invention, the levels of ALT, AST, total bilirubin, creatinine, BUN, glucose and triglyceride were measured in mice treated with the compounds of the invention. Serum was analyzed by LabCorp Testing Facility (San Diego, Calif.). The results are expressed as units measured and are shown in Table 9.

TABLE 9

Effects of modified antisense compounds targeting SGLT2 on liver and kidney function in mice

| | | Units measured per treatment and dose | | | | |
|---|---|---|---|---|---|---|
| Serum indicator | Normal Range | Saline | 145733 25 mg/kg | 145733 50 mg/kg | 257016 25 mg/kg | 257016 50 mg/kg |
| BUN mg/dL | 15-40 | 24 | 24 | 25 | 26 | 26 |
| Creatinine mg/L | 0.0-1.0 | 0.1 | 0.1 | 0.1 | 0.1 | 0.1 |
| Bilirubin mg/dL | 0.1-1.0 | 0.1 | 0.1 | 0.1 | 0.1 | 0.1 |
| AST IU/L | 30-300 | 77 | 65 | 96 | 133 | 141 |
| ALT IU/L | 30-200 | 24 | 18 | 22 | 34 | 35 |
| Triglycerides mg/dL | 25-100* | 165 | 169 | 230 | 130 | 111 |
| Glucose mg/dL | 80-150* | 236 | 280 | 256 | 244 | 248 |

*Triglyceride and glucose levels are routinely higher in the Balb/c strain of mice than in other strains of mice.

The ALT levels in animals treated with either 25 mg/kg or 50 mg/kg of ISIS 145733 are slightly below the normal range, as is the ALT level for saline treated mice. Otherwise, the levels of routine clinical indicators of liver and kidney injury and disease are within normal ranges and are not significantly changed relative to saline-treated animals, demonstrating that the compounds of the invention do not significantly affect renal or hepatic function. Triglyceride and glucose levels, while outside the normal range as is common in the Balb/c strain, are not significantly elevated relative to saline-treated animals.

Mice injected with ISIS 145733 and ISIS 257016 at doses from 6.25 to 50 mg/kg also were evaluated histologically following routine procedures. Liver and kidney samples were procured, fixed in 10% neutral-buffered formalin and processed for staining with hematoxylin and eosin or with the anti-oligonucleotide IgG1 antibody 2E1-B5 (Berkeley Antibody Company, Berkeley, Calif.) as described in other examples herein. Hematoxylin and eosin staining exhibited no significant difference between saline- and oligonucleotide-treated animals. 2E1 staining showed no detectable oligonucleotide in the liver, while staining was observed in the kidney proximal tubules. Staining intensity lessened concomitantly with a decrease in oligonucleotide dose.

The results illustrated in this example demonstrate that antisense compounds of different chemistries are delivered to the kidney, reduce SGLT2 expression in vivo in a dose-dependent manner, and that treatment with these compounds does not result in liver or kidney toxicity. The results further demonstrate that mixed backbone compound ISIS 257016 is particularly effective at reducing target mRNA levels in the kidney.

Example 16

Antisense Inhibition of SGLT2 mRNA Expression In Vivo: a Second Dose Response Study Comparing Mixed Backbone and Full Phosphorothioate Backbones ISIS 145733 and ISIS 257016 were selected for a dose response study in mice using two identical and two lower doses with respect to the doses used in Example 15.

Male 8-week old Balb/c mice (Charles River Laboratories, Wilmington, Mass.) were given intraperitoneal injections of ISIS 145733 or ISIS 257016 at doses of 1, 5, 25 or 50 mg/kg twice per week for two weeks. Saline-injected animals served as controls. Each treatment group contained 4 mice. The mice were sacrificed 2 days following administration of the fourth and final dose of oligonucleotide or saline.

Mice were evaluated for SGLT2 levels in kidney and liver. Target levels were determined by quantitative real-time PCR as described by other examples herein. PCR results were normalized to cyclophilin. The data are expressed as percent change relative to saline treated animals ("+" indicates an increase, "−" indicates a decrease) and are illustrated in Table 10.

TABLE 10

Antisense inhibition of SGLT2 mRNA expression in vivo
by antisense compounds with varying chemistries

| Dose of oligonucleotide mg/kg | Percent change in SGLT2 expression relative to saline | | | |
|---|---|---|---|---|
| | Kidney | | Liver | |
| | ISIS 145733 | ISIS 257016 | ISIS 145733 | ISIS 257016 |
| 1 | +2 | −46 | −19 | +13 |
| 5 | −15 | −64 | −39 | +1 |
| 25 | −34 | −74 | −21 | −5 |
| 50 | −40 | −76 | −59 | −12 |

These results illustrate that the compounds of the invention, both full phosphorothioate and mixed backbone oligonucleotides, can inhibit the expression of kidney SGLT2 in a dose-dependent manner. Greater inhibition is observed in kidneys from mice treated with ISIS 257016, a mixed backbone antisense compound. SGLT2 is not highly expressed in liver, therefore target levels are low before treatment and therefore more difficult to accurately measure. ISIS 145733 and ISIS 257016 lowered liver SGLT2 expression, with 145733 having a greater effect in liver than the mixed backbone ISIS 257016.

Treated mice were further evaluated for liver and spleen weight. The data are expressed as percent change in body or organ weight ("+" indicates an increase, "−" indicates a decrease). The results are presented in Table 11.

TABLE 11

Effects of antisense compounds on total body
weight, liver weight and spleen weight in mice

| Dose of oligonucleotide mg/kg | Percent change in weight | | | | | |
|---|---|---|---|---|---|---|
| | ISIS 145733 | | | ISIS 257016 | | |
| | Total Body | Liver | Spleen | Total Body | Liver | Spleen |
| 1 | 0 | −6 | +10 | −2 | −8 | +13 |
| 5 | +3 | +1 | +10 | −3 | −9 | +5 |
| 25 | −1 | +2 | −4 | +2 | +2 | +12 |
| 50 | −1 | +13 | +35 | −2 | −6 | +15 |

No significant change was observed in total body weight at timepoints throughout or at the termination of the study. All changes in liver and spleen weight were within the margin of error for the data and are therefore not significant.

In addition to the other serum markers described herein, cholesterol levels can be used as a measure of toxicity. In accordance with the present invention, the levels of ALT, AST, total bilirubin, albumin, creatinine, BUN, triglyceride, cholesterol and glucose were measured in mice treated with the compounds of the invention. Plasma samples were analyzed using the Olympus AU400e automated chemistry analyzer (Olympus America, Irving, Tex.). The results, expressed as units measured, are shown for ISIS 145733 in Table 12 and for ISIS 257016 in Table 13.

TABLE 12

Effect of the full phosphorothioate antisense compound
ISIS 145733 on indicators of liver and kidney function

| Serum indicator | Normal Range | Saline | Units measured per dose of ISIS 145733 | | | |
|---|---|---|---|---|---|---|
| | | | 1 mg/kg | 5 mg/kg | 25 mg/kg | 50 mg/kg |
| BUN mg/dL | 15-40 | 27 | 31 | 31 | 30 | 25 |
| Creatinine mg/L | 0.0-1.0 | 0.2 | 0.2 | 0.2 | 0.2 | 0.2 |
| Bilirubin mg/dL | 0.1-1.0 | 0.3 | 0.2 | 0.1 | 0.3 | 0.1 |
| AST IU/L | 30-300 | 92 | 91 | 45 | 133 | 56 |
| ALT IU/L | 30-200 | 35 | 27 | 26 | 37 | 31 |
| Albumin g/dL | 2.5-4.0 | 3 | 3 | 3 | 3 | 3 |
| Triglycerides mg/dL | 25-100* | 136 | 188 | 183 | 153 | 224 |
| Cholesterol mg/dL | 70-125 | 122 | 116 | 117 | 120 | 132 |
| Glucose mg/dL | 80-150* | 208 | 202 | 173 | 170 | 161 |

TABLE 13

Effect of the mixed backbone antisense compound ISIS
257016 on indicators of liver and kidney function

| Serum indicator | Normal Range | Saline | Units measured per dose of ISIS 257016 | | | |
|---|---|---|---|---|---|---|
| | | | 1 mg/kg | 5 mg/kg | 25 mg/kg | 50 mg/kg |
| BUN mg/dL | 15-40 | 27 | 23 | 29 | 25 | 28 |
| Creatinine mg/L | 0.0-1.0 | 0.2 | 0.2 | 0.2 | 0.2 | 0.2 |
| Bilirubin mg/dL | 0.1-1.0 | 0.3 | 0.2 | 0.2 | 0.2 | 0.2 |
| AST IU/L | 30-300 | 92 | 74 | 73 | 99 | 138 |
| ALT IU/L | 30-200 | 35 | 34 | 34 | 46 | 48 |
| Albumin g/dL | 2.5-4.0 | 3 | 3 | 3 | 3 | 3 |
| Triglycerides mg/dL | 25-100* | 136 | 271 | 233 | 225 | 136 |
| Cholesterol mg/dL | 70-125 | 122 | 116 | 124 | 144 | 137 |
| Glucose mg/dL | 80-150* | 208 | 180 | 178 | 154 | 182 |

*Triglyceride and glucose levels are routinely higher in the Balb/c strain of mice than in other strains of mice.

Cholesterol levels of animals treated with either 25 or 50 mg/kg of ISIS 257016 were slightly above the normal range; however, they are not significantly greater than saline control animals given the margin of error for the experiment. The levels of routine clinical indicators of liver and kidney injury and disease are within normal ranges and are not significantly changed relative to saline-treated animals, demonstrating that the compounds of the invention do not significantly affect renal or hepatic function. Triglyceride and glucose levels, while outside the normal range as is common in the Balb/c strain, are not significantly elevated relative to saline-treated animals.

Mice injected ISIS 145733 and ISIS 257016 at 1-50 mg/kg also were evaluated histologically following routine procedures. Liver and kidney samples were procured, fixed in 10% neutral-buffered formalin and processed for staining with hematoxylin and eosin or with the anti-oligonucleotide IgG1 antibody 2E1-B5 (Berkeley Antibody Company, Berkeley, Calif.). Hematoxylin and eosin staining in most tissues exhibited no significant difference between saline- and 145733-treated animals, with the exception of slight inflammatory cell infiltration in the liver tissue. Livers from mice treated with ISIS 257016 showed evidence of nuclear degradation and mitosis at 50 mg/kg and slight mitosis at 25 mg/kg. Kidneys from mice treated with ISIS 257016 exhibited no significant differences compared to saline-treated kidneys. Staining with the 2E1 antibody showed weak staining in liver and kidneys from animals treated with ISIS 145733, whereas staining was strong in liver and kidney from animals treated with ISIS 257016. Kidney 2E1 staining appears in a punctuate pattern.

The results illustrated in this example demonstrate that antisense compounds of different chemistries are delivered to the kidney, reduce SGLT2 expression in vivo in a dose-dependent manner, and that treatment with these compounds does not result in liver or kidney toxicity. The results further demonstrate that mixed backbone compound ISIS 257016 is particularly effective, even at low doses, at reducing target mRNA levels in the kidney.

Example 17

Dose Response Study Comparing Mixed Backbone and Full Phosphorothioate Backbones: a Second SGLT2 Antisense Sequence A second mixed backbone SGLT2 oligonucleotide, ISIS 341699 (SEQ ID NO: 5), and control phosphorothioate SGLT2 oligonucleotide, ISIS 145742 (SEQ ID NO: 5), were selected for a dose response study in mice. For comparison, ISIS 257016 (mixed backbone) also was included in this study.

Male 8-week old Balb/c mice (Charles River Laboratories, Wilmington, Mass.) were given intraperitoneal injections of ISIS 341699, ISIS 145742 or ISIS 257016 twice per week for two weeks with the doses shown in Table 14. Saline-injected animals served as controls. Each treatment group contained 4 mice. The mice were sacrificed 2 days following administration of the fourth and final dose of oligonucleotide or saline.

Mice were evaluated for SGLT2 levels in kidney. Target levels were determined by quantitative real-time PCR as described by other examples herein. PCR results were normalized to cyclophilin. The data are expressed as percent change relative to saline treated animals ("+" indicates an increase, "−" indicates a decrease) and are illustrated in Table 14.

TABLE 14

Antisense inhibition of SGLT2 mRNA expression in vivo by mixed backbone and full phosphorothioate oligonucleotides (expressed as percent change in SGLT2 mRNA expression relative to saline)

| Dose of oligonucleotide mg/kg | ISIS 145742 | ISIS 341699 | ISIS 257016 |
|---|---|---|---|
| 0.2 | — | — | −18.9 |
| 1 | — | −1.8 | −50.5 |
| 5 | −0.6 | −10.9 | −56.7 |
| 25 | −24.9 | −23.9 | — |
| 50 | −32.6 | — | — |

These results illustrate that the compounds of the invention, both full phosphorothioate and mixed backbone oligonucleotides, can inhibit the expression of kidney SGLT2 in a dose-dependent manner. However, lower doses of the mixed backbone compound are required to inhibit SGLT2 expression in kidneys from treated mice.

Treated mice were further evaluated for liver and spleen weight. The data are expressed as percent change in body or organ weight ("+" indicates an increase, "−" indicates a decrease). The results are presented in Table 15 and Table 16.

TABLE 15

Effects of antisense compounds on total body weight of mice (expressed as percent change in body weight)

| Dose of oligonucleotide mg/kg | ISIS 145742 | ISIS 341699 | ISIS 257016 |
|---|---|---|---|
| 0.2 | — | — | +7.9 |
| 1 | — | +5.7 | +5.8 |
| 5 | +5.0 | +5.8 | +3.2 |
| 25 | +2.0 | +2.5 | — |
| 50 | +7.2 | — | — |

TABLE 16

Effects of antisense compounds on liver weight and spleen weight of mice (expressed as percent change in organ weight)

| Dose of oligonucleotide mg/kg | Liver | | | Spleen | | |
|---|---|---|---|---|---|---|
| | ISIS 145742 | ISIS 341699 | ISIS 257016 | ISIS 145742 | ISIS 341699 | ISIS 257016 |
| 0.2 | — | — | −6.0 | — | — | −4.7 |
| 1 | — | +2.3 | +14.9 | — | −4.2 | +1.4 |
| 5 | +7.1 | +2.2 | +7.0 | +10.6 | −2.8 | −7.6 |
| 25 | +7.2 | +5.8 | — | +0.8 | −0.2 | — |
| 50 | +12.1 | — | — | +9.4 | — | — |

No significant change was observed in total body weight, liver weight or spleen weight at timepoints throughout or at the termination of the study.

Levels of BUN, creatinine, AST, ALT, albumin, triglycerides, cholesterol and glucose were measured in mice treated with the compounds of the invention. Plasma samples were analyzed using the Olympus AU400e automated chemistry analyzer (Olympus America, Irving, Tex.). The results, expressed as units measured, are shown for ISIS 145742 in Table 17, ISIS 341699 in Table 18 and ISIS 257016 in Table 19.

TABLE 17

Effect of the full phosphorothioate antisense compound ISIS 145742 on indicators of liver and kidney function

| Serum indicator | Normal Range | Saline | Units measured per dose of ISIS 145742 | | |
|---|---|---|---|---|---|
| | | | 5 mg/kg | 25 mg/kg | 50 mg/kg |
| BUN mg/dL | 15-40 | 20 | 21.3 | 25.5 | 20.8 |
| Creatinine mg/L | 0.0-1.0 | 0.1 | 0.2 | 0.2 | 0.2 |
| AST IU/L | 30-300 | 113 | 75.3 | 83.5 | 145.3 |
| ALT IU/L | 30-200 | 35.5 | 29.8 | 40.3 | 47.5 |

TABLE 17-continued

Effect of the full phosphorothioate antisense compound ISIS 145742 on indicators of liver and kidney function

| Serum indicator | Normal Range | Saline | Units measured per dose of ISIS 145742 | | |
|---|---|---|---|---|---|
| | | | 5 mg/kg | 25 mg/kg | 50 mg/kg |
| Albumin g/dL | 2.5-4.0 | 3.0 | 3.0 | 2.9 | 2.9 |
| Triglycerides mg/dL | 25-100* | 223.8 | 176.5 | 192 | 176.8 |
| Cholesterol mg/dL | 70-125 | 129 | 119.5 | 119.5 | 113.5 |
| Glucose mg/dL | 80-150* | 176.5 | 196.5 | 192 | 194.8 |

TABLE 18

Effect of mixed backbone antisense compound ISIS 341699 on indicators of liver and kidney function

| Serum indicator | Normal Range | Saline | Units measured per dose of ISIS 341699 | | |
|---|---|---|---|---|---|
| | | | 1 mg/kg | 5 mg/kg | 25 mg/kg |
| BUN mg/dL | 15-40 | 20 | 20 | 21.8 | 22 |
| Creatinine mg/L | 0.0-1.0 | 0.1 | 0.2 | 0.2 | 0.2 |
| AST IU/L | 30-300 | 113 | 78.2 | 119 | 64.8 |
| ALT IU/L | 30-200 | 35.5 | 36.2 | 37.3 | 33.0 |
| Albumin g/dL | 2.5-4.0 | 3.0 | 3.3 | 3.1 | 3.2 |
| Triglycerides mg/dL | 25-100* | 223.8 | 206.4 | 186.8 | 183.5 |
| Cholesterol mg/dL | 70-125 | 129 | 135 | 124 | 120.8 |
| Glucose mg/dL | 80-150* | 176.5 | 203.2 | 171.5 | 197 |

TABLE 19

Effect of mixed backbone antisense compound ISIS 257016 on indicators of liver and kidney function

| Serum indicator | Normal Range | Saline | Units measured per dose of ISIS 257016 | | |
|---|---|---|---|---|---|
| | | | 0.2 mg/kg | 1 mg/kg | 5 mg/kg |
| BUN mg/dL | 15-40 | 20 | 21.8 | 26.3 | 20.5 |
| Creatinine mg/L | 0.0-1.0 | 0.1 | 0.2 | 0.2 | 0.2 |
| AST IU/L | 30-300 | 113 | 123.8 | 85.3 | 69.5 |
| ALT IU/L | 30-200 | 35.5 | 36.8 | 44 | 43 |
| Albumin g/dL | 2.5-4.0 | 3.0 | 3.1 | 3.4 | 3.1 |
| Triglycerides mg/dL | 25-100* | 223.8 | 138.8 | 268.3 | 212.8 |
| Cholesterol mg/dL | 70-125 | 129 | 128 | 152 | 135.3 |
| Glucose mg/dL | 80-150* | 176.5 | 208.8 | 212.3 | 164.5 |

*Triglyceride and glucose levels are routinely higher in the Balb/c strain of mice than in other strains of mice.

In some oligonucleotide-treated animals cholesterol levels were above the normal range; however, this elevation is not significant since saline-treated animals also exhibited cholesterol above the normal range. The levels of the remaining routine clinical indicators of liver and kidney injury and disease are within normal ranges and are not significantly changed relative to saline-treated animals, demonstrating that the compounds of the invention do not significantly affect renal or hepatic function. Triglyceride and glucose levels, while outside the normal range as is common in the Balb/c strain, are not significantly elevated relative to saline-treated animals.

Mice injected with ISIS 145742, ISIS 341699 and ISIS 257016 at 0.2-50 mg/kg were also evaluated histologically following routine procedures. Liver and kidney samples were procured, fixed in 10% neutral-buffered formalin and processed for staining with hematoxylin and eosin or with the anti-oligonucleotide IgG1 antibody 2E1-B5, as described in other examples herein. Hematoxylin and eosin staining in both liver and kidney tissues exhibited no significant difference between saline- and antisense oligonucleotide-treated animals. Staining with the 2E1 antibody showed high background in sinusoidal tissues of liver from the saline-injected animals, therefore making it difficult to interpret positive staining in the oligonucleotide-treated livers. Kidney samples from saline-injected animals and animals treated with 0.2 mg/kg ISIS 257016 showed no positive oligonucleotide staining; however, the remainder of the oligonucleotide-treated animals demonstrated high levels of staining in the proximal tubules., which increased with dose.

The results illustrated in this example demonstrate that antisense compounds of different chemistries are delivered to the kidney, reduce SGLT2 expression in vivo in a dose-dependent manner, and that treatment with these compounds does not result in liver or kidney toxicity. The results further demonstrate that mixed backbone compounds ISIS 341699 and ISIS 257016 are particularly effective at reducing target mRNA levels in the kidney.

Example 18

Dose Response Study Comparing Mixed Backbone and Full Phosphorothioate Backbones: a Third SGLT2 Antisense Sequence A third mixed backbone SGLT2 oligonucleotide, ISIS 351642 (SEQ ID NO: 6), and control phosphorothioate SGLT2 oligonucleotide, ISIS 145746 (SEQ ID NO: 6), were selected for a dose response study in mice.

Male 7-week old Balb/c mice (Charles River Laboratories, Wilmington, Mass.) were given intraperitoneal injections of ISIS 145746 or ISIS 351642 twice per week for two weeks with the doses shown in Table 20. Saline-injected animals served as controls. Each treatment group contained 4 mice. The mice were sacrificed 2 days following administration of the fourth and final dose of oligonucleotide or saline.

Mice were evaluated for SGLT2 levels in kidney. Target levels were determined by quantitative real-time PCR as described by other examples herein. PCR results were normalized to cyclophilin. The data are expressed as percent change relative to saline treated animals ("+" indicates an increase, "−" indicates a decrease) and are illustrated in Table 20.

TABLE 20

Antisense inhibition of SGLT2 mRNA expression in vivo by mixed backbone and full phosphorothioate oligonucleotides (expressed as percent change in SGLT2 mRNA expression relative to saline)

| Dose of oligonucleotide mg/kg | ISIS 145746 | ISIS 351642 |
|---|---|---|
| 1 | — | −26.7 |
| 5 | −5.8 | −35.1 |
| 25 | −10.5 | −44.3 |
| 50 | −35.6 | −31.8 |

These results illustrate that the compounds of the invention, both full phosphorothioate and mixed backbone oligonucleotides, can inhibit the expression of kidney SGLT2 in a dose-dependent manner. At doses of 5 and 25 mg/kg, greater inhibition is observed in kidneys from mice treated with ISIS 351462, suggesting the mixed backbone antisense compound is a more efficient inhibitor of target mRNA expression in the kidney.

Treated mice were further evaluated for body weight, liver weight and spleen weight. The data are expressed as percent change in body or organ weight ("+" indicates an increase, "−" indicates a decrease). The results are presented in Table 21.

TABLE 21

Effects of antisense compounds on total body weight, liver weight and spleen weight of mice

| | Percent change in weight | | | | | |
|---|---|---|---|---|---|---|
| | ISIS 145746 | | | ISIS 351642 | | |
| Dose of oligonucleotide mg/kg | Total Body | Liver | Spleen | Total Body | Liver | Spleen |
| 1 | — | — | — | +6.9 | −8.2 | +0.8 |
| 5 | +3.6 | −5.7 | +6.5 | +4.6 | −0.6 | −7.9 |
| 25 | +5.4 | −2.0 | +3.7 | +4.7 | −10.6 | +1.1 |
| 50 | +12.1 | −8.4 | +10.0 | +7.4 | −3.0 | +1.3 |

No significant change was observed in total body weight, liver weight or spleen weight at timepoints throughout or at the termination of the study.

Levels of BUN, creatinine, AST, ALT, albumin, triglycerides, cholesterol and glucose were measured in mice treated with the compounds of the invention. Plasma samples were analyzed using the Olympus AU400e automated chemistry analyzer (Olympus America, Irving, Tex.). The results, expressed as units measured, are shown for ISIS 145746 in Table 22 and ISIS 351642 in Table 23.

TABLE 22

Effect of the full phosphorothioate antisense compound ISIS 145746 on indicators of liver and kidney function

| | | | Units measured per dose of ISIS 145746 | | | |
|---|---|---|---|---|---|---|
| Serum indicator | Normal Range | Saline | 1 mg/kg | 5 mg/kg | 25 mg/kg | 50 mg/kg |
| Creatinine mg/L | 0.0-1.0 | 0.1 | — | 0.2 | 0.2 | 0.1 |
| AST IU/L | 30-300 | 129 | — | 60 | 84 | 155 |
| ALT IU/L | 30-200 | 30 | — | 28 | 26 | 77 |
| Albumin g/dL | 2.5-4.0 | 2.8 | — | 2.9 | 2.8 | 2.9 |
| Triglycerides mg/dL | 25-100* | 298 | — | 268 | 259 | 236 |
| Cholesterol mg/dL | 70-125 | 116 | — | 118 | 108 | 106 |
| Glucose mg/dL | 80-150* | 163 | — | 162 | 181 | 179 |

TABLE 23

Effect of mixed backbone antisense compound ISIS 351642 on indicators of liver and kidney function

| | | | Units measured per dose of ISIS 351642 | | | |
|---|---|---|---|---|---|---|
| Serum indicator | Normal Range | Saline | 1 mg/kg | 5 mg/kg | 25 mg/kg | 50 mg/kg |
| Creatinine mg/L | 0.0-1.0 | 0.1 | 0.1 | 0.1 | 0.2 | 0.2 |
| AST IU/L | 30-300 | 129 | 132 | 75 | 131 | 160 |
| ALT IU/L | 30-200 | 30 | 31 | 28 | 29 | 31 |
| Albumin g/dL | 2.5-4.0 | 2.8 | 2.9 | 3.0 | 2.7 | 2.8 |
| Triglycerides mg/dL | 25-100* | 298 | 238 | 287 | 240 | 233 |
| Cholesterol mg/dL | 70-125 | 116 | 117 | 122 | 106 | 113 |
| Glucose mg/dL | 80-150* | 163 | 195 | 175 | 164 | 171 |

*Triglyceride and glucose levels are routinely higher in the Balb/c strain of mice than in other strains of mice.

The levels of routine clinical indicators of liver and kidney injury and disease are within normal ranges and are not significantly changed relative to saline-treated animals, demonstrating that the compounds of the invention do not significantly affect renal or hepatic function. Triglyceride and glucose levels, while outside the normal range as is common in the Balb/c strain, are not significantly elevated relative to saline-treated animals.

The results illustrated in this example demonstrate that antisense compounds of different chemistries are delivered to the kidney, reduce SGLT2 expression in vivo in a dose-dependent manner, and that treatment with these compounds does not result in liver or kidney toxicity. The results further suggest that mixed backbone compound ISIS 351642 is more effective than full phosphorothioate oligonucleotides at reducing target mRNA levels in the kidney, particularly at low doses.

Example 19

Comparison of a Standard Mixed Backbone Compound and a Mixed Backbone Compound with Phosphorothioate Linkages at the Extreme 5' and 3' Ends: a Single Dose Study In accordance with the present invention, ISIS 257016 and ISIS 351641 were analyzed for their ability to inhibit SGLT2 expression in vivo. ISIS 257016 is a standard mixed backbone compound having 2'-MOE wings and a deoxy gap, with phosphodiester linkages in the wings and phosphorothioate linkages in the gap. ISIS 351641 differs from the standard mixed backbone compounds by having one phosphorothioate linkage at each of the extreme 5' and 3' ends of the wings.

Male 8-week old Balb/c mice (Charles River Laboratories, Wilmington, Mass.) were given a single intraperitoneal injection of ISIS 257016 or ISIS 351641 at a dose of 1, 5, 25, or 50 mg/kg. Saline-injected animals served as controls. Each treatment group contained 4 mice. The mice were sacrificed 2 days following administration of the single dose of oligonucleotide or saline.

Mice were evaluated for SGLT2 levels in kidney. Target levels were determined by quantitative real-time PCR as described by other examples herein. PCR results were normalized to cyclophilin. The data are expressed as percent change relative to saline treated animals ("+" indicates an increase, "−" indicates a decrease) and are illustrated in Table 24.

TABLE 24

Antisense inhibition of SGLT2 mRNA expression in vivo by mixed backbone oligonucleotides (expressed as percent change in SGLT2 mRNA expression relative to saline)

| Dose of oligonucleotide mg/kg | ISIS 257016 | ISIS 351641 |
|---|---|---|
| 1 | −21.5 | −14.0 |
| 5 | −26.4 | −19.3 |
| 25 | −24.2 | −12.5 |
| 50 | −36.3 | −22.0 |

These results illustrate that mixed backbone compounds of the invention, with either complete phosphodiester linkages in the wings, or with the extreme 5' and 3' ends substituted with phosphorothioate linkages, inhibit the expression of kidney SGLT2 in a dose-dependent manner. However, greater inhibition is observed in kidneys from mice treated with ISIS 257016, which contains all phosphodiester linkages in the wings.

Treated mice were further evaluated for body weight and liver and spleen weight. The data are expressed as percent change in body or organ weight ("+" indicates an increase, "−" indicates a decrease). The results are presented in Table 25.

TABLE 25

Effects of antisense compounds on total body weight, liver weight and spleen weight of mice

| Dose of oligonucleotide mg/kg | ISIS 257016 Total Body | Liver | Spleen | ISIS 351641 Total Body | Liver | Spleen |
|---|---|---|---|---|---|---|
| 1 | −0.9 | +1.2 | −1.6 | +2.8 | +3.0 | −0.1 |
| 5 | −5.1 | +5.4 | +20.1 | +4.0 | +2.1 | +9.7 |
| 25 | −1.1 | +3.5 | +3.8 | −0.7 | +9.3 | +5.9 |
| 50 | −2.5 | −2.3 | +7.8 | +0.9 | −0.7 | +10.2 |

No significant change was observed in total body weight, liver weight or spleen weight at timepoints throughout or at the termination of the study.

Levels of creatinine, AST, ALT, albumin, triglycerides, cholesterol and glucose were measured in mice treated with the compounds of the invention. Plasma samples were analyzed using the Olympus AU400e automated chemistry analyzer (Olympus America, Irving, Tex.). The results, expressed as units measured, are shown for ISIS 257016 in Table 26 and for ISIS 351641 in Table 27.

TABLE 26

Effect of mixed backbone antisense compound ISIS 257016 on indicators of liver and kidney function

| Serum indicator | Normal Range | Saline | 1 mg/kg | 5 mg/kg | 25 mg/kg | 50 mg/kg |
|---|---|---|---|---|---|---|
| Creatinine mg/L | 0.0-1.0 | 0.0 | 0.0 | 0.0 | 0.0 | 0.2 |
| AST IU/L | 30-300 | 141 | 62 | 77 | 89 | 88 |
| ALT IU/L | 30-200 | 30 | 29 | 28 | 27 | 33 |
| Albumin g/dL | 2.5-4.0 | 2.9 | 2.8 | 2.8 | 3.0 | 2.9 |
| Triglycerides mg/dL | 25-100* | 213 | 253 | 255 | 347 | 245 |
| Cholesterol mg/dL | 70-125 | 118 | 111 | 116 | 125 | 120 |
| Glucose mg/dL | 80-150* | 155 | 186 | 172 | 174 | 169 |

TABLE 27

Effect of mixed backbone antisense compound ISIS 351641 on indicators of liver and kidney function

| Serum indicator | Normal Range | Saline | 1 mg/kg | 5 mg/kg | 25 mg/kg | 50 mg/kg |
|---|---|---|---|---|---|---|
| Creatinine mg/L | 0.0-1.0 | 0.0 | 0.2 | 0.1 | 0.1 | 0.2 |
| AST IU/L | 30-300 | 141 | 75 | 117 | 68 | 98 |
| ALT IU/L | 30-200 | 30 | 25 | 33 | 30 | 27 |
| Albumin g/dL | 2.5-4.0 | 2.9 | 2.9 | 2.9 | 2.9 | 2.9 |
| Triglycerides mg/dL | 25-100* | 213 | 271 | 280 | 296 | 271 |

TABLE 27-continued

Effect of mixed backbone antisense compound ISIS 351641 on indicators of liver and kidney function

| Serum indicator | Normal Range | Saline | Units measured per dose of ISIS 351641 | | | |
|---|---|---|---|---|---|---|
| | | | 1 mg/kg | 5 mg/kg | 25 mg/kg | 50 mg/kg |
| Cholesterol mg/dL | 70-125 | 118 | 120 | 126 | 112 | 117 |
| Glucose mg/dL | 80-150* | 155 | 162 | 171 | 189 | 175 |

*Triglyceride and glucose levels are routinely higher in the Balb/c strain of mice than in other strains of mice.

The levels of routine clinical indicators of liver and kidney injury and disease are within normal ranges and are not significantly changed relative to saline-treated animals, demonstrating that the compounds of the invention do not significantly affect renal or hepatic function. Triglyceride and glucose levels, while outside the normal range as is common in the Balb/c strain, are not significantly elevated relative to saline-treated animals.

The results illustrated in this example demonstrate that mixed backbone compounds of varying chemistries are delivered to the kidney, reduce SGLT2 expression in vivo, and that treatment with these compounds does not result in liver or kidney toxicity. The results further indicate that mixed backbone compounds with wings composed completely of phosphodiester linkages are more efficient inhibitors of target mRNA.

Example 20

Effects of Modified Antisense Compounds on SGLT2 mRNA Expression In Vivo: Two and Three Dose Protocols In accordance with the present invention, mixed backbone compound ISIS 257016 was analyzed for its ability to inhibit SGLT2 expression in vivo when administered in either two or three doses. ISIS 353003 (CCTTCCCTGAAGGTTCCTCC; SEQ ID NO: 17), a mixed backbone oligonucleotide which targets human PTP1B, was used as a control.

Male 8-week old Balb/c mice (Charles River Laboratories, Wilmington, Mass.) were given two or three intraperitoneal injections of ISIS 257016 or ISIS 353003 at three day intervals. ISIS 257016 was administered at doses of 1, 5 or 25 mg/kg and ISIS 353003 was administered at a dose of 25 mg/kg. Saline-injected animals served as controls. Each treatment group contained 4 mice. The mice were sacrificed 2 days following administration of the final dose of oligonucleotide or saline.

Mice were evaluated for SGLT2 levels in kidney. Target levels were determined by quantitative real-time PCR as described in other examples herein. PCR results were normalized to cyclophilin. The data are expressed as percent change relative to saline treated animals ("+" indicates an increase, "−" indicates a decrease) and are illustrated in Table 28.

TABLE 28

Antisense inhibition of SGLT2 mRNA expression in vivo by two doses or three doses of mixed backbone oligonucleotides (expressed as percent change in SGLT2 mRNA expression relative to saline control)

| Oligonucleotide (dose in mg/kg) | Two Doses | Three Doses |
|---|---|---|
| ISIS 257016 (1 mg/kg) | −43.2 | −39.1 |
| ISIS 257016 (5 mg/kg) | −39.7 | −42.9 |
| ISIS 257016 (25 mg/kg) | −53.8 | −65.5 |
| ISIS 353003 (25 mg/kg) | −8.0 | −6.9 |

These results illustrate that the mixed backbone compounds of the invention efficiently inhibit the expression of kidney SGLT2 in a dose-dependent manner. Furthermore, inhibition increases with the number of doses administered.

Treated mice were further evaluated for body weight, kidney weight, liver weight and spleen weight. The data are expressed as percent change in body or organ weight ("+" indicates an increase, "−" indicates a decrease). The results are presented in Table 29 and Table 30.

TABLE 29

Effects of antisense compounds on total body weight of mice (expressed as percent change in body weight)

| Oligonucleotide (dose in mg/kg) | Two Doses | Three Doses |
|---|---|---|
| ISIS 257016 (1 mg/kg) | −1.1 | 0 |
| ISIS 257016 (5 mg/kg) | +1.3 | +0.8 |
| ISIS 257016 (25 mg/kg) | +0.1 | +1.3 |
| ISIS 353003 (25 mg/kg) | −0.8 | +0.8 |

TABLE 30

Effects of antisense compounds on total kidney weight, liver weight and spleen weight of mice

| Oligonucleotide (dose in mg/kg) | Percent change in weight | | | | | |
|---|---|---|---|---|---|---|
| | Two Doses | | | Three Doses | | |
| | Kidney | Liver | Spleen | Kidney | Liver | Spleen |
| ISIS 257016 (1 mg/kg) | −0.5 | −2.2 | −4.3 | −5.6 | −3.8 | −5.9 |
| ISIS 257016 (5 mg/kg) | −5.4 | +2.5 | +7.4 | −6.6 | −7.1 | −9.0 |
| ISIS 257016 (25 mg/kg) | −7.9 | −1.1 | +4.2 | −8.6 | −8.8 | −1.2 |
| ISIS 353003 (25 mg/kg) | −5.5 | +1.2 | −2.7 | −0.2 | −4.0 | +6.5 |

No significant change was observed in total body weight, kidney weight, liver weight or spleen weight at timepoints throughout or at the termination of the study.

Levels of BUN, creatinine, bilirubin, AST, ALT, albumin, triglycerides, cholesterol and glucose were measured in mice treated with the compounds of the invention. Plasma samples were analyzed using the Olympus AU400e automated chemistry analyzer (Olympus America, Irving, Tex.). The results, expressed as units measured, are shown for the two dose protocol in Table 31 and for the three dose protocol in Table 32.

TABLE 31

Effect of mixed backbone antisense compound ISIS 257016 administered according to the two dose protocol on indicators of liver and kidney function

| Serum indicator | Normal Range | Saline | Units measured per dose of ISIS 257016 | | | ISIS 353003 |
|---|---|---|---|---|---|---|
| | | | 1 mg/kg | 5 mg/kg | 25 mg/kg | |
| BUN mg/dL | 15-40 | 32 | 34 | 29 | 25 | 28 |
| Creatinine mg/L | 0.0-1.0 | 0.1 | 0.1 | 0.2 | 0.1 | 0.1 |
| Bilirubin mg/dL | 0.1-1.0 | 0.1 | 0.1 | 0.1 | 0.1 | 0.1 |
| AST IU/L | 30-300 | 54 | 119 | 156 | 116 | 154 |
| ALT IU/L | 30-200 | 27 | 36 | 45 | 30 | 36 |
| Albumin g/dL | 2.5-4.0 | 2.7 | 3.2 | 3.1 | 3.0 | 2.8 |
| Triglycerides mg/dL | 25-100* | 221 | 263 | 234 | 264 | 278 |
| Cholesterol mg/dL | 70-125 | 113 | 118 | 117 | 125 | 125 |
| Glucose mg/dL | 80-150* | 170 | 157 | 177 | 163 | 152 |

TABLE 32

Effect of mixed backbone antisense compound ISIS 257016 administered according to the three dose protocol on indicators of liver and kidney function

| Serum indicator | Normal Range | Saline | Units measured per dose of ISIS 257016 | | | ISIS 353003 |
|---|---|---|---|---|---|---|
| | | | 1 mg/kg | 5 mg/kg | 25 mg/kg | |
| BUN mg/dL | 15-40 | 30 | 32 | 30 | 27 | 27 |
| Creatinine mg/L | 0.0-1.0 | 0.1 | 0.1 | 0.2 | 0.1 | 0.1 |
| Bilirubin mg/dL | 0.1-1.0 | 0.1 | 0.1 | 0.1 | 0.1 | 0.1 |
| AST IU/L | 30-300 | 126 | 83 | 81 | 59 | 57 |
| ALT IU/L | 30-200 | 35 | 30 | 57 | 27 | 24 |
| Albumin g/dL | 2.5-4.0 | 3.0 | 2.8 | 2.8 | 2.7 | 2.8 |
| Triglycerides mg/dL | 25-100* | 223 | 236 | 202 | 153 | 188 |
| Cholesterol mg/dL | 70-125 | 112 | 113 | 114 | 116 | 106 |
| Glucose mg/dL | 80-150* | 152 | 169 | 161 | 181 | 192 |

*Triglyceride and glucose levels are routinely higher in the Balb/c strain of mice than in other strains of mice.

The levels of routine clinical indicators of liver and kidney injury and disease are within normal ranges and are not significantly changed relative to saline-treated animals, demonstrating that the compounds of the invention do not significantly affect renal or hepatic function. Triglyceride and glucose levels, while outside the normal range as is common in the Balb/c strain, are not significantly elevated relative to saline-treated animals.

Mice injected with ISIS 257016 and control animals were also evaluated histologically following routine procedures. Liver and kidney samples were procured, fixed in 10% neutral-buffered formalin and processed for staining with hematoxylin and eosin. Hematoxylin and eosin staining exhibited no significant difference between saline- and oligonucleotide-treated animals. All tissue samples exhibited normal kidney and liver morphology.

The results illustrated in this example demonstrate that mixed backbone compounds are delivered to the kidney, reduce SGLT2 expression in vivo, and that treatment with these compounds does not result in liver or kidney toxicity. The results further indicate that inhibition of target mRNA expression in the kidney increases with the number of doses administered.

Example 21

Effects of Mixed Backbone Antisense Compounds on SGLT2 mRNA Expression In Vivo: Two to Five Day Consecutive Daily Dosing Protocols In accordance with the present invention, mixed backbone compound ISIS 257016 (SEQ ID NO: 4) was analyzed for its ability to inhibit SGLT2 expression in vivo when administered in two to five doses (consecutive daily doses). ISIS 353003 (SEQ ID NO: 17), a mixed backbone oligonucleotide which targets human PTP1B, was used as a control.

Male 9-week old Balb/c mice (Charles River Laboratories, Wilmington, Mass.) were given two, three, four or five intraperitoneal injections of ISIS 257016 or ISIS 353003 once a day for the treatment period. ISIS 257016 was administered at doses of 2.5 or 25 mg/kg and ISIS 353003 was administered at a dose of 25 mg/kg. Saline-injected animals served as controls. Each treatment group contained 4 mice. The mice were sacrificed 2 days following administration of the final dose of oligonucleotide or saline.

Mice were evaluated for SGLT2 levels in kidney. Target levels were determined by quantitative real-time PCR as described in other examples herein. PCR results were normalized to cyclophilin. The data are expressed as percent change relative to saline treated animals ("+" indicates an increase, "−" indicates a decrease) and are illustrated in Table 33.

TABLE 33

Antisense inhibition of SGLT2 mRNA expression in vivo by mixed backbone oligonucleotide (expressed as percent change in SGLT2 mRNA expression relative to saline control)

| Oligonucleotide (dose in mg/kg) | Two Doses | Three Doses | Four Doses | Five Doses |
|---|---|---|---|---|
| ISIS 257016 (2.5 mg/kg) | −14.2 | −35.4 | −25.3 | −42.0 |
| ISIS 257016 (25 mg/kg) | −12.5 | −32.9 | −39.1 | −68.9 |
| ISIS 353003 (25 mg/kg) | −4.5 | −9.6 | +0.5 | −11.3 |

These results illustrate that the mixed backbone compounds of the invention efficiently inhibit the expression of kidney SGLT2 and inhibition increases with the number of doses administered.

Treated mice were further evaluated for body weight, kidney weight, liver weight and spleen weight. The data are expressed as percent change in body or organ weight ("+" indicates an increase, "−" indicates a decrease). The results are presented in Tables 34-37.

TABLE 34

Effects of antisense compounds on total body weight of mice (expressed as percent change in body weight)

| Oligonucleotide (dose in mg/kg) | Two Doses | Three Doses | Four Doses | Five Doses |
|---|---|---|---|---|
| ISIS 257016 (2.5 mg/kg) | +2.7 | +2.7 | +3.2 | +1.5 |
| ISIS 257016 (25 mg/kg) | +2.0 | +2.0 | +3.1 | −0.7 |
| ISIS 353003 (25 mg/kg) | +0.6 | +0.8 | +2.5 | +1.3 |

TABLE 35

Effects of antisense compounds on total kidney weight (expressed as percent change in kidney weight)

| Oligonucleotide (dose in mg/kg) | Two Doses | Three Doses | Four Doses | Five Doses |
|---|---|---|---|---|
| ISIS 257016 (2.5 mg/kg) | +8.2 | −1.4 | +8.9 | +1.5 |
| ISIS 257016 (25 mg/kg) | +11.5 | +3.6 | +2.7 | −7.7 |
| ISIS 353003 (25 mg/kg) | +5.3 | −3.6 | +4.9 | +7.1 |

TABLE 36

Effects of antisense compounds on total liver weight (expressed as percent change in liver weight)

| Oligonucleotide (dose in mg/kg) | Two Doses | Three Doses | Four Doses | Five Doses |
|---|---|---|---|---|
| ISIS 257016 (2.5 mg/kg) | +9.2 | +7.5 | +4.8 | +4.8 |
| ISIS 257016 (25 mg/kg) | +11.8 | +5.2 | +0.6 | −8.0 |
| ISIS 353003 (25 mg/kg) | +7.4 | −3.4 | +12.9 | +9.5 |

TABLE 37

Effects of antisense compounds on total spleen weight (expressed as percent change in spleen weight)

| Oligonucleotide (dose in mg/kg) | Two Doses | Three Doses | Four Doses | Five Doses |
|---|---|---|---|---|
| ISIS 257016 (2.5 mg/kg) | +22.2 | +10.1 | +15.3 | +10.7 |
| ISIS 257016 (25 mg/kg) | +13.3 | +5.1 | +6.7 | +4.5 |
| ISIS 353003 (25 mg/kg) | +7.3 | +1.4 | +19.8 | +8.6 |

No significant change was observed in total body weight, kidney weight, liver weight or spleen weight at timepoints throughout or at the termination of the study.

Levels of creatinine, AST, ALT, albumin, triglycerides, cholesterol and glucose were measured in mice treated with the compounds of the invention. Plasma samples were analyzed using the Olympus AU400e automated chemistry analyzer (Olympus America, Irving, Tex.). The results, expressed as units measured, are shown in Tables 38-41.

TABLE 38

Effect of mixed backbone antisense compound ISIS 257016 administered as two consecutive daily doses on indicators of liver and kidney function

| Serum indicator | Normal Range | Saline | ISIS 257016 2.5 mg/kg | ISIS 257016 25 mg/kg | ISIS 353003 25 mg/kg |
|---|---|---|---|---|---|
| Creatinine mg/L | 0.0-1.0 | 0.2 | 0.1 | 0.1 | 0.2 |
| AST IU/L | 30-300 | 160 | 132 | 75 | 131 |
| ALT IU/L | 30-200 | 31 | 31 | 28 | 29 |
| Albumin g/dL | 2.5-4.0 | 2.8 | 2.9 | 3.0 | 2.7 |
| Triglycerides mg/dL | 25-100* | 233 | 238 | 287 | 240 |
| Cholesterol mg/dL | 70-125 | 113 | 117 | 122 | 106 |
| Glucose mg/dL | 80-150* | 171 | 195 | 175 | 164 |

TABLE 39

Effect of mixed backbone antisense compound ISIS 257016 administered as three consecutive daily doses on indicators of liver and kidney function

| Serum indicator | Normal Range | Saline | ISIS 257016 2.5 mg/kg | ISIS 257016 25 mg/kg | ISIS 353003 25 mg/kg |
|---|---|---|---|---|---|
| Creatinine mg/L | 0.0-1.0 | 0.1 | 0.2 | 0.2 | 0.1 |

TABLE 39-continued

Effect of mixed backbone antisense compound ISIS 257016 administered as three consecutive daily doses on indicators of liver and kidney function

| Serum indicator | Normal Range | Saline | Units measured per dose of oligonucleotide | | |
|---|---|---|---|---|---|
| | | | ISIS 257016 2.5 mg/kg | ISIS 257016 25 mg/kg | ISIS 353003 25 mg/kg |
| AST IU/L | 30-300 | 199 | 60 | 84 | 155 |
| ALT IU/L | 30-200 | 29 | 28 | 26 | 77 |
| Albumin g/dL | 2.5-4.0 | 2.8 | 2.9 | 2.8 | 2.9 |
| Triglycerides mg/dL | 25-100* | 289 | 268 | 259 | 236 |
| Cholesterol mg/dL | 70-125 | 111 | 118 | 108 | 106 |
| Glucose mg/dL | 80-150* | 204 | 162 | 181 | 179 |

TABLE 40

Effect of mixed backbone antisense compound ISIS 257016 administered as four consecutive daily doses on indicators of liver and kidney function

| Serum indicator | Normal Range | Saline | Units measured per dose of oligonucleotide | | |
|---|---|---|---|---|---|
| | | | ISIS 257016 2.5 mg/kg | ISIS 257016 25 mg/kg | ISIS 353003 25 mg/kg |
| Creatinine mg/L | 0.0-1.0 | 0.1 | 0.1 | 0.1 | 0.2 |
| AST IU/L | 30-300 | 199 | 92 | 120 | 144 |
| ALT IU/L | 30-200 | 29 | 30 | 30 | 36 |
| Albumin g/dL | 2.5-4.0 | 2.8 | 3.0 | 2.8 | 3.0 |
| Triglycerides mg/dL | 25-100* | 289 | 252 | 269 | 294 |
| Cholesterol mg/dL | 70-125 | 111 | 126 | 115 | 120 |
| Glucose mg/dL | 80-150* | 204 | 173 | 198 | 192 |

TABLE 41

Effect of mixed backbone antisense compound ISIS 257016 administered as five consecutive daily doses on indicators of liver and kidney function

| Serum indicator | Normal Range | Saline | Units measured per dose of oligonucleotide | | |
|---|---|---|---|---|---|
| | | | ISIS 257016 2.5 mg/kg | ISIS 257016 25 mg/kg | ISIS 353003 25 mg/kg |
| Creatinine mg/L | 0.0–1.0 | 0.1 | 0.1 | 0.1 | 0.1 |
| AST IU/L | 30–300 | 129 | 121 | 125 | 97 |
| ALT IU/L | 30–200 | 30 | 30 | 33 | 29 |
| Albumin g/dL | 2.5-4.0 | 2.8 | 2.9 | 2.8 | 2.9 |
| Triglycerides mg/dL | 25–100* | 298 | 298 | 285 | 277 |
| Cholesterol mg/dL | 70–125 | 116 | 126 | 122 | 126 |

TABLE 41-continued

Effect of mixed backbone antisense compound ISIS 257016 administered as five consecutive daily doses on indicators of liver and kidney function

| Serum indicator | Normal Range | Saline | ISIS 257016 2.5 mg/kg | ISIS 257016 25 mg/kg | ISIS 353003 25 mg/kg |
|---|---|---|---|---|---|
| | | | Units measured per dose of oligonucleotide | | |
| Glucose mg/dL | 80–150* | 163 | 177 | 204 | 185 |

*Triglyceride and glucose levels are routinely higher in the Balb/c strain of mice than in other strains of mice.

The levels of routine clinical indicators of liver and kidney injury and disease are within normal ranges and are not significantly changed relative to saline-treated animals, demonstrating that the compounds of the invention do not significantly affect renal or hepatic function. Triglyceride and glucose levels, while outside the normal range as is common in the Balb/c strain, are not significantly elevated relative to saline-treated animals.

The results illustrated in this example demonstrate that mixed backbone compounds are delivered to the kidney, reduce SGLT2 expression in vivo, and that treatment with these compounds does not result in liver or kidney toxicity. The results further indicate that inhibition of target mRNA expression in the kidney increases with the number of doses administered.

Example 22

Comparison of a Standard Mixed Backbone Compound and Mixed Backbone Compounds with Phosphorothioate Linkages at Either or Both of the Extreme 5' and 3' Ends: a Four Dose Protocol In accordance with the present invention, ISIS 257016 (SEQ ID NO: 4), ISIS 351641 (SEQ ID NO: 4), ISIS 360886 (SEQ ID NO: 4) and ISIS 360887 (SEQ ID NO: 4) were analyzed for their ability to inhibit SGLT2 expression in vivo. ISIS 257016 is a standard mixed backbone compound having 2'-MOE wings and a deoxy gap, with phosphodiester linkages in the wings and phosphorothioate linkages in the gap. ISIS 351641 differs from the standard mixed backbone compounds by having one phosphorothioate linkage at each of the extreme 5' and 3' ends of the wings. ISIS 360886 and ISIS 360887 are mixed backbone compounds with one phosphorothioate linkage at the extreme 5' end or extreme 3' end, respectively.

Male 7-week old Balb/c mice (Charles River Laboratories, Wilmington, Mass.) were given intraperitoneal injections of ISIS 257016, ISIS 351641, ISIS 360886 or ISIS 360887 twice a week for two weeks at doses of 1.56, 6.25 or 25 mg/kg. Saline-injected animals served as controls. Each treatment group contained 4 mice. The mice were sacrificed 2 days following administration of the final dose of oligonucleotide or saline.

Mice were evaluated for SGLT2 levels in kidney. Target levels were determined by quantitative real-time PCR as described in other examples herein. PCR results were normalized to cyclophilin. The data are expressed as percent change relative to saline treated animals ("+" indicates an increase, "–" indicates a decrease) and are illustrated in Table 42.

TABLE 42

Antisense inhibition of SGLT2 mRNA expression in vivo by mixed backbone oligonucleotides (expressed as percent change in SGLT2 mRNA expression relative to saline)

| Dose of oligonucleotide mg/kg | ISIS 257016 | ISIS 351641 | ISIS 360886 | ISIS 360887 |
|---|---|---|---|---|
| 1.56 | –39.1 | –4.2 | –12.7 | –9.7 |
| 6.25 | –52.8 | –4.87 | –19.7 | –7.3 |
| 25 | –57.8 | –11.0 | –29.0 | –4.9 |

These results illustrate that mixed backbone compounds of the invention, with either complete phosphodiester linkages in the wings, or with the extreme 5' and 3' ends substituted with phosphorothioate linkages, can inhibit the expression of kidney SGLT2 in a dose-dependent manner. With the exception of ISIS 360887, inhibition of target mRNA was dose-dependent. Although all mixed backbone compounds inhibited SGLT2 expression, greater inhibition is observed in kidneys from mice treated with ISIS 257016, which is a mixed backbone compound that contains all phosphodiester linkages in the wings.

Treated mice were further evaluated for body weight, kidney weight, liver weight and spleen weight. The data are expressed as percent change in body or organ weight ("+" indicates an increase, "–" indicates a decrease). The results are presented in Table 43.

TABLE 43

Effects of antisense compounds on total body weight, kidney weight, liver weight and spleen weight of mice (expressed as percent change in weight)

| Oligonucleotide | Dose mg/kg | Body weight | Kidney weight | Liver weight | Spleen weight |
|---|---|---|---|---|---|
| ISIS 257016 | 1.56 | +11.6 | –3.5 | –4.2 | –2.4 |
| ISIS 257016 | 6.25 | +7.9 | –3.0 | +3.8 | –1.3 |
| ISIS 257016 | 25 | +11.7 | –4.1 | +1.4 | +8.9 |
| ISIS 351641 | 1.56 | +7.9 | –0.9 | –5.4 | +9.4 |
| ISIS 351641 | 6.25 | +11.1 | +1.3 | –2.2 | +13.4 |
| ISIS 351641 | 25 | +7.4 | –2.1 | –0.5 | –1.4 |
| ISIS 360886 | 1.56 | +7.6 | –1.0 | –13.7 | –5.0 |
| ISIS 360886 | 6.25 | +8.9 | –3.7 | –16.6 | +1.2 |
| ISIS 360886 | 25 | +11.1 | –5.5 | –11.6 | +0.8 |
| ISIS 360887 | 1.56 | +8.5 | +1.0 | –10.4 | –0.4 |
| ISIS 360887 | 6.25 | +7.5 | –1.8 | –8.4 | +1.1 |
| ISIS 360887 | 25 | +9.8 | +2.2 | –9.0 | +11.8 |

No significant change was observed in total body weight, liver weight or spleen weight at timepoints throughout or at the termination of the study.

Levels of BUN, creatinine, bilirubin, AST, ALT, albumin, triglycerides, cholesterol and glucose were measured in mice treated with the compounds of the invention. Plasma samples were analyzed using the Olympus AU400e automated chemistry analyzer (Olympus America, Irving, Tex.). The results, expressed as units measured, are shown in Tables 44-47.

TABLE 44

Effect of mixed backbone antisense compound ISIS 257016 on indicators of liver and kidney function

| Serum indicator | Normal Range | Units measured per dose of ISIS 257016 | | |
|---|---|---|---|---|
| | | Saline | 1.56 mg/kg | 6.25 mg/kg | 25 mg/kg |
| BUN mg/dL | 15-40 | 23 | 21 | 26 | 22 |
| Creatinine mg/L | 0.0-1.0 | 0.2 | 0.2 | 0.2 | 0.2 |
| Bilirubin mg/dL | 0.1-1.0 | 0.2 | 0.2 | 0.2 | 0.1 |
| AST IU/L | 30-300 | 75 | 61 | 83 | 71 |
| ALT IU/L | 30-200 | 30 | 30 | 33 | 39 |
| Albumin g/dL | 2.5-4.0 | 2.8 | 2.9 | 2.9 | 2.7 |
| Triglycerides mg/dL | 25-100* | 208 | 210 | 243 | 150 |
| Cholesterol mg/dL | 70-125 | 116 | 125 | 130 | 135 |
| Glucose mg/dL | 80-150* | 207 | 184 | 184 | 215 |

TABLE 45

Effect of mixed backbone antisense compound ISIS 351641 on indicators of liver and kidney function

| Serum indicator | Normal Range | Units measured per dose of ISIS 351641 | | |
|---|---|---|---|---|
| | | Saline | 1.56 mg/kg | 6.25 mg/kg | 25 mg/kg |
| BUN mg/dL | 15-40 | 23 | 23 | 25 | 22 |
| Creatinine mg/L | 0.0-1.0 | 0.2 | 0.2 | 0.2 | 0.2 |
| Bilirubin mg/dL | 0.1-1.0 | 0.2 | 0.1 | 0.2 | 0.1 |
| AST IU/L | 30-300 | 75 | 61 | 67 | 54 |
| ALT IU/L | 30-200 | 30 | 32 | 31 | 30 |
| Albumin g/dL | 2.5-4.0 | 2.8 | 2.7 | 2.7 | 2.8 |
| Triglycerides mg/dL | 25-100* | 208 | 169 | 176 | 185 |
| Cholesterol mg/dL | 70-125 | 116 | 110 | 115 | 107 |
| Glucose mg/dL | 80-150* | 207 | 205 | 199 | 208 |

TABLE 46

Effect of mixed backbone antisense compound ISIS 360886 on indicators of liver and kidney function

| Serum indicator | Normal Range | Units measured per dose of ISIS 360886 | | |
|---|---|---|---|---|
| | | Saline | 1.56 mg/kg | 6.25 mg/kg | 25 mg/kg |
| BUN mg/dL | 15-40 | 23 | 21 | 23 | 24 |
| Creatinine mg/L | 0.0-1.0 | 0.2 | 0.1 | 0.2 | 0.2 |
| Bilirubin mg/dL | 0.1-1.0 | 0.2 | 0.2 | 0.2 | 0.1 |
| AST IU/L | 30-300 | 75 | 56 | 77 | 73 |
| ALT IU/L | 30-200 | 30 | 26 | 27 | 28 |
| Albumin g/dL | 2.5-4.0 | 2.8 | 2.7 | 2.7 | 2.7 |
| Triglycerides mg/dL | 25-100* | 208 | 164 | 181 | 169 |
| Cholesterol mg/dL | 70-125 | 116 | 105 | 108 | 108 |
| Glucose mg/dL | 80-150* | 207 | 189 | 202 | 200 |

TABLE 47

Effect of mixed backbone antisense compound ISIS 360887 on indicators of liver and kidney function

| Serum indicator | Normal Range | Units measured per dose of ISIS 360887 | | |
|---|---|---|---|---|
| | | Saline | 1.56 mg/kg | 6.25 mg/kg | 25 mg/kg |
| BUN mg/dL | 15-40 | 23 | 23 | 22 | 23 |
| Creatinine mg/L | 0.0-1.0 | 0.2 | 0.2 | 0.2 | 0.2 |
| Bilirubin mg/dL | 0.1-1.0 | 0.2 | 0.2 | 0.1 | 0.2 |
| AST IU/L | 30-300 | 75 | 142 | 83 | 108 |
| ALT IU/L | 30-200 | 30 | 40 | 39 | 34 |
| Albumin g/dL | 2.5-4.0 | 2.8 | 2.7 | 2.7 | 2.7 |
| Triglycerides mg/dL | 25-100* | 208 | 136 | 157 | 200 |
| Cholesterol mg/dL | 70-125 | 116 | 109 | 107 | 110 |
| Glucose mg/dL | 80-150* | 207 | 199 | 201 | 187 |

*Triglyceride and glucose levels are routinely higher in the Balb/c strain of mice than in other strains of mice.

Cholesterol levels of mice treated with either 6.25 or 25 mg/kg were slightly elevated; however, these levels are not significantly greater than the cholesterol levels observed in saline-treated control animals. Otherwise, the levels of routine clinical indicators of liver and kidney injury and disease are within normal ranges and are not significantly changed relative to saline-treated animals, demonstrating that the compounds of the invention do not significantly affect renal or hepatic function. Triglyceride and glucose levels, while outside the normal range as is common in the Balb/c strain, are not significantly elevated relative to saline-treated animals.

Saline- and oligonucleotide-injected animals also were evaluated histologically following routine procedures. Liver and kidney samples were procured, fixed in 10% neutral-buffered formalin and processed for staining with hematoxylin and eosin. Hematoxylin and eosin staining exhibited no significant difference between control and oligonucleotide-treated animals.

The results illustrated in this example demonstrate that mixed backbone compounds are delivered to the kidney, reduce SGLT2 expression in vivo, and that treatment with these compounds does not result in liver or kidney toxicity. The results further indicate that mixed backbone compounds with complete phosphodiester linkages in the wings are more effective modulators of target mRNA expression in the kidney than mixed backbone compounds with a phosphorothioate linkage at one or both of the extreme 5' and 3' ends.

Example 23

Comparison of a Standard Mixed Backbone Compound and Mixed Backbone Compounds with Phosphorothioate Linkages at Either or Both of the Extreme 5' and 3' Ends: an Eight Dose Protocol A second study of SGLT2 antisense oligonucleotides ISIS 257016, ISIS 351641, ISIS 360886 and ISIS 360887 was undertaken in which mice received eight doses over a four week period. As described previously, ISIS 257016 is a standard mixed backbone compound having 2'-MOE wings and a deoxy gap, with phosphodiester linkages in the wings and phosphorothioate linkages in the gap. ISIS 351641 differs from the standard mixed backbone compounds by having one phosphorothioate linkage at each of the extreme 5' and 3' ends of the wings. ISIS 360886 and ISIS 360887 are mixed backbone compounds with one phosphorothioate linkage at the extreme 5' end and extreme 3' end, respectively.

Male 8-week old Balb/c mice (Charles River Laboratories, Wilmington, Mass.) were given intraperitoneal injections of ISIS 257016, ISIS 351641, ISIS 360886 or ISIS 360887 twice a week for four weeks at doses of 1, 5 or 25 mg/kg. Saline-injected animals served as controls. Each treatment group contained 4 mice. The mice were sacrificed 2 days following administration of the final dose of oligonucleotide or saline.

Mice were evaluated for SGLT2 levels in kidney. Target levels were determined by quantitative real-time PCR as described by other examples herein. PCR results were normalized to cyclophilin. The data are expressed as percent change relative to saline treated animals ("+" indicates an increase, "−" indicates a decrease) and are illustrated in Table 48.

TABLE 48

Antisense inhibition of SGLT2 mRNA expression in vivo by mixed backbone oligonucleotides (expressed as percent change in SGLT2 mRNA expression relative to saline)

| Dose of oligonucleotide mg/kg | ISIS 257016 | ISIS 351641 | ISIS 360886 | ISIS 360887 |
|---|---|---|---|---|
| 1 | −53 | −14 | −24 | −23 |
| 5 | −64 | −23 | −30 | −26 |
| 25 | −68 | −37 | −50 | −40 |

These results illustrate that mixed backbone compounds of the invention, with either complete phosphodiester linkages in the wings, or with the extreme 5' and 3' ends substituted with phosphorothioate linkages, can inhibit the expression of kidney SGLT2 in a dose-dependent manner. However, greater inhibition is observed in kidneys from mice treated with ISIS 257016, which contains all phosphodiester linkages in the wings.

Treated mice were further evaluated for body weight and liver and spleen weight. The data are expressed as percent change in body or organ weight ("+" indicates an increase, "−" indicates a decrease). The results are presented in Table 49.

TABLE 49

Effects of antisense compounds on total body weight, liver weight and spleen weight of mice (expressed as percent change in weight)

| Oligonucleotide | Dose mg/kg | Body weight | Liver weight | Spleen weight |
|---|---|---|---|---|
| ISIS 257016 | 1 | +11.8 | −6.9 | −10.1 |
| ISIS 257016 | 5 | +8.4 | −4.3 | +4.4 |
| ISIS 257016 | 25 | +5.4 | −2.1 | +12.5 |
| ISIS 351641 | 1 | +12.3 | −2.8 | −2.9 |
| ISIS 351641 | 5 | +9.2 | −8.7 | −5.5 |
| ISIS 351641 | 25 | +9.4 | −0.8 | +3.3 |
| ISIS 360886 | 1 | +9.2 | −5.2 | −4.5 |
| ISIS 360886 | 5 | +10.3 | −2.7 | +15.1 |
| ISIS 360886 | 25 | +9.4 | −2.1 | −11.4 |
| ISIS 360887 | 1 | +10.0 | −7.0 | −1.5 |
| ISIS 360887 | 5 | +12.6 | −3.2 | +4.0 |
| ISIS 360887 | 25 | +11.8 | −7.6 | +14.7 |

No significant change was observed in total body weight, liver weight or spleen weight at timepoints throughout or at the termination of the study.

Levels of BUN, creatinine, bilirubin, AST, ALT, albumin, triglycerides, cholesterol and glucose were measured in mice treated with the compounds of the invention. Plasma samples were analyzed using the Olympus AU400e automated chemistry analyzer (Olympus America, Irving, Tex.). The results, expressed as units measured, are shown in Tables 50-53.

TABLE 50

Effect of mixed backbone antisense compound ISIS 257016 on indicators of liver and kidney function

| Serum indicator | Normal Range | Saline | 1 mg/kg | 5 mg/kg | 25 mg/kg |
|---|---|---|---|---|---|
| BUN mg/dL | 15-40 | 27 | 31 | 29 | 23 |
| Creatinine mg/L | 0.0-1.0 | 0.2 | 0.2 | 0.2 | 0.2 |
| Bilirubin mg/dL | 0.1-1.0 | 0.2 | 0.2 | 0.2 | 0.2 |
| AST IU/L | 30-300 | 60 | 58 | 82 | 119 |
| ALT IU/L | 30-200 | 22 | 27 | 35 | 66 |
| Albumin g/dL | 2.5-4.0 | 2.7 | 2.8 | 2.7 | 2.6 |
| Triglycerides mg/dL | 25-100* | 178 | 263 | 187 | 99 |
| Cholesterol mg/dL | 70-125 | 123 | 142 | 138 | 162 |
| Glucose mg/dL | 80-150* | 193 | 201 | 201 | 185 |

TABLE 51

Effect of mixed backbone antisense compound ISIS 351641 on indicators of liver and kidney function

| Serum indicator | Normal Range | Saline | Units measured per dose of ISIS 351641 | | |
|---|---|---|---|---|---|
| | | | 1 mg/kg | 5 mg/kg | 25 mg/kg |
| BUN mg/dL | 15-40 | 27 | 27 | 26 | 28 |
| Creatinine mg/L | 0.0-1.0 | 0.2 | 0.2 | 0.2 | 0.2 |
| Bilirubin mg/dL | 0.1-1.0 | 0.2 | 0.1 | 0 | 0.1 |
| AST IU/L | 30-300 | 60 | 48 | 49 | 50 |
| ALT IU/L | 30-200 | 22 | 23 | 23 | 20 |
| Albumin g/dL | 2.5-4.0 | 2.7 | 2.8 | 2.8 | 2.7 |
| Triglycerides mg/dL | 25-100* | 178 | 165 | 197 | 222 |
| Cholesterol mg/dL | 70-125 | 123 | 118 | 120 | 118 |
| Glucose mg/dL | 80-150* | 193 | 192 | 200 | 197 |

TABLE 52

Effect of mixed backbone antisense compound ISIS 360886 on indicators of liver and kidney function

| Serum indicator | Normal Range | Saline | Units measured per dose of ISIS 360886 | | |
|---|---|---|---|---|---|
| | | | 1 mg/kg | 5 mg/kg | 25 mg/kg |
| BUN mg/dL | 15-40 | 27 | 27 | 26 | 27 |
| Creatinine mg/L | 0.0-1.0 | 0.2 | 0.2 | 0.2 | 0.2 |
| Bilirubin mg/dL | 0.1-1.0 | 0.2 | 0 | 0.1 | 0.1 |
| AST IU/L | 30-300 | 60 | 52 | 71 | 90 |
| ALT IU/L | 30-200 | 22 | 23 | 23 | 29 |
| Albumin g/dL | 2.5-4.0 | 2.7 | 2.8 | 2.8 | 2.8 |
| Triglycerides mg/dL | 25-100* | 178 | 230 | 250 | 227 |
| Cholesterol mg/dL | 70-125 | 123 | 122 | 129 | 133 |
| Glucose mg/dL | 80-150* | 193 | 187 | 182 | 185 |

TABLE 53

Effect of mixed backbone antisense compound ISIS 360887 on indicators of liver and kidney function

| Serum indicator | Normal Range | Saline | Units measured per dose of ISIS 360887 | | |
|---|---|---|---|---|---|
| | | | 1 mg/kg | 5 mg/kg | 25 mg/kg |
| BUN mg/dL | 15-40 | 27 | 25 | 24 | 23 |
| Creatinine mg/L | 0.0-1.0 | 0.2 | 0.2 | 0.2 | 0.1 |
| Bilirubin mg/dL | 0.1-1.0 | 0.2 | 0.2 | 0.2 | 0.2 |
| AST IU/L | 30-300 | 60 | 60 | 44 | 92 |
| ALT IU/L | 30-200 | 22 | 24 | 22 | 31 |
| Albumin g/dL | 2.5-4.0 | 2.7 | 2.7 | 2.5 | 2.7 |
| Triglycerides mg/dL | 25-100* | 178 | 240 | 262 | 171 |
| Cholesterol mg/dL | 70-125 | 123 | 121 | 129 | 134 |
| Glucose mg/dL | 80-150* | 193 | 189 | 186 | 181 |

*Triglyceride and glucose levels are routinely higher in the Balb/c strain of mice than in other strains of mice.

The levels of routine clinical indicators of liver and kidney injury and disease are within normal ranges and are not significantly changed relative to saline-treated animals, demonstrating that the compounds of the invention do not significantly affect renal or hepatic function. Triglyceride and glucose levels, while outside the normal range as is common in the Balb/c strain, are not significantly elevated relative to saline-treated animals.

The results illustrated in this example demonstrate that mixed backbone compounds are delivered to the kidney, reduce SGLT2 expression in vivo, and that treatment with these compounds does not result in liver or kidney toxicity. Furthermore, the eight dose protocol resulted in greater inhibition of target mRNA levels in the kidney than observed for the four dose protocol shown in Example 22.

Example 24

Antisense Inhibition of SGLT2 in a Murine Model of Type 2 Diabetes: Comparison of Full Phosphorothioate and Mixed Backbone Oligonucleotides The Animal Models of Diabetic Complications Consortium (AMDCC) has developed protocols for the induction of diabetes in a number of animal models. The genetic C57BLKS/J $Lep^{db}/Lep^{db}$ model has been approved by the AMDCC as an appropriate model system for studies of diabetic nephropathy associated with type 2 diabetes.

Leptin is a hormone produced by fat that regulates appetite. Deficiencies in this hormone in both humans and non-human animals lead to obesity. $Lep^{db}/Lep^{db}$ mice have a mutation in the leptin receptor gene which results in obesity and hyperglycemia. As such, these mice are a useful model for the investigation of obesity and diabetes and treatments designed to treat these conditions. In accordance with the present invention, oligomeric compounds of the present invention were tested in the $Lep^{db}/Lep^{db}$ model of type 2 diabetes.

Male $Lep^{db}/Lep^{db}$ mice were given intraperitoneal injections of either ISIS 257016, which has a mixed backbone, or ISIS 145733, which has a phosphorothioate backbone, twice a week for four weeks at doses of 12.5, 25 or 37.5 mg/kg. Saline-injected animals served as controls. Each treatment group contained 6 mice. The mice were sacrificed 2 days following administration of the final dose of oligonucleotide or saline.

Mice were evaluated for SGLT2 levels in kidney. Target levels were determined by quantitative real-time PCR as described by other examples herein. PCR results were normalized to cyclophilin. The data are expressed as percent change relative to saline treated animals ("+" indicates an increase, "−" indicates a decrease) and are illustrated in Table 54.

TABLE 54

Antisense inhibition of SGLT2 mRNA expression in db/db mice (expressed as percent change in SGLT2 mRNA expression relative to saline)

| Dose of oligonucleotide mg/kg | ISIS 145733 | ISIS 257016 |
|---|---|---|
| 12.5 | −48 | −72 |
| 25 | −71 | −72 |
| 37.5 | −64 | −72 |

These results illustrate that both mixed backbone compound ISIS 257016 and full phosphorothioate compound ISIS 145733 effectively inhibit the expression of kidney SGLT2. However, greater inhibition is observed in kidneys from mice treated with ISIS 257016, particularly at the lowest dose of 12.5 mg/kg.

Treated mice were further evaluated for body weight and liver and spleen weight. The data are expressed as weight in grams. The results are presented in Table 55.

TABLE 55

Effects of antisense compounds on total body weight, liver weight and spleen weight of db/db mice (in grams)

| Oligonucleotide | Dose mg/kg | Body weight | Kidney weight | Liver weight | Spleen weight |
|---|---|---|---|---|---|
| Saline | — | 35 | 0.32 | 1.5 | 0.09 |
| ISIS 145733 | 12.5 | 34 | 0.32 | 1.9 | 0.12 |
| ISIS 145733 | 25 | 37 | 0.37 | 2.1 | 0.15 |
| ISIS 145733 | 37.5 | 38 | 0.35 | 2.3 | 0.14 |
| ISIS 257016 | 12.5 | 34 | 0.31 | 1.6 | 0.09 |
| ISIS 257016 | 25 | 36 | 0.31 | 1.7 | 0.08 |
| ISIS 257016 | 37.5 | 34 | 0.35 | 1.8 | 0.11 |

No significant change was observed in total body weight, liver weight or spleen weight at timepoints throughout or at the termination of the study.

Levels of AST, ALT, triglycerides, cholesterol and glucose were measured in mice treated with the compounds of the invention. Plasma samples were analyzed using the Olympus AU400e automated chemistry analyzer (Olympus America, Irving, Tex.). The results, expressed as units measured, are shown in Table 56 and Table 57.

TABLE 56

Effect of full phosphorothioate backbone compound ISIS 145733 on indicators of toxicity

| | | | Units measured per dose of ISIS 145733 | | |
|---|---|---|---|---|---|
| Serum indicator | Normal Range | Saline | 12.5 mg/kg | 25 mg/kg | 37.5 mg/kg |
| AST IU/L | 30-300 | 61 | 72 | 80 | 93 |
| ALT IU/L | 30-200 | 63 | 87 | 101 | 120 |
| Triglycerides mg/dL | 25-100* | 245 | 216 | 243 | 204 |
| Cholesterol mg/dL | 70-125* | 182 | 196 | 211 | 224 |
| Glucose mg/dL | 80-150* | 611 | 452 | 391 | 351 |

TABLE 57

Effect of mixed backbone antisense compound ISIS 257016 on indicators of toxicity

| | | | Units measured per dose of ISIS 257016 | | |
|---|---|---|---|---|---|
| Serum indicator | Normal Range | Saline | 12.5 mg/kg | 25 mg/kg | 37.5 mg/kg |
| AST IU/L | 30-300 | 61 | 120 | 144 | 175 |
| ALT IU/L | 30-200 | 63 | 123 | 142 | 154 |
| Triglycerides mg/dL | 25-100* | 245 | 167 | 188 | 183 |
| Cholesterol mg/dL | 70-125* | 182 | 248 | 264 | 265 |
| Glucose mg/dL | 80-150* | 611 | 281 | 320 | 326 |

*Triglyceride, cholesterol and glucose levels are routinely higher in the $Lep^{db}/Lep^{db}$ strain of mice than in other strains of mice.

The levels of routine clinical indicators of liver injury and disease are within normal ranges and are not significantly changed relative to saline-treated animals, demonstrating that the compounds of the invention do not significantly affect hepatic function. Given the genetic defect of the $Lep^{db}/Lep^{db}$ mice and the diabetic phenotype exhibited by these mice, it is expected that triglyceride, cholesterol and glucose levels will exceed the normal range. Importantly, treatment with either of the SGLT2 antisense compounds resulted in a significant decrease in blood glucose levels, with ISIS 25016, the mixed backbone compound, achieving greater levels of target mRNA inhibition. Treatment with ISIS 257016 also resulted in a significant decrease in serum triglyceride levels.

The results illustrated in this example demonstrate that mixed backbone compounds are effectively delivered to the kidney, reduce SGLT2 expression in vivo, and that treatment with these compounds does not result in liver or other toxicity. Furthermore, these results indicate that mixed backbone compounds targeted to SGLT2 efficiently decrease blood glucose levels and serum triglyceride levels in a mouse model of type 2 diabetes.

Example 25

Antisense Inhibition of SGLT2 in a Murine Model of Type 2 Diabetes: Low Dose Comparison of Full Phosphorothioate and Mixed Backbone Oligonucleotides Since treatment with ISIS 257016 resulted in significant reduction in SGLT2 expression levels even at the lowest dose of 12.5 mg/kg, a second dose-response study was conducted using a lower dose range of 1.56, 3.12 and 6.25 mg/kg. Male Lep$^{db}$/Lep$^{db}$ mice were given intraperitoneal injections of either mixed backbone compound ISIS 257016 or full phosphorothioate compound ISIS 145733 twice a week for four weeks at doses of 1.56, 3.12 or 6.25 mg/kg. Saline-injected animals served as controls. Each treatment group contained 4 mice. The mice were sacrificed 2 days following administration of the final dose of oligonucleotide or saline.

Mice were evaluated for SGLT2 levels in kidney. Target levels were determined by quantitative real-time PCR as described by other examples herein. PCR results were normalized to cyclophilin. The data are expressed as percent change relative to saline treated animals ("+" indicates an increase, "−" indicates a decrease) and are illustrated in Table 58.

TABLE 58

Antisense inhibition of SGLT2 mRNA expression
in db/db mice (expressed as percent change in
SGLT2 mRNA expression relative to saline)

| Dose of oligonucleotide mg/kg | ISIS 145733 | ISIS 257016 |
|---|---|---|
| 1.56 | −13 | −75 |
| 3.12 | −14 | −83 |
| 6.25 | −12 | −80 |

These results illustrate that mixed backbone compound ISIS 257016 is a more effective inhibitor of SGLT2 mRNA expression in the kidney, particularly at low doses of oligonucleotide.

Levels of glucose were measured in mice treated with the compounds of the invention. Plasma samples were analyzed using the Olympus AU400e automated chemistry analyzer (Olympus America, Irving, Tex.). The data are expressed as percent change relative to saline treated animals ("+" indicates an increase, "−" indicates a decrease) and are illustrated in Table 59.

TABLE 59

Blood glucose levels in db/db mice treated with
SGLT2 antisense compounds (expressed as percent
change in blood glucose relative to saline)

| Dose of oligonucleotide mg/kg | ISIS 145733 | ISIS 257016 |
|---|---|---|
| 1.56 | −5 | −41 |
| 3.12 | −7 | −37 |
| 6.25 | −14 | −40 |

The results demonstrate that treatment with mixed backbone compound ISIS 257016 results in a significant decrease in blood glucose levels and that mixed backbone compounds are more effective at lowering blood glucose levels than full phosphorothioate antisense compounds.

Antisense inhibition of SGLT2 by ISIS 257016 was further evaluated using a dose range of 0.39, 0.78 and 1.56 mg/kg. As described above, male Lep$^{db}$/Lep$^{db}$ mice were given intraperitoneal injections of mixed backbone compound ISIS 257016 twice a week for four weeks. Saline-injected animals served as controls. Each treatment group contained 4 mice. The mice were sacrificed 2 days following administration of the final dose of oligonucleotide or saline.

Mice were evaluated for SGLT2 levels in kidney. Target levels were determined by quantitative real-time PCR as described by other examples herein. PCR results were normalized to cyclophilin. Blood glucose levels also were determined. Plasma samples were analyzed using the Olympus AU400e automated chemistry analyzer (Olympus America, Irving, Tex.). The data are expressed as percent change relative to saline treated animals ("+" indicates an increase, "−" indicates a decrease) and are illustrated in Table 60.

TABLE 60

Antisense inhibition of SGLT2 mRNA expression and blood glucose
levels in db/db mice (expressed as percent change in SGLT2 mRNA
expression or blood glucose levels relative to saline)

| Dose of oligonucleotide mg/kg | SGLT2 mRNA | Blood glucose |
|---|---|---|
| 0.39 | −66 | −16 |
| 0.78 | −68 | −21 |
| 1.56 | −82 | −21 |

These results further demonstrate the effectiveness of mixed backbone compounds at inhibiting SGLT2 expression in the kidney and lowering blood glucose levels when administered at very low doses of oligonucleotide.

Mice treated with the compounds of the invention also were evaluated for liver and kidney toxicity, organ and body weights and tissue histology. These studies demonstrated no significant level of toxicity or change in body or organ weight, indicating that mixed backbone compounds are effective in vivo without toxicity to the animal.

The results illustrated in this example demonstrate that mixed backbone compounds are effectively delivered to the kidney, reduce SGLT2 expression in vivo, and that treatment with these compounds lowers blood glucose levels in diabetic animals.

Example 26

Antisense Inhibition of SGLT2 in a Murine Model of Obesity and Diabetes Using Mixed Backbone Compounds Leptin is a hormone produced by fat that regulates appetite. Deficiencies in this hormone in both humans and non-human animals leads to obesity. C57Bl/6J-Lep ob/ob mice have a mutation in the leptin gene which results in obesity and hyperglycemia. As such, these mice are a useful model for the investigation of obesity and diabetes and treatments designed to treat these conditions. In accordance with the present invention, the oligomeric compounds of the invention were tested in the ob/ob model of obesity and diabetes.

Male C57Bl/6J-Lep ob/ob mice (Jackson Laboratory, Bar Harbor, Me.) were subcutaneously injected with ISIS 257016 at a dose of 25 mg/kg two times per week for 4 weeks. Saline-injected animals served as controls. Each treatment group contained 4 mice. The mice were sacrificed 2 days following administration of the final dose of oligonucleotide or saline.

Mice were evaluated for SGLT2 levels in kidney. Target levels were determined by quantitative real-time PCR as described by other examples herein. PCR results were normalized to cyclophilin. Blood glucose levels also were determined. Plasma samples were analyzed using the Olympus AU400e automated chemistry analyzer (Olympus America, Irving, Tex.). The data are expressed as percent change relative to saline treated animals ("+" indicates an increase, "−" indicates a decrease) and are illustrated in Table 61.

TABLE 61

Antisense inhibition of SGLT2 mRNA expression and blood glucose levels in db/db mice (expressed as percent change in SGLT2 mRNA expression or blood glucose levels relative to saline)

| Dose of oligonucleotide mg/kg | SGLT2 mRNA | Blood glucose |
|---|---|---|
| 25 | −83 | −39 |

The results demonstrate that treatment with a mixed backbone SGLT2 antisense compound results in a significant decrease in SGLT2 mRNA expression in the kidney of diabetic mice. Importantly, blood glucose levels also are significantly decreased in treated animals.

Example 27

Comparison of Mixed Backbone Compounds 16 to 20 Nucleobases in Length

In accordance with the present invention, mixed backbone compounds with less than 20 nucleobases were evaluated for their ability to inhibit SGLT2 expression in the kidney. Four compounds were synthesized based on the sequence of ISIS 257016 (SEQ ID NO: 4). ISIS 366847, ISIS 366848, ISIS 366849 and ISIS 366850 are comprised of the 5'-most 19, 18, 17 and 16 nucleobases, respectively, of ISIS 257016. ISIS 257016 has 2'-MOE wings of five nucleobases each and a deoxy gap of 10 nucleobases. ISIS 366847, ISIS 366848, ISIS 366849 and ISIS 366850 have a 10 nucleobases gap, a five nucleobase 2'-MOE wing at the 5' end, but contain a shortened 3' wing of 1 to 4 nucleobases.

Male 6-week old Balb/c mice (Charles River Laboratories, Wilmington, Mass.) were given intraperitoneal injections of ISIS 257016, ISIS 366847, ISIS 366848, ISIS 366849 or ISIS 366850 twice a week for two weeks at doses of 0.14, 0.7 or 3.5 micromoles per kilogram (µM/kg). Saline-injected animals served as controls. Each treatment group contained 4 mice. The mice were sacrificed 2 days following administration of the final dose of oligonucleotide or saline.

Mice were evaluated for SGLT2 levels in kidney. Target levels were determined by quantitative real-time PCR as described in other examples herein. PCR results were normalized to cyclophilin. The data are expressed as percent change relative to saline treated animals ("+" indicates an increase, "−" indicates a decrease) and are illustrated in Table 62.

TABLE 62

Antisense inhibition of SGLT2 mRNA expression in vivo by mixed backbone oligonucleotides (expressed as percent change relative to saline control)

| Dose of oligonucleotide µM/kg | ISIS 257016 | ISIS 366847 | ISIS 366848 | ISIS 366849 | ISIS 366850 |
|---|---|---|---|---|---|
| 0.14 | −53 | −55 | −58 | −57 | −49 |
| 0.7 | −56 | −63 | −59 | −61 | −57 |
| 3.5 | −70 | −64 | −72 | −69 | −69 |

These results illustrate that mixed backbone compounds of the invention, containing 16 to 20 nucleobases, are effective inhibitors of SGLT2 expression in the kidney.

Treated mice were further evaluated for body weight, kidney weight, liver weight and spleen weight. The data are expressed as percent change in body or organ weight ("+" indicates an increase, "−" indicates a decrease). The results are presented in Table 63.

TABLE 63

Effects of antisense compounds on total body weight, kidney weight, liver weight and spleen weight of mice (expressed as percent change in weight)

| Oligonucleotide | Dose µM/kg | Body weight | Kidney weight | Liver weight | Spleen weight |
|---|---|---|---|---|---|
| ISIS 257016 | 0.14 | +9.0 | −4.5 | −6.1 | −8.3 |
| ISIS 257016 | 0.7 | +11.1 | −5.3 | +4.1 | −3.7 |
| ISIS 257016 | 3.5 | +10.2 | −3.6 | +3.7 | +11.9 |
| ISIS 366847 | 0.14 | +15.0 | −0.5 | +0.2 | −6.9 |
| ISIS 366847 | 0.7 | +12.7 | +1.2 | +6.8 | −4.9 |
| ISIS 366847 | 3.5 | +10.3 | +3.6 | +3.8 | +2.9 |
| ISIS 366848 | 0.17 | +8.5 | −7.1 | −7.9 | −2.4 |
| ISIS 366848 | 0.7 | +7.7 | +6.4 | +5.9 | +3.8 |
| ISIS 366848 | 3.5 | +10.8 | +3.0 | +4.6 | +9.3 |
| ISIS 366849 | 0.14 | +6.9 | −3.3 | −2.6 | −7.2 |
| ISIS 366849 | 0.7 | +7.4 | +0.1 | −4.3 | −2.2 |
| ISIS 366849 | 3.5 | +8.4 | −2.9 | −5.2 | −3.9 |
| ISIS 366850 | 0.14 | +11.1 | −3.8 | −4.6 | +2.0 |
| ISIS 366850 | 0.7 | +4.8 | −0.8 | −1.7 | +0.9 |
| ISIS 366850 | 3.5 | 11.2 | −6.0 | +4.5 | +9.8 |

No significant change was observed in total body weight, liver weight or spleen weight at timepoints throughout or at the termination of the study.

Levels of BUN, creatinine, bilirubin, AST, ALT, albumin, triglycerides, cholesterol and glucose were measured in mice treated with the compounds of the invention. Plasma samples were analyzed using the Olympus AU400e automated chemistry analyzer (Olympus America, Irving, Tex.). The results, expressed as units measured, are shown in Tables 64-68.

TABLE 64

Effect of mixed backbone antisense compound ISIS 257016 on indicators of liver and kidney function

| Serum indicator | Normal Range | Saline | Units measured per dose of ISIS 257016 | | |
|---|---|---|---|---|---|
| | | | 0.14 µM/kg | 0.7 µM/kg | 3.5 µM/kg |
| BUN mg/dL | 15-40 | 31 | 32 | 32 | 31 |
| Creatinine mg/L | 0.0-1.0 | 0.2 | 0.2 | 0.2 | 0.2 |
| Bilirubin mg/dL | 0.1-1.0 | 0.2 | 0.1 | 0.1 | 0.1 |
| AST IU/L | 30-300 | 82 | 68 | 85 | 117 |
| ALT IU/L | 30-200 | 22 | 24 | 26 | 32 |
| Albumin g/dL | 2.5-4.0 | 3.0 | 3.2 | 3.1 | 3.1 |
| Triglycerides mg/dL | 25-100* | 225 | 266 | 308 | 225 |
| Cholesterol mg/dL | 70-125 | 123 | 128 | 128 | 147 |
| Glucose mg/dL | 80-150* | 181 | 195 | 187 | 183 |

TABLE 65

Effect of mixed backbone antisense compound ISIS 366847 on indicators of liver and kidney function

| | | | Units measured per dose of ISIS 366847 | | |
|---|---|---|---|---|---|
| Serum indicator | Normal Range | Saline | 0.14 µM/kg | 0.7 µM/kg | 3.5 µM/kg |
| BUN mg/dL | 15-40 | 31 | 29 | 32 | 29 |
| Creatinine mg/L | 0.0-1.0 | 0.2 | 0.2 | 0.2 | 0.2 |
| Bilirubin mg/dL | 0.1-1.0 | 0.2 | 0.1 | 0 | 0.1 |
| AST IU/L | 30-300 | 82 | 53 | 69 | 131 |
| ALT IU/L | 30-200 | 22 | 23 | 28 | 50 |
| Albumin g/dL | 2.5-4.0 | 3.0 | 3.1 | 3.2 | 3.0 |
| Triglycerides mg/dL | 25-100* | 225 | 289 | 308 | 184 |
| Cholesterol mg/dL | 70-125 | 123 | 122 | 132 | 145 |
| Glucose mg/dL | 80-150* | 181 | 173 | 193 | 181 |

TABLE 66

Effect of mixed backbone antisense compound ISIS 366848 on indicators of liver and kidney function

| | | | Units measured per dose of ISIS 366848 | | |
|---|---|---|---|---|---|
| Serum indicator | Normal Range | Saline | 0.14 µM/kg | 0.7 µM/kg | 3.5 µM/kg |
| BUN mg/dL | 15-40 | 31 | 31 | 29 | 32 |
| Creatinine mg/L | 0.0-1.0 | 0.2 | 0.2 | 0.2 | 0.2 |
| Bilirubin mg/dL | 0.1-1.0 | 0.2 | 0.1 | 0.1 | 0.1 |
| AST IU/L | 30-300 | 82 | 82 | 105 | 123 |
| ALT IU/L | 30-200 | 22 | 23 | 34 | 46 |
| Albumin g/dL | 2.5-4.0 | 3.0 | 3.1 | 3.1 | 3.0 |
| Triglycerides mg/dL | 25-100* | 225 | 320 | 374 | 246 |
| Cholesterol mg/dL | 70-125 | 123 | 132 | 142 | 147 |
| Glucose mg/dL | 80-150* | 181 | 200 | 187 | 190 |

TABLE 67

Effect of mixed backbone antisense compound ISIS 366849 on indicators of liver and kidney function

| | | | Units measured per dose of ISIS 366849 | | |
|---|---|---|---|---|---|
| Serum indicator | Normal Range | Saline | 0.14 µM/kg | 0.7 µM/kg | 3.5 µM/kg |
| BUN mg/dL | 15-40 | 31 | 25 | 30 | 33 |
| Creatinine mg/L | 0.0-1.0 | 0.2 | 0.2 | 0.2 | 0.2 |
| Bilirubin mg/L | 0.1-1.0 | 0.2 | 0.1 | 0.1 | 0.1 |
| AST IU/L | 30-300 | 82 | 98 | 90 | 92 |
| ALT IU/L | 30-200 | 22 | 26 | 24 | 33 |
| Albumin g/dL | 2.5-4.0 | 3.0 | 3.0 | 3.0 | 3.0 |
| Triglycerides mg/dL | 25-100* | 225 | 354 | 308 | 240 |
| Cholesterol mg/dL | 70-125 | 123 | 133 | 129 | 150 |
| Glucose mg/dL | 80-150* | 181 | 170 | 173 | 192 |

TABLE 68

Effect of mixed backbone antisense compound ISIS 366850 on indicators of liver and kidney function

| | | | Units measured per dose of ISIS 366850 | | |
|---|---|---|---|---|---|
| Serum indicator | Normal Range | Saline | 0.14 µM/kg | 0.7 µM/kg | 3.5 µM/kg |
| BUN mg/dL | 15-40 | 31 | 26 | 25 | 23 |
| Creatinine mg/L | 0.0-1.0 | 0.2 | 0.2 | 0.2 | 0.2 |
| Bilirubin mg/dL | 0.1-1.0 | 0.2 | 0.1 | 0.1 | 0 |
| AST IU/L | 30-300 | 82 | 83 | 69 | 108 |
| ALT IU/L | 30-200 | 22 | 21 | 27 | 38 |
| Albumin g/dL | 2.5-4.0 | 3.0 | 3.0 | 3.0 | 3.0 |
| Triglycerides mg/dL | 25-100* | 225 | 320 | 380 | 271 |
| Cholesterol mg/dL | 70-125 | 123 | 127 | 131 | 164 |
| Glucose mg/dL | 80-150* | 181 | 192 | 187 | 179 |

*Triglyceride and glucose levels are routinely higher in the Balb/c strain of mice than in other strains of mice.

Some oligonucleotide treated animals exhibited elevated levels of cholesterol; however, saline control animals also demonstrated cholesterol levels at the high end of the normal range. Thus, the slightly elevated cholesterol levels do not appear to be significant. Otherwise, the levels of routine clinical indicators of liver and kidney injury and disease are within normal ranges and are not significantly changed relative to saline-treated animals, demonstrating that the compounds of the invention do not significantly affect renal or hepatic function. Triglyceride and glucose levels, while outside the normal range as is common in the Balb/c strain, are not significantly elevated relative to saline-treated animals.

The results illustrated in this example demonstrate that mixed backbone compounds of 16 to 20 nucleobases are delivered to the kidney, reduce SGLT2 expression in vivo, and that treatment with these compounds does not result in liver or kidney toxicity.

Example 28

Antisense Inhibition of SGLT2 in Sprague Dawley Rats

In accordance with the present invention, 7-week old Sprague Dawley rats (purchased from Charles River Labs, Wilmington, Mass.) were treated with SGLT2 mixed backbone compound ISIS 257016 (SEQ ID NO: 4) or SGLT2 full phosphorothioate compound ISIS 145733 (SEQ ID NO: 4). Rats were injected i.p. twice a week for three weeks with 10 mg/kg of oligonucleotide. Saline-injected animals served as controls. The rats were sacrificed 2 days following administration of the final dose of oligonucleotide or saline.

Rats were evaluated for SGLT2 levels in kidney. Target levels were determined by quantitative real-time PCR as described in other examples herein. PCR results were normalized to cyclophilin. The data are expressed as percent change relative to saline treated animals ("+" indicates an increase, "−" indicates a decrease) and are illustrated in Table 69.

TABLE 69

Antisense inhibition of SGLT2 mRNA expression in Sprague Dawley rats (expressed as percent change in SGLT2 mRNA expression relative to saline)

| Treatment | % Change in mRNA |
|---|---|
| Saline | 0 |
| ISIS 257016 | −83.9 |
| ISIS 145733 | −38.5 |

These results illustrate that both full phosphorothioate and mixed backbone compounds inhibit SGLT2 expression in the kidney of rats. However, the mixed backbone compound is a more effective inhibitor of SGLT2.

Treated rats were further evaluated for body weight, kidney weight, liver weight and spleen weight. For body weight, the data are expressed as percent change in body weight ("+" indicates an increase, "−" indicates a decrease). For organ weights, the results are expressed as percent of saline control normalized to body weight. The results are presented in Table 70 and Table 71.

TABLE 70

Effects of antisense compounds on total body weight of rats (expressed as percent change in weight)

| Treatment | Body weight |
|---|---|
| Saline | +60.7 |
| ISIS 257016 | −58.4 |
| ISIS 145733 | +57.1 |

TABLE 71

Effects of antisense compounds on total kidney weight, liver weight and spleen weight of rats (expressed as percent of saline control normalized to body weight)

| Treatment | Kidney weight | Liver weight | Spleen weight |
|---|---|---|---|
| ISIS 257016 | 99.3 | 93.4 | 105.8 |
| ISIS 145733 | 107.2 | 105.2 | 123.4 |

No significant change was observed in total body weight, kidney weight, liver weight or spleen weight at timepoints throughout or at the termination of the study.

Levels of BUN, creatinine, bilirubin, AST, ALT, albumin, triglycerides, cholesterol and glucose were measured in rats treated with the compounds of the invention. Plasma samples were analyzed using the Olympus AU400e automated chemistry analyzer (Olympus America, Irving, Tex.). The results, expressed as units measured, are shown in Table 72.

TABLE 72

Effect of mixed backbone antisense compound ISIS 257016 and full phosphorothioate compound ISIS 145733 on indicators of liver and kidney function (expressed as units measured)

| Serum Indicator | Saline | ISIS 257016 | ISIS 145733 |
|---|---|---|---|
| BUN mg/dL | 19 | 19 | 17 |
| Creatinine mg/L | 0.3 | 0.4 | 0.2 |
| Bilirubin mg/dL | 0.1 | 0.1 | 0.1 |
| AST IU/L | 157 | 105 | 105 |
| ALT IU/L | 65 | 44 | 36 |
| Albumin g/dL | 3.7 | 3.8 | 3.6 |
| Triglycerides mg/dL | 42 | 47 | 53 |
| Cholesterol mg/dL | 68 | 66 | 54 |
| Glucose mg/dL | 189 | 173 | 180 |

The levels of routine clinical indicators of liver and kidney injury and disease are not significantly changed relative to saline-treated animals, demonstrating that the compounds of the invention do not significantly affect renal or hepatic function in rats.

The results illustrated in this example demonstrate that both full phosphorothioate and mixed backbone compounds are delivered to the kidney, reduce SGLT2 expression in vivo, and that treatment with these compounds does not result in liver or kidney toxicity. The results further indicate that mixed backbone compounds are more effective inhibitors of SGLT2 expression in vivo.

Example 29

Antisense Inhibition of Connective Tissue Growth Factor in a Murine Model of Type 2 Diabetes: Comparison of Full Phosphorothioate and Mixed Backbone Oligonucleotides Three month old C57BLKS/J $Lep^{db}/Lep^{db}$ and age-matched control C57BLKS/J mice were treated twice a week for six weeks with control oligonucleotide ISIS 141923 (CCTTCCCTGAAGGTTCCTCC; SEQ ID NO: 18), or CTGF antisense oligonucleotides ISIS 124212 (CCACAAGCTGTCCAGTCTAA; SEQ ID NO: 19) or ISIS 334157 (CCACAAGCTGTCCAGTCTAA; SEQ ID NO: 19). ISIS 124212, ISIS 334517 and ISIS 141923 are chimeric oligonucleotides ("gapmers") 20 nucleotides in length, composed of a central "gap" region consisting of ten 2'-deoxynucleotides, which is flanked on both sides (5' and 3' directions) by five-nucleotide "wings". The wings are composed of 2'-methoxyethyl (2'-MOE) nucleotides. ISIS 124212 and ISIS 141923 have phosphorothioate (P=S) internucleoside (backbone) linkages throughout the oligonucleotide. ISIS 334517 has a mixed backbone with phosphorothioate linkages in the central gap region and phosphodiester linkages in the wings. All cytidine residues in each oligonucleotide are 5-methylcytidines.

Oligonucleotides were delivered subcutaneously at a dose of 10 mg/kg or 25 mg/kg. Saline-injected animals served as controls. Blood and urine chemistries were analyzed prior to treatment, at three weeks, and post-treatment.

After the treatment period, mice are sacrificed and CTGF mRNA levels were evaluated in the kidney. Target levels were determined by quantitative real-time PCR as described in other examples herein. For mouse CTGF, the PCR primers were:
Forward primer: GCTCAGGGTAAGGTCCGATTC (SEQ ID NO: 26)
Reverse primer: GCCCCCCACCCCAAA (SEQ ID NO: 27)
The PCR probe was: FAM-TCATAATCAAAGAAGCAG-CAAGCACTTCC-TAMRA (SEQ ID NO: 28), where FAM is the fluorescent dye and TAMRA is the quencher dye. The results are illustrated in Table 73.

TABLE 73

Antisense inhibition of CTGF mRNA in $Lep^{db}/Lep^{db}$ kidney (shown as percent of saline-injected control mice)

| Oligonucleotide | Percent expression of CTGF mRNA after treatment with oligonucleotide at the concentrations shown: | | |
|---|---|---|---|
| | Saline | 10 mg/kg | 25 mg/kg |
| 141923 | 100 | — | 82 |
| 124212 | 100 | 110 | 71 |
| 334157 | 100 | 83 | 53 |

Treatment with ISIS 334157 resulted in a significant decrease in CTGF expression at a dose of 25 mg/kg. ISIS 124212 also inhibited expression CTGF at the same dose. These results demonstrate that mixed backbone compounds inhibit expression of target mRNA in the kidney.

To assess distribution of CTGF antisense oligonucleotides in $Lep^{db}/Lep^{db}$ kidney, 2E1 staining was performed as described in other examples herein. The results demonstrated that ISIS 124212 and ISIS 334157 exhibit a similar pattern of distribution in the inner and outer cortex.

To evaluate whether antisense inhibition of CTGF using mixed backbone compounds alters the development of diabetic nephropathy, levels of collagen 1A and collagen IV ($\alpha 2$) were determined. Collagen synthesis is a prerequisite for the development of kidney fibrosis characteristic of diabetic nephorpathy. Collagen 1A and collagen IV ($\alpha 2$) target mRNA levels were determined by quantitative real-time PCR as described by other examples herein.

Probes and primers to mouse collagen 1A and collagen IV ($\alpha 2$) were designed to hybridize to mouse collagen 1A and collagen IV ($\alpha 2$) sequences using published sequence information. For mouse collagen 1A, the PCR primers were:
Forward primer: TGGATTCCCGTTCGAGTACG (SEQ ID NO: 20)
Reverse primer: TCAGCTGGATAGCGACATCG (SEQ ID NO: 21)
The PCR probe was: FAM-AAGCGAGGGCTCCGAC-CCGA-TAMRA (SEQ ID NO: 22)
FAM is the fluorescent dye and TAMRA is the quencher dye. For mouse collagen IV, the PCR primers were:
Forward primer: AGACCAACAAGCAAGTGAGTGC (SEQ ID NO: 23)
Reverse primer: CTAGCATGTGAGCCACATTCATCC (SEQ ID NO: 24)
The PCR probe was: FAM-CTGCTGAGGGCACGCT-GAGCT-TAMRA (SEQ ID NO: 25)
FAM is the fluorescent dye and TAMRA is the quencher dye.

TABLE 74

Inhibition of collagen 1A mRNA expression in $Lep^{db}/Lep^{db}$ mice treated with CTGF antisense oligonucleotide (shown as percent of saline-injected control mice)

| Oligonucleotide | Percent expression of collagen 1A mRNA after treatment with CTGF antisense oligonucleotide at the concentrations shown: | | |
|---|---|---|---|
| | Saline | 10 mg/kg | 25 mg/kg |
| 141923 | 100 | — | 145 |
| 124212 | 100 | 60 | 65 |
| 334157 | 100 | 78 | 75 |

TABLE 75

Inhibition of collagen IV mRNA expression in $Lep^{db}/Lep^{db}$ mice treated with CTGF antisense oligonucleotide (shown as percent of saline-injected control mice)

| Oligonucleotide | Percent expression of collagen IV mRNA after treatment with CTGF antisense oligonucleotide at the concentrations shown: | | |
|---|---|---|---|
| | Saline | 10 mg/kg | 25 mg/kg |
| 141923 | 100 | — | 72 |
| 124212 | 100 | 50 | 40 |
| 334157 | 100 | 37 | 24 |

Treatment with either ISIS 124212 or ISIS 334157 led to a significant reduction in mRNA expression of both collagen 1A and collagen IV in $Lep^{db}/Lep^{db}$ mice, relative to both saline-injected control mice and mice treated with control oligonucleotide. These results indicate that treatment with CTGF antisense oligonuclotides, including mixed backbone compounds, inhibits development of nephropathy associated with type 2 diabetes.

Toxic effects of compounds administered in vivo can be assessed by measuring the levels of enzymes and proteins associated with disease or injury of the liver or kidney. Elevations in the levels of the serum transaminases aspartate aminotransferase (AST) and alanine aminotransferase (ALT) are often indicators of liver disease or injury. To assess the physiological effects resulting from inhibition of target mRNA, the $Lep^{db}/Lep^{db}$ mice were further evaluated at the end of the treatment period for AST and ALT. Serum was analyzed by LabCorp Testing Facility (San Diego, Calif.). The levels of AST and ALT were within normal ranges and were not significantly changed relative to saline-treated animals, demonstrating that the mixed backbone and full phosphorothioate antisense compounds of the invention do not significantly affect hepatic function.

These results illustrate that both full phosphorothioate backbone and mixed backbone compounds are effectively delivered to the kidney, reduce CTGF expression in vivo without toxicity and that these compounds inhibit the development of diabetic nephropathy in diabetic animals.

What is claimed is:

1. A method comprising:
    identifying an animal in which reduction of a preselected target RNA in a kidney cell is desired;
    administering to said animal an antisense oligonucleotide optimized for kidney targeting comprising 8 to 80 linked nucleosides and that is substantially complementary to said preselected target RNA,
    wherein said antisense oligonucleotide comprises a central region consisting of at least 5 contiguous 2'-deoxy nucleosides flanked by a 5' region and a 3' region, wherein said 5' region and said 3' region each independently consists of at least one 2'-O-methoxyethyl nucleoside,
    and wherein the internucleoside linkages of the central region are phosphorothioate linkages and the internucleoside linkages of the 3' region and of the 5' region are phosphodiester linkages; and
    thereby reducing the amount of said preselected target RNA in the kidney cell in said animal.

2. The method of claim 1, wherein said antisense oligonucleotide comprises 10 to 50 linked nucleosides.

3. The method of claim 2, wherein said antisense oligonucleotide comprises 13 to 30 linked nucleosides.

4. The method of claim 3, wherein said antisense oligonucleotide comprises 15 to 25 linked nucleosides.

5. The method of claim 4, wherein said antisense oligonucleotide comprises 18 to 22 linked nucleosides.

6. The method of claim 1, wherein said antisense oligonucleotide has at least 70% complementarity with a nucleic acid molecule encoding said preselected cellular RNA target.

7. The method of claim 1, wherein said antisense oligonucleotide has at least 80% complementarity with a nucleic acid molecule encoding said preselected cellular RNA target.

8. The method of claim 1, wherein said antisense oligonucleotide has at least 90% complementarity with a nucleic acid molecule encoding said preselected cellular RNA target.

9. The method of claim 1, wherein said antisense oligonucleotide has at least 95% complementarity with a nucleic acid molecule encoding said preselected cellular RNA target.

10. A method comprising:
    identifying an animal in which reduction of a preselected target RNA in a kidney cell is desired;
    administering to said animal an antisense oligonucleotide optimized for kidney targeting comprising 8 to 80 linked nucleosides and that is substantially complementary to said preselected target RNA,
    wherein said antisense oligonucleotide comprises a central region consisting of at least 5 contiguous 2'-deoxy nucleosides flanked by a 5' region and a 3' region, wherein said 5' region and said 3' region each independently consists of at least one 2'-O-methoxyethyl nucleoside, and wherein the internucleoside linkages of the central region are phosphorothioate linkages and the internucleoside linkages of the 3' region and of the 5' region are phosphodiester linkages except that one or both of the extreme 5' linkage of the 5' region and the extreme 3' linkage of the 3' region are phosphorothioate linkages and;
    thereby reducing the amount of said preselected target RNA in the kidney cell in said animal.

11. The method of claim 10, wherein said antisense oligonucleotide comprises 10 to 50 linked nucleosides.

12. The method of claim 11, wherein said antisense oligonucleotide comprises 13 to 30 linked nucleosides.

13. The method of claim 12, wherein said antisense oligonucleotide comprises 15 to 25 linked nucleosides.

14. The method of claim 13, wherein said antisense oligonucleotide comprises 18 to 22 linked nucleosides.

15. The method of claim 10, wherein said antisense oligonucleotide has at least 70% complementarity with a nucleic acid molecule encoding said preselected cellular RNA target.

16. The method of claim 10, wherein said antisense oligonucleotide has at least 80% complementarity with a nucleic acid molecule encoding said preselected cellular RNA target.

17. The method of claim 10, wherein said antisense oligonucleotide has at least 90% complementarity with a nucleic acid molecule encoding said preselected cellular RNA target.

18. The method of claim 10, wherein said antisense oligonucleotide has at least 95% complementarity with a nucleic acid molecule encoding said preselected cellular RNA target.

19. The method of claim 1 or claim 10 wherein the animal is selected from mouse, rat, and human.

20. The method of claim 19, wherein the animal is human.

21. The method of claim 1 or claim 10 wherein the animal has a metabolic disease or condition.

22. The method of claim 21, wherein the metabolic disease or condition is diabetes.

23. The method of claim 22, wherein the metabolic disease or condition is type 2 diabetes.

24. The method of claim 1 or claim 10 wherein the said preselected target RNA encodes SGLT2.

25. The method of claim 1 or claim 10 wherein said preselected target RNA encodes CTGF.

* * * * *

SEQUENCE LISTING

<160> NUMBER OF SEQ ID NOS: 28

<210> SEQ ID NO 1
<211> LENGTH: 20
<212> TYPE: DNA
<213> ORGANISM: Artificial Sequence
<220> FEATURE:
<223> OTHER INFORMATION: Antisense Compound

<400> SEQUENCE: 1
tccgtcatcg ctcctcaggg                                                        20

<210> SEQ ID NO 2
<211> LENGTH: 20
<212> TYPE: DNA
<213> ORGANISM: Artificial Sequence
<220> FEATURE:
<223> OTHER INFORMATION: Antisense Compound

<400> SEQUENCE: 2
gtgcgcgcga gcccgaaatc                                                        20

<210> SEQ ID NO 3
<211> LENGTH: 20
<212> TYPE: DNA
<213> ORGANISM: Artificial Sequence
<220> FEATURE:
<223> OTHER INFORMATION: Antisense Compound

<400> SEQUENCE: 3
atgcattctg cccccaagga                                                        20

<210> SEQ ID NO 4
<211> LENGTH: 20
<212> TYPE: DNA
<213> ORGANISM: Artificial Sequence
<220> FEATURE:
<223> OTHER INFORMATION: Antisense Compound

<400> SEQUENCE: 4
gaagtagcca ccaactgtgc                                                        20

<210> SEQ ID NO 5
<211> LENGTH: 20
<212> TYPE: DNA
<213> ORGANISM: Artificial Sequence
<220> FEATURE:
<223> OTHER INFORMATION: Antisense Compound

<400> SEQUENCE: 5
gagaacatat ccaccgagat                                                        20

<210> SEQ ID NO 6
<211> LENGTH: 20
<212> TYPE: DNA
<213> ORGANISM: Artificial Sequence
<220> FEATURE:
<223> OTHER INFORMATION: Antisense Compound

<400> SEQUENCE: 6
ctgcacagtg tctgtgtaca                                                        20

<210> SEQ ID NO 7
<211> LENGTH: 2454
<212> TYPE: DNA

<213> ORGANISM: Mus musculus
<220> FEATURE:
<221> NAME/KEY: misc_feature
<222> LOCATION: 510, 657, 702, 741, 1231, 1370, 1426, 1432, 1677
<223> OTHER INFORMATION: n = A,T,C or G

<400> SEQUENCE: 7

```
agagaatgga gcaacacgta gaggcaggct ctgaacttgg ggagcagaag gtcctgattg      60
ataatcctgc tgacattctg gttatcgctg cctatttcct gctggtcatt ggtgttggct     120
tgtggtctat gttcagaacc aatagaggca cagttggtgg ctacttcctg gcaggacgga     180
acatggtgtg gtggccggtt ggagcctctc tgttcgccag caacatcggc agcggtcatt     240
ttgtgggcct ggcagggact ggtgcagcaa gtggcttggc ggtggctgga tttgagtgga     300
atgcgctctt cgtggtgctg ctcctcggat ggcttttgt gccagtgtat ctgaccgctg      360
gcgtgatcac aatgcctcag tacctccgca agcgctttgg tgggcaccgt attcgcctct     420
acctgtccgt gctctcgctt ttttgtaca ttttcaccaa gatctcggtg gatatgttct      480
ctggggcagt attcattcaa caggccctgn gctggaacat ttacgcttcg gtcatcgctc     540
tcttgggcat caccatgatt tatactgtga caggagggct ggcggcactg atgtacacag     600
acactgtgca gaccttcgtc attcttgccg gggcctccat cctcactggt tatgctntcc     660
atgaagtggg cggtacttc ggtctcttcg acacatacct gngagcaatg acttcactga      720
cgggtgtcca ggatccatct ngtgggcaca tctccagcac ctgctaccag ccgaggcctg     780
actcctatca cctgctgcgt gaccctgtga caggagacct gccatggcct gcgctgctcc     840
tggggcttac cattgtctcg ggctggtatt ggtgcagcga tcaggtaata gtgcagcggt     900
gcctggctgg aaagaatctg actcacatca aagctgggtg catcttgtgt ggctacctga     960
agctgatgcc catgttcctc atggtcatgc caggcatgat cagccgcatt ctctacccag    1020
atgaggtggc atgtgtggta cctgaggtgt gtaagcgggt gtgtggcact gaggtgggct    1080
gctctaacat cgcctaccca cagctcgtgg tgaagctcat gcccaatggt ctgcgcggac    1140
tcatgctggc agtcatgctg gctgccctca tgtcttctct ggcatccatc tttaacagca    1200
gtagcacgct cttcaccatg gatatctaca ncgcgcctgc ggcccgtgca ggtgataagg    1260
agctgctgct agttggaagg ctctgggtgg tattcatcgt ggcggtgtcc gtggctcggc    1320
tgccagtggt gcaggcagct cagggtgggc agctcttcga ttacatcagn tctgtctcca    1380
gctatctggc acctcaagtg tctgcggtct ttgtgcttgc actctntgtg cnccgtgtta    1440
atgagaaggg agccttctgg ggactagttg ggggcctgct gatgggccta gctcgtctca    1500
tacccgagtt cttctttggc tcgggcagct gtgtgcgacc ctcagcgtgc ccggcactct    1560
tctgtcgggt acactacctc tatttcgcca tcattctctt catctgctct ggcatcctca    1620
cactgggaat ctccctgtgc actggcccat cccctcagaa gcatctccat cgctggnttt    1680
tcagtctccg gcacagcaag gaggagcggg aggacctgga tgctgatgag ttagaaggtc    1740
cagcccctgc tcctgtgcag aacgggggcc aggaatgtgc aatggagatg gaagaggtcc    1800
agtccccggc tccaggcctg ctccgccggt gcctgctttg gttctgtggg atgagcaaga    1860
gtgggtcagg gagtcctccg cccactaccg aggaggtggc ggcaaccacc aggcggctgg    1920
aggacatcag tgaggatccc cgctgggcac gagtagtcaa cctcaatgcc ctactcatga    1980
tgaccgtggc tgtgttcctc tggggcttct atgcataaag tcgagggtgt tggatgccat    2040
gagctacaac caggccatgt tggacccctca caaagagtaa gggtgagcag cttggagtgg    2100
atcccagaaa aggaacaggg caagaataca gcaggaagga accggttccc ttcctcttta    2160
```

```
cccgggtcc  agtccatttg  attggttgtc  acttcccaca  agatgatggc  caattggtca    2220
tagaggtttg  cctatacaaa  aataaaactg  ccctcctaac  atcctgttgt  ggctgaaaca    2280
tcgttgctct  cggcttcatc  ctggtctctg  ggctcctgtt  ctgggtcctg  ggcttggagc    2340
acggttgctc  ataagacctt  cttttctgga  gacaagggcc  atgtggccct  ccactcatcc    2400
acctctagat  ggtgtttctc  cgtcttccag  ccagcagcct  gcagtccttt  caag          2454
```

```
<210> SEQ ID NO 8
<211> LENGTH: 20
<212> TYPE: DNA
<213> ORGANISM: Artificial Sequence
<220> FEATURE:
<223> OTHER INFORMATION: Antisense Compound

<400> SEQUENCE: 8
tcgatctcct tttatgcccg                                                     20

<210> SEQ ID NO 9
<211> LENGTH: 24
<212> TYPE: DNA
<213> ORGANISM: Artificial Sequence
<220> FEATURE:
<223> OTHER INFORMATION: PCR Primer

<400> SEQUENCE: 9
ctcgtctcat acccgagttc ttct                                                24

<210> SEQ ID NO 10
<211> LENGTH: 27
<212> TYPE: DNA
<213> ORGANISM: Artificial Sequence
<220> FEATURE:
<223> OTHER INFORMATION: PCR Primer

<400> SEQUENCE: 10
aatgatggcg aaatagaggt agtgtac                                             27

<210> SEQ ID NO 11
<211> LENGTH: 19
<212> TYPE: DNA
<213> ORGANISM: Artificial Sequence
<220> FEATURE:
<223> OTHER INFORMATION: PCR Probe

<400> SEQUENCE: 11
tgcgaccctc agcgtgccc                                                      19

<210> SEQ ID NO 12
<211> LENGTH: 15
<212> TYPE: DNA
<213> ORGANISM: Artificial Sequence
<220> FEATURE:
<223> OTHER INFORMATION: PCR Primer

<400> SEQUENCE: 12
tcgccgcttg ctgca                                                          15

<210> SEQ ID NO 13
<211> LENGTH: 17
<212> TYPE: DNA
<213> ORGANISM: Artificial Sequence
<220> FEATURE:
<223> OTHER INFORMATION: PCR Primer

<400> SEQUENCE: 13
```

```
atcggccgtg atgtcga                                                    17

<210> SEQ ID NO 14
<211> LENGTH: 23
<212> TYPE: DNA
<213> ORGANISM: Artificial Sequence
<220> FEATURE:
<223> OTHER INFORMATION: PCR Probe

<400> SEQUENCE: 14
ccatggtcaa ccccaccgtg ttc                                             23

<210> SEQ ID NO 15
<211> LENGTH: 25
<212> TYPE: DNA
<213> ORGANISM: Artificial Sequence
<220> FEATURE:
<223> OTHER INFORMATION: PCR Primer

<400> SEQUENCE: 15
atggagcaac acgtagaggc aggct                                           25

<210> SEQ ID NO 16
<211> LENGTH: 25
<212> TYPE: DNA
<213> ORGANISM: Artificial Sequence
<220> FEATURE:
<223> OTHER INFORMATION: PCR Primer

<400> SEQUENCE: 16
gagtgccgcc agccctcctg tcaca                                           25

<210> SEQ ID NO 17
<211> LENGTH: 20
<212> TYPE: DNA
<213> ORGANISM: Artificial Sequence
<220> FEATURE:
<223> OTHER INFORMATION: Antisense Compound

<400> SEQUENCE: 17
ccttccctga aggttcctcc                                                 20

<210> SEQ ID NO 18
<211> LENGTH: 20
<212> TYPE: DNA
<213> ORGANISM: Artificial Sequence
<220> FEATURE:
<223> OTHER INFORMATION: Antisense Compound

<400> SEQUENCE: 18
ccttccctga aggttcctcc                                                 20

<210> SEQ ID NO 19
<211> LENGTH: 20
<212> TYPE: DNA
<213> ORGANISM: Artificial Sequence
<220> FEATURE:
<223> OTHER INFORMATION: Antisense Compound

<400> SEQUENCE: 19
ccacaagctg tccagtctaa                                                 20

<210> SEQ ID NO 20
<211> LENGTH: 20
<212> TYPE: DNA
<213> ORGANISM: Artificial Sequence
<220> FEATURE:
```

<223> OTHER INFORMATION: PCR Primer

<400> SEQUENCE: 20
tggattcccg ttcgagtacg                                                    20

<210> SEQ ID NO 21
<211> LENGTH: 20
<212> TYPE: DNA
<213> ORGANISM: Artificial Sequence
<220> FEATURE:
<223> OTHER INFORMATION: PCR Primer

<400> SEQUENCE: 21
tcagctggat agcgacatcg                                                    20

<210> SEQ ID NO 22
<211> LENGTH: 20
<212> TYPE: DNA
<213> ORGANISM: Artificial Sequence
<220> FEATURE:
<223> OTHER INFORMATION: PCR Probe

<400> SEQUENCE: 22
aagcgagggc tccgacccga                                                    20

<210> SEQ ID NO 23
<211> LENGTH: 22
<212> TYPE: DNA
<213> ORGANISM: Artificial Sequence
<220> FEATURE:
<223> OTHER INFORMATION: PCR Primer

<400> SEQUENCE: 23
agaccaacaa gcaagtgagt gc                                                 22

<210> SEQ ID NO 24
<211> LENGTH: 24
<212> TYPE: DNA
<213> ORGANISM: Artificial Sequence
<220> FEATURE:
<223> OTHER INFORMATION: PCR Primer

<400> SEQUENCE: 24
ctagcatgtg agccacattc atcc                                               24

<210> SEQ ID NO 25
<211> LENGTH: 21
<212> TYPE: DNA
<213> ORGANISM: Artificial Sequence
<220> FEATURE:
<223> OTHER INFORMATION: PCR Probe

<400> SEQUENCE: 25
ctgctgaggg cacgctgagc t                                                  21

<210> SEQ ID NO 26
<211> LENGTH: 21
<212> TYPE: DNA
<213> ORGANISM: Artificial Sequence
<220> FEATURE:
<223> OTHER INFORMATION: PCR Primer

<400> SEQUENCE: 26
gctcagggta aggtccgatt c                                                  21

<210> SEQ ID NO 27

```
<211> LENGTH: 15
<212> TYPE: DNA
<213> ORGANISM: Artificial Sequence
<220> FEATURE:
<223> OTHER INFORMATION: PCR Primer

<400> SEQUENCE: 27 gcccccccacc ccaaa                                                        15

<210> SEQ ID NO 28
<211> LENGTH: 29
<212> TYPE: DNA
<213> ORGANISM: Artificial Sequence
<220> FEATURE:
<223> OTHER INFORMATION: PCR Probe

<400> SEQUENCE: 28
tcataatcaa agaagcagca agcacttcc                                          29
```